US008945833B2

(12) United States Patent
Stuyver et al.

(10) Patent No.: US 8,945,833 B2
(45) Date of Patent: Feb. 3, 2015

(54) METHOD FOR DETERMINING DRUG RESISTANCE MUTATIONS IN ANY OF THE NON-STRUCTURAL PROTEIN REGIONS NS3 TO NS5B OF HEPATITIS C VIRUS (HCV) FOR GENOTYPES 1 TO 6

(76) Inventors: Lieven Jozef Stuyver, Herzele (BE); Diana Koletzki, Etterbeek (BE); Jan Martin Berke, Willebroek (BE); Ina Isabel Vandenbroucke, Verrebroek (BE); Leen Roger Vijgen, Herselt (BE)

( * ) Notice: Subject to any disclaimer, the term of this patent is extended or adjusted under 35 U.S.C. 154(b) by 516 days.

(21) Appl. No.: 13/122,614

(22) PCT Filed: Oct. 6, 2009

(86) PCT No.: PCT/EP2009/062986
§ 371 (c)(1),
(2), (4) Date: Apr. 5, 2011

(87) PCT Pub. No.: WO2010/040756
PCT Pub. Date: Apr. 15, 2010

(65) Prior Publication Data

US 2011/0189684 A1 Aug. 4, 2011

(30) Foreign Application Priority Data

Oct. 6, 2008 (EP) .................................... 08165949

(51) Int. Cl.
*C12Q 1/68* (2006.01)
*C12Q 1/70* (2006.01)

(52) U.S. Cl.
CPC .............. *C12Q 1/707* (2013.01); *C12Q 1/6897* (2013.01)
USPC ...... 435/6.1; 536/22.1; 536/24.33; 435/320.1

(58) Field of Classification Search
None
See application file for complete search history.

(56) References Cited

U.S. PATENT DOCUMENTS 7,329,732 B2 * 2/2008 Graham et al. ............... 530/350

FOREIGN PATENT DOCUMENTS

| | | | |
|---|---|---|---|
| EP | 1801116 | | 6/2007 |
| WO | WO 9727480 | | 7/1997 |
| WO | WO 2004080406 | A2 * | 9/2004 |
| WO | WO 2006021896 | A2 * | 3/2006 |
| WO | WO 2008/002165 | | 1/2008 |
| WO | WO 2008002165 | A2 * | 1/2008 |
| WO | WO 2008/046922 | | 4/2008 |
| WO | WO 2008060608 | | 5/2008 |
| WO | WO 2008/090 185 | | 7/2008 |

OTHER PUBLICATIONS

Sandres-Saune et al. (J Virol Methods. May 2003;109(2):187-93).*
NCBI Accession Nos. DQ220824 (Sep. 30, 2006), DQ220904 (Sep. 30, 2006), DQ061343 (2005), DQ061300 (Jun. 20, 2005), AF238481 (Sep. 5, 2007), AY232735 (Sep. 5, 2007), AF046866 (Sep. 5, 2007), AM423035 (Dec. 12, 2007), Y11604 (Nov. 10, 2005), AY685579 (Aug. 14, 2004).*
Rozen et al. (Primer3 on the WWW for General Users and for Biologist Programmers, in Methods in Molecular Biology, vol. 132: Bioinformatics Methods and Protocols, 2000).*
Okimoto et al. (Improved PCR Amplification of Multiple Specific Alleleso(PAMSA) Using Internally Mismatched Primers, BioTechniques 26 (Jul. 1996)).*
Kwok et al. (A Guide to the Design and Use of Mismatched and Degenerate Primers, Genome Res. 1994 3: S39-S47).*
Buck et al. ("Design Strategies and Performance of Custom DNA Sequencing Primers" Biotechniques. 1999. 27(3): pp. 528-536).*
Lowe et al. (Nucleic Acids Research, vol. 18, No. 7, p. 1757-1761, 1990).*
Hamano, Kosei et al. "Mutations in the NS5B Region of the Hepatitis C Virus Genome Correlate with Clinical Outcomes of Interferon-Alpha Plus Ribavirin Combination Therapy". Journal of Gastroenterology and Hepatology, (2005) 20, pp. 1401-1409.
Tomei, Licia, et al. "HCV Antiviral Resistance: The Impact of In Vitro Studies on the Development of Antiviral Agents Targeting the Viral NS5B Polymerase". Antiviral Chemistry & Chemotherapy, (2005), 16, pp. 225-245.
Simmonds, P. et al. "Classification of Hepatitis C Virus into Six Major Genotypes and a Series of Subtypes by Phylogenetic Analysis of the NS-5 Region". Journal of General Virology (1993) 74, pp. 2391-2399. (Published Great Britain).
Khromykh, Alexander et al. "Coupling between Replication and Packaging of Flavivirus RNA: Evidence Derived from the Use of DNA-Bases Full-Length cDNA Clones of Kunjin Virus". Journal of Virology, (May 2001) vol. 75, No. 10, pp. 4633-4640.
Hertogs, Kurt at al. "A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs". Antimicrobial Agents and Chemotherapy, (Feb. 1998), pp. 269-276.
Lin, Chao et al. "In Vitro Studies of Cross-Resistance Mutations Against Two Hepatitis C Virus Serine Protease Inhibitors, VX-950 and BILN 2061" Journal of Biological Chemistry, (Nov. 2005), vol. 280, No. 44, pp. 36784-36791.
Kellam, Paul et al. "Recombinant Virus Assay: A Rapid, Phenotypic Assay for Assessment of Drug Susceptibility of Human Immunodeficiency Virus I Isolates", Antimicrobial Agents and Chemotherapy, (Jan. 1994), vol. 38, No. 1, pp. 23-30.
Prabhu, Ramesh, et al. "Interferon Alpha-2b Inhibits Negative-Strand RNA and Protein Expression from Full-Length HCV1a Infectious Clone", Experimental and Molecular Pathology (2004), 76, pp. 242-252.
Dumont, S. et al. "Development of a Platform to Detect Drug Resistance Mutations in the Non-Structural Protein Region of the Hepatitis C Virus Genotypes 1,2,3, and 4", Journal of Hepatology, (Apr. 2009), vol. 50, p. S124 #319.
Vizmanos, J.L. et al. "Degree and Distribution of Variability in the 5' Untranslated E1, E2/NS1 and NS5 Regions of the Hepatitis C Virus (HCV)", Journal of Viral Hepatitis, (1998), 5, pp. 227-240.

(Continued)

*Primary Examiner* — Christopher M Babic
*Assistant Examiner* — Aaron Priest

(57) ABSTRACT

The present invention relates to a method for determining drug resistance mutations in any of the non-structural protein regions NS3 to NS5B of Hepatitis C Virus (HCV) for genotypes 1 to 6, more in particular for subtype specific genotypes 1a, 1b, 2a, 2b, 3a, 4a and 4d.

1 Claim, 4 Drawing Sheets

(56) References Cited

OTHER PUBLICATIONS

Sandres-Saune, K. et al. "Determining Hepatitis C Genotype by Analyzing the Sequence of the NS5B Region", Journal of Virological Methods, (2003), 109, pp. 187-193.

Lohmann, Volker et al. "Viral and Cellular Determinants of Hepatitis C Virus RNA Replication in Cell Culture", Journal of Virology, (Mar. 2003), vol. 77, No. 5, pp. 3007-3019.

Le Guillou-Guillemette, H. et al. "Genetic Diversity of the Hepatitis C Virus: Impact and Issues in the Antiviral Therapy", World Journal of Gastroenterology, (May 2007), pp. 2416-2426.

Krieger, N. et al. "Enhancement of Hepatitis C RNA Replication by Cell Culture-Adaptive Mutations", Journal of Virology, (May 2001), vol. 75, No. 10, pp. 4614-4624.

* cited by examiner

Figure 2: Overview of generated amplicons for the subtyping and genotyping assays
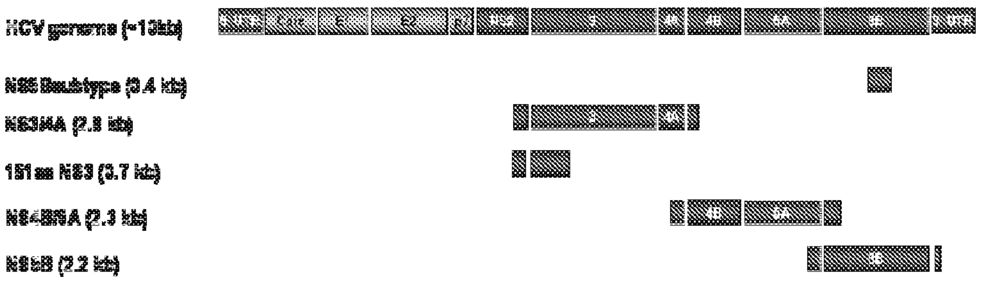
Figure 3
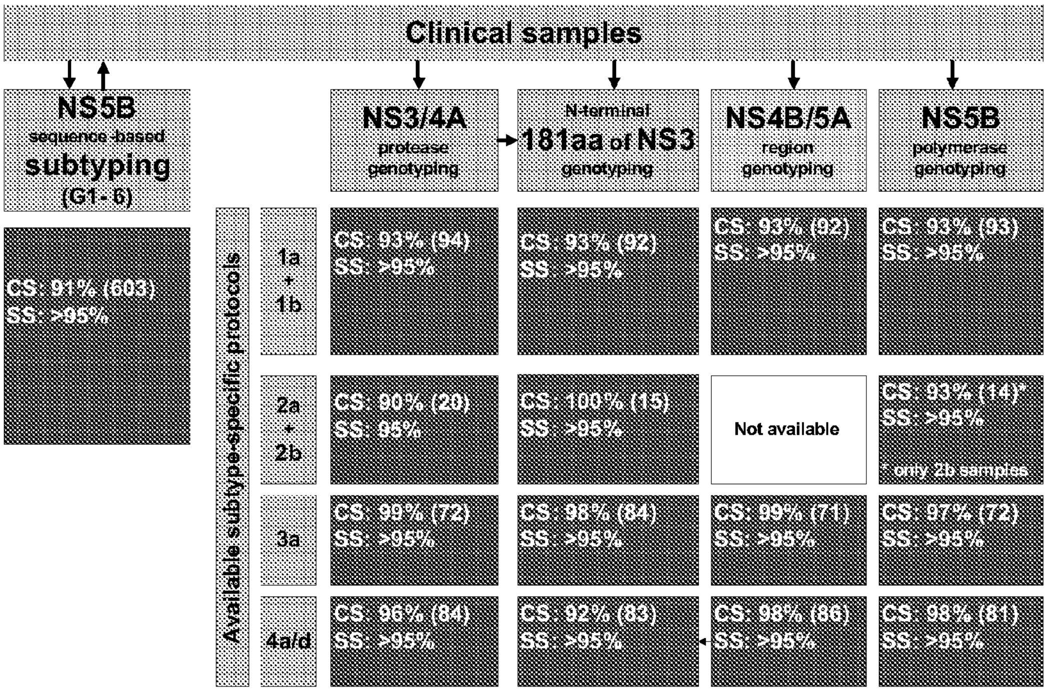
CS: Clinical sensitivity (amplification hit rate at high viral load) in %;
SS: Clinical sensitivity (sequencing hit rate of generated amplicons) in %; numbers in brackets = total number of tested HCV-positive samples.

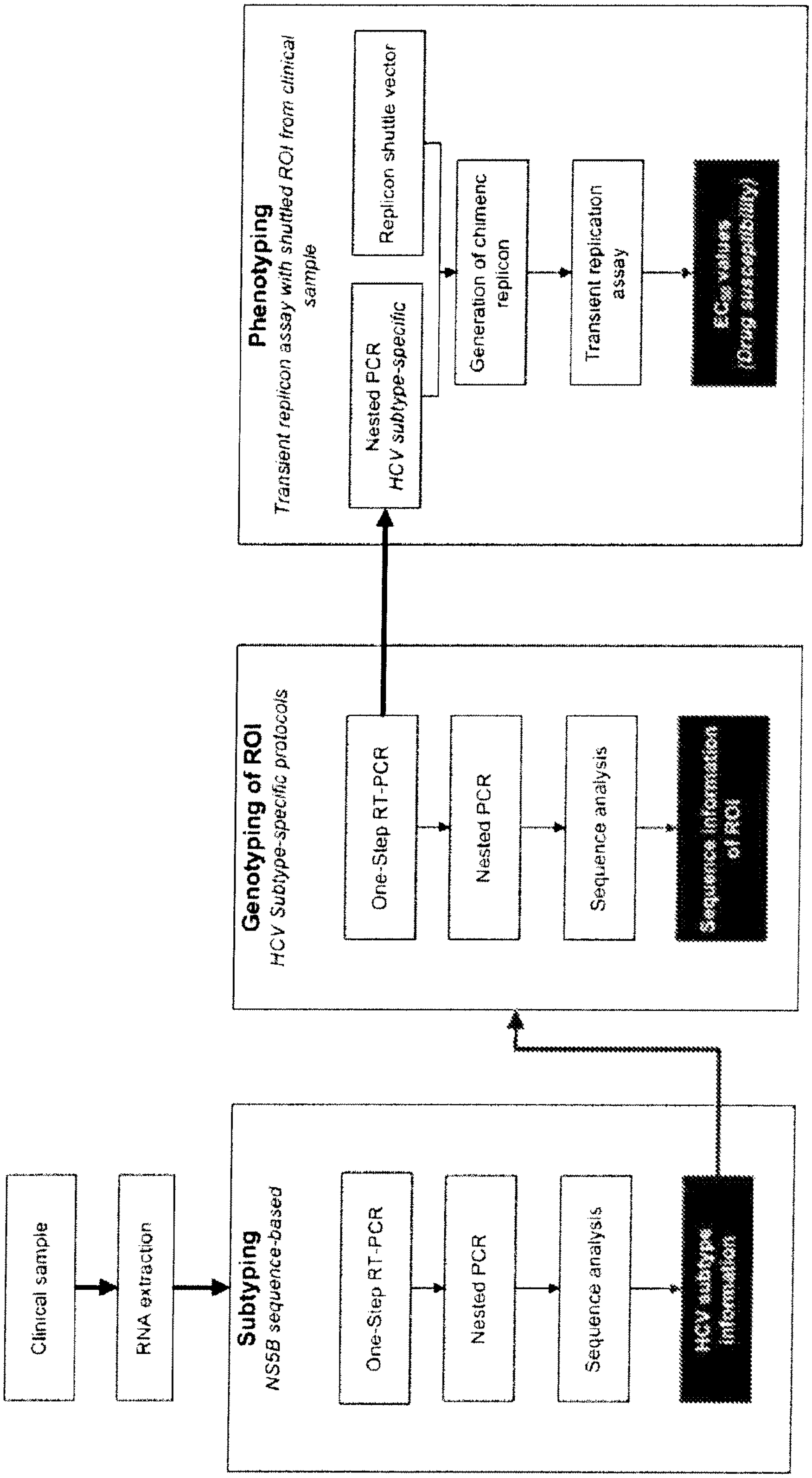
Figure 5: Process overview
ROI, region of interest.

SEQUENCE LISTING

<160> NUMBER OF SEQ ID NOS: 228

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
tggggttcgc gtatgatacc cgctgctttg a 31

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
tggggttttc ttacgacacc aggtgctttg a 31

<210> SEQ ID NO 3

<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
ccgtatgata cccgctgctt tgactcaac 29

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
tcctacgaca ccaggtgctt tgattcaac 29

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
aattcctggt catagcctcc gtgaagactc 30

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
gcgtgtgggg acatcatctt agg 23

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
gctgccagtg ggagcgtg 18

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
tcatcttagg cctgcccgtc tc 22

<210> SEQ ID NO 9
<211> LENGTH: 21

<212> TYPE: DNA
<213> ORGANISM: Artificial Sequence
<220> FEATURE:
<223> OTHER INFORMATION: Description of Artificial Sequence: Synthetic
primer

<400> SEQUENCE: 9
gggagcgtgt agatgggcca c 21

<210> SEQ ID NO 10
<211> LENGTH: 12003
<212> TYPE: DNA
<213> ORGANISM: Hepatitis C virus

<400> SEQUENCE: 10
ctccaccata gatcactccc ctgtgaggaa ctactgtctt cacgcagaaa gcgtctagcc 60
atggcgttag tatgagtgtc gtgcagcctc caggaccccc cctcccggga gagccatagt 120
ggtctgcgga accggtgagt acaccggaat tgccaggacg accgggtcct ttcttggatc 180
aacccgctca atgcctggag atttgggcgt gcccccgcga gactgctagc cgagtagtgt 240
tgggtcgcga aaggccttgt ggtactgcct gatagggtgc ttgcgagtgc cccgggaggt 300
ctcgtagacc gtgcaccgtt taaacccccg tgctgctgga agtcgatttc gcttagggta 360
accgtggacc tcgaaaacag acgcacaaaa ccaagttcaa tagaaggggg tacaaaccag 420
taccaccacg aacaagcact tctgtttccc cggtgatgtc gtatagactg cttgcgtggt 480
tgaaagcgac ggatccgtta tccgcttatg tacttcgaga agcccagtac cacctcggaa 540
tcttcgatgc gttgcgctca gcactcaacc ccagagtgta gcttaggctg atgagtctgg 600
acatccctca ccggtgacgg tggtccaggc tgcgttggcg gcctacctat ggctaacgcc 660
atgggacgct agttgtgaac aaggtgtgaa gagcctattg agctacataa gaatcctccg 720
gcccctgaat gcggctaatc ccaacctcgg agcaggtggt cacaaaccag tgattggcct 780
gtcgtaacgc gcaagtccgt ggcggaaccg actactttgg gtgtccgtgt ttccttttat 840
tttattgtgg ctgcttatgg tgacaatcac agattgttat cataaagcga attggattgg 900
ccatccggtg aaagtgagac tcattatcta tctgtttgct ggatccgctc cattgagtgt 960
gtttactcta agtacaattt caacagttat ttcaatcaga caattgtatc ataatggcgg 1020
gcccagaaga cgccaaaaac ataaaggaag gcccggcgcc attctatcct ctagaggatg 1080
gaaccgctgg agagcaactg cataaggcta tgaagagata cgccctggtt cctggaacaa 1140
ttgcttttac agatgcacat atcgaggtga acatcacgta cgcggaatac ttcgaaatgt 1200
ccgttcggtt ggcagaagct atgaaacgat atgggctgaa tacaaatcac agaatcgtcg 1260
tatgcagtga aaactctctt caattcttta tgccggtgtt gggcgcgtta tttatcggag 1320
ttgcagttgc gcccgcgaac gacatttata atgaacgtga attgctcaac agtatgaaca 1380
tttcgcagcc taccgtagtg tttgtttcca aaaaggggtt gcaaaaaatt ttgaacgtgc 1440
aaaaaaaatt accaataatc cagaaaatta ttatcatgga ttctaaaacg gattaccagg 1500
gatttcagtc gatgtacacg ttcgtcacat ctcatctacc tcccggtttt aatgaatacg 1560
attttgtacc agagtccttt gatcgtgaca aaacaattgc actgataatg aattcctctg 1620
gatctactgg gttacctaag ggtgtggccc ttccgcatag aactgcctgc gtcagattct 1680
cgcatgccag agatcctatt tttggcaatc aaatcattcc ggatactgcg attttaagtg 1740
ttgttccatt ccatcacggt tttggaatgt ttactacact cggatatttg atatgtggat 1800
ttcgagtcgt cttaatgtat agatttgaag aagagctgtt tttacgatcc cttcaggatt 1860

-continued

```
acaaaattca aagtgcgttg ctagtaccaa ccctattttc attcttcgcc aaaagcactc   1920
tgattgacaa atacgattta tctaatttac acgaaattgc ttctgggggc gcacctcttt   1980
cgaaagaagt cggggaagcg gttgcaaaac gcttccatct tccagggata cgacaaggat   2040
atgggctcac tgagactaca tcagctattc tgattacacc cgagggggat gataaaccgg   2100
gcgcggtcgg taaagttgtt ccattttttg aagcgaaggt tgtggatctg gataccggga   2160
aaacgctggg cgttaatcag agaggcgaat tatgtgtcag aggacctatg attatgtccg   2220
gttatgtaaa caatccggaa gcgaccaacg ccttgattga caaggatgga tggctacatt   2280
ctggagacat agcttactgg gacgaagacg aacacttctt catagttgac cgcttgaagt   2340
ctttaattaa atacaaagga tatcaggtgg cccccgctga attggaatcg atattgttac   2400
aacaccccaa catcttcgac gcgggcgtgg caggtcttcc cgacgatgac gccggtgaac   2460
ttcccgccgc cgttgttgtt ttggagcacg gaaagacgat gacggaaaaa gagatcgtgg   2520
attacgtcgc cagtcaagta acaaccgcga aaaagttgcg cggaggagtt gtgtttgtgg   2580
acgaagtacc gaaaggtctt accggaaaac tcgacgcaag aaaaatcaga gagatcctca   2640
taaaggccaa gaagggcgga aagtccaaat tgtaagcggc cgcgttgtta aacagaccac   2700
aacggtttcc ctctagcggg atcaattccg cccccccccc ctaacgttac tagccgaagc   2760
cgcttggaat aaggccggtg tgcgtttgtc tatatgttat tttccaccat attgccgtct   2820
tttggcaatg tgagggcccg gaaacctggc cctgtcttct tgacgagcat tcctaggggt   2880
ctttcccctc tcgccaaagg aatgcaaggt ctgttgaatg tcgtgaagga agcagttcct   2940
ctggaagctt cttgaagaca aacaacgtct gtagcgaccc tttgcaggca gcggaacccc   3000
ccacctggcg acaggtgcct ctgcggccaa aagccacgtg tataagatac acctgcaaag   3060
gcggcacaac cccagtgcca cgttgtgagt tggatagttg tggaaagagt caaatggctc   3120
tcctcaagcg tattcaacaa ggggctgaag gatgcccaga aggtacccca ttgtatggga   3180
tctgatctgg ggcctcggtg cacatgcttt acatgtgttt agtcgaggtt aaaaaaacgt   3240
ctaggccccc cgaaccacgg ggacgtggtt ttcctttgaa aaacacgata ataccatggc   3300
gcctattacc gcggtaccgc agacattcca ggtggcccat ctacacgccc ctactggtag   3360
cggcaagagc actaaggtgc cggctgcgta tgcagcccaa gggtataagg tgcttgtcct   3420
gaacccgtcc gtcgccgcca ccctaggttt cggggcgtat atgtctaagg cacatggtat   3480
cgaccctaac atcagaatcg gggtaaggac catcaccacg ggtgccccca tcacgtactc   3540
cacctatggc aagtttcttg ccgacggtgg ttgctctggg ggcgcctatg acatcataat   3600
atgtgatgag tgccactcaa ctgactcgac cactatcctg ggcatcggca cagtcctgga   3660
ccaagcggag acggctggag cgcgactcgt cgtgctcgcc accgctacgc ctccgggatc   3720
ggtcaccgtg ccacatccaa acatcgagga ggtggctctg tccagcactg gagaaatccc   3780
cttttatggc aaagccatcc ccatcgagac catcaagggg gggaggcacc tcattttctg   3840
ccattccaag aagaaatgtg atgagctcgc cgcgaagctg tccggcctcg gactcaatgc   3900
tgtagcatat taccggggcc ttgatgtatc cgtcatacca actagcggag acgtcattgt   3960
cgtagcaacg gacgctctaa tgacgggctt taccggcgat ttcgactcag tgatcgactg   4020
caatacatgt gtcacccaga cagtcgactt cagcctggac ccgaccttca ccattgagac   4080
gacgaccgtg ccacaagacg cggtgtcacg ctcgcagcgg cgaggcagga ctggtagggg   4140
caggatgggc atttacaggt ttgtgactcc aggagaacgg ccctcgggca tgttcgattc   4200
```

```
ctcggttctg tgcgagtgct atgacgcggg ctgtgcttgg tacgagctca cgcccgccga   4260
gacctcagtt aggttgcggg cttacctaaa cacaccaggg ttgcccgtct gccaggacca   4320
tctggagttc tgggagagcg tctttacagg cctcacccac atagacgccc atttcttgtc   4380
ccagactaag caggcaggag acaacttccc ctacctggta gcataccagg ctacggtgtg   4440
cgccagggct caggctccac ctccatcgtg ggaccaaatg tggaagtgtc tcatacggct   4500
aaagcctacg ctgcacgggc caacgcccct gctgtatagg ctgggagccg ttcaaaacga   4560
ggttactacc acacacccca taaccaaata catcatggca tgcatgtcgg ctgacctgga   4620
ggtcgtcacg agcacctggg tgctggtagg cggagtccta gcagctctgg ccgcgtattg   4680
cctgacaaca ggcagcgtgg tcattgtggg caggatcatc ttgtccggaa agccggccat   4740
cattcccgac agggaagtcc tttaccggga gttcgatgag atggaagagt gcgcctcaca   4800
cctcccttac atcgaacagg gaatgcagct cgccgaacaa ttcaaacaga aggcaatcgg   4860
gttgctgcaa acagccacca agcaagcgga ggctgctgct cccgtggtgg aatccaagtg   4920
gcggaccctc gaagccttct gggcgaagca tatgtggaat ttcatcagcg ggatacaata   4980
tttagcaggc ttgtccactc tgcctggcaa ccccgcgata gcatcactga tggcattcac   5040
agcctctatc accagcccgc tcaccaccca acataccctc ctgtttaaca tcctgggggg   5100
atgggtggcc gcccaacttg ctcctcccag cgctgcttct gctttcgtag gcgccggcat   5160
cgctggagcg gctgttggca gcataggcct tgggacggtg cttgtggata ttttggcagg   5220
ttatggagca ggggtggcag gcgcgctcgt ggcctttaag gtcatgagcg gcgagatgcc   5280
ctccaccgag gacctggtta acctactccc tgctatcctc tcccctggcg ccctagtcgt   5340
cggggtcgtg tgcgcagcga tactgcgtcg gcacgtgggc ccaggggagg gggctgtgca   5400
gtggatgaac cggctgatag cgttcgcttc gcggggtaac cacgtctccc ccacgcacta   5460
tgtgcctgag agcgacgctg cagcacgtgt cactcagatc ctctctagtc ttaccatcac   5520
tcagctgctg aagaggcttc accagtggat caacgaggac tgctccacgc catgctccgg   5580
ctcgtggcta agagatgttt gggattggat atgcacggtg ttgactgatt tcaagacctg   5640
gctccagtcc aagctcctgc cgcgattgcc gggagtcccc ttcttctcat gtcaacgtgg   5700
gtacaaggga gtctggcggg gcgacggcat catgcaaacc acctgcccat gtggagcaca   5760
gatcaccgga catgtgaaaa acggttccat gaggatcgtg gggcctagga cctgtagtaa   5820
cacgtggcat ggaacattcc ccattaacgc gtacaccacg ggcccctgca cgccctcccc   5880
ggcgccaaat tattctaggg cgctgtggcg ggtggctgct gaggagtacg tggaggttac   5940
gcgggtgggg gatttccact acgtgacggg catgaccact gacaacgtaa agtgcccgtg   6000
tcaggttccg gcccccgaat tcttcacaga agtggatggg gtgcggttgc acaggtacgc   6060
tccagcgtgc aaacccctcc tacgggagga ggtcacattc ctggtcgggc tcaatcaata   6120
cctggttggg tcacagctcc catgcgagcc cgaaccggac gtagcagtgc tcacttccat   6180
gctcaccgac ccctcccaca ttacggcgga gacggctaag cgtaggctgg ccaggggatc   6240
tcccccctcc ttggccagct catcagctag ccagctgtct gcgccttcct tgaaggcaac   6300
atgcactacc cgtcatgact ccccggacgc tgacctcatc gaggccaacc tcctgtggcg   6360
gcaggagatg ggcgggaaca tcacccgcgt ggagtcagaa aataaggtag taattttgga   6420
ctctttcgag ccgctccaag cggaggagga tgagagggaa gtatccgttc cggcggagat   6480
cctgcggagg tccaggaaat tccctcgagc gatgcccata tgggcacgcc cggattacaa   6540
ccctccactg ttagagtcct ggaaggaccc ggactacgtc cctccagtgg tacacgggtg   6600
```

```
tccattgccg cctgccaagg cccctccgat accacctcca cggaggaaga ggacggttgt   6660
cctgtcagaa tctaccgtgt cttctgcctt ggcggagctc gccacaaaga ccttcggcag   6720
ctccgaatcg tcggccgtcg acagcggcac ggcaacggcc tctcctgacc agccctccga   6780
cgacggcgac gcgggatccg acgttgagtc gtactcctcc atgccccccc ttgaggggga   6840
gccgggggat cccgatctca gcgacgggtc ttggtctacc gtaagcgagg aggctagtga   6900
ggacgtcgtc tgctgctcga tgtcctacac atggacaggc gccctgatca cgccatgcgc   6960
tgcggaggaa accaagctgc ccatcaatgc actgagcaac tctttgctcc gtcaccacaa   7020
cttggtctat gctacaacat ctcgcagcgc aagcctgcgg cagaagaagg tcacctttga   7080
cagactgcag gtcctggacg accactaccg ggacgtgctc aaggagatga aggcgaaggc   7140
gtccacagtt aaggctaaac ttctatccgt ggaggaagcc tgtaagctga cgcccccaca   7200
ttcggccaga tctaaatttg gctatggggc aaaggacgtc cggaacctat ccagcaaggc   7260
cgttaaccac atccgctccg tgtggaagga cttgctggaa gacactgaga caccaattga   7320
caccaccatc atggcaaaaa atgaggtttt ctgcgtccaa ccagagaagg ggggccgcaa   7380
gccagctcgc cttatcgtat tcccagattt gggggttcgt gtgtgcgaga aaatggccct   7440
ttacgatgtg gtctccaccc tccctcaggc cgtgatgggc tcttcatacg gattccaata   7500
ctctcctgga cagcgggtcg agttcctggt gaatgcctgg aaagcgaaga aatgccctat   7560
gggcttcgca tatgacaccc gctgttttga ctcaacggtc actgagaatg acatccgtgt   7620
tgaggagtca atctaccaat gttgtgactt ggcccccgaa gccagacagg ccataaggtc   7680
gctcacagag cggctttaca tcgggggccc cctgactaat tctaaagggc agaactgcgg   7740
ctatcgccgg tgccgcgcga gcggtgtact gacgaccagc tgcggtaata ccctcacatg   7800
ttacttgaag gccgctgcgg cctgtcgagc tgcgaagctc caggactgca cgatgctcgt   7860
atgcggagac gaccttgtcg ttatctgtga aagcgcgggg acccaagagg acgaggcgag   7920
cctacgggcc ttcacggagg ctatgactag atactctgcc ccccctgggg acccgcccaa   7980
accagaatac gacttggagt tgataacatc atgctcctcc aatgtgtcag tcgcgcacga   8040
tgcatctggc aaaagggtgt actatctcac ccgtgacccc accacccccc ttgcgcgggc   8100
tgcgtgggag acagctagac acactccagt caattcctgg ctaggcaaca tcatcatgta   8160
tgcgcccacc ttgtgggcaa ggatgatcct gatgactcat ttcttctcca tccttctagc   8220
tcaggaacaa cttgaaaaag ccctagattg tcagatctac ggggcctgtt actccattga   8280
gccacttgac ctacctcaga tcattcaacg actccatggc cttagcgcat tttcactcca   8340
tagttactct ccaggtgaga tcaatagggt ggcttcatgc ctcaggaaac ttggggtacc   8400
gcccttgcga gtctggagac atcgggccag aagtgtccgc gctaggctac tgtcccaggg   8460
ggggagggct gccacttgtg gcaagtacct cttcaactgg gcagtaagga ccaagctcaa   8520
actcactcca atcccggctg cgtcccagtt ggatttatcc agctggttcg ttgctggtta   8580
cagcggggga gacatatatc acagcctgtc tcgtgcccga ccccgctggt tcatgtggtg   8640
cctactccta ctttctgtag ggtaggcat ctatctactc cccaaccgat gaacggggag    8700
ctaaacactc caggccaata ggccatcctg ttttttccc tttttttttt tctttttttt    8760
tttttttttt tttttttttt ttttttctcc ttttttttc ctcttttttt cctttcttt    8820
cctttggtgg ctccatctta gccctagtca cggctagctg tgaaaggtcc gtgagccgct   8880
tgactgcaga gagtgctgat actggcctct ctgcagatca agtactacta gtccctttag   8940
```

-continued

```
tgagggttaa ttcaattctt gaagacgaaa gggcctcgtg atacgcctat ttttataggt   9000
taatgtcatg ataataatgg tttcttagac gtcaggtggc acttttcggg gaaatgtgcg   9060
cggaacccct atttgtttat ttttctaaat acattcaaat atgtatccgc tcatgagaca   9120
ataaccctga taaatgcttc aataatattg aaaaaggaag agtatgagta ttcaacattt   9180
ccgtgtcgcc cttattccct tttttgcggc attttgcctt cctgtttttg ctcacccaga   9240
aacgctggtg aaagtaaaag atgctgaaga tcagttgggt gcacgagtgg gttacatcga   9300
actggatctc aacagcggta agatccttga gagttttcgc cccgaagaac gttttccaat   9360
gatgagcact tttaaagttc tgctatgtgg cgcggtatta tcccgtgttg acgccgggca   9420
agagcaactc ggtcgccgca tacactattc tcagaatgac ttggttgagt actcaccagt   9480
cacagaaaag catcttacgg atggcatgac agtaagagaa ttatgcagtg ctgccataac   9540
catgagtgat aacactgcgg ccaacttact tctgacaacg atcggaggac cgaaggagct   9600
aaccgctttt ttgcacaaca tgggggatca tgtaactcgc cttgatcgtt gggaaccgga   9660
gctgaatgaa gccataccaa acgacgagcg tgacaccacg atgcctgcag caatggcaac   9720
aacgttgcgc aaactattaa ctggcgaact acttactcta gcttcccggc aacaattaat   9780
agactggatg gaggcggata aagttgcagg accacttctg cgctcggccc ttccggctgg   9840
ctggtttatt gctgataaat ctggagccgg tgagcgtggg tctcgcggta tcattgcagc   9900
actggggcca gatggtaagc cctcccgtat cgtagttatc tacacgacgg ggagtcaggc   9960
aactatggat gaacgaaata gacagatcgc tgagataggt gcctcactga ttaagcattg  10020
gtaactgtca gaccaagttt actcatatat actttagatt gatttaaaac ttcattttta  10080
atttaaaagg atctaggtga agatcctttt tgataatctc atgaccaaaa tcccttaacg  10140
tgagttttcg ttccactgag cgtcagaccc cgtagaaaag atcaaaggat cttcttgaga  10200
tccttttttt ctgcgcgtaa tctgctgctt gcaaacaaaa aaaccaccgc taccagcggt  10260
ggtttgtttg ccggatcaag agctaccaac tctttttccg aaggtaactg gcttcagcag  10320
agcgcagata ccaaatactg tccttctagt gtagccgtag ttaggccacc acttcaagaa  10380
ctctgtagca ccgcctacat acctcgctct gctaatcctg ttaccagtgg ctgctgccag  10440
tggcgataag tcgtgtctta ccgggttgga ctcaagacga tagttaccgg ataaggcgca  10500
gcggtcgggc tgaacggggg gttcgtgcac acagcccagc ttggagcgaa cgacctacac  10560
cgaactgaga tacctacagc gtgagctatg agaaagcgcc acgcttcccg aagggagaaa  10620
ggcggacagg tatccggtaa gcggcagggc ggaacaggag agcgcacgag ggagcttcca  10680
gggggaaacg cctggtatct ttatagtcct gtcgggtttc gccacctctg acttgagcgt  10740
cgatttttgt gatgctcgtc aggggggcgg agcctatgga aaaacgccag caacgcggcc  10800
tttttacggt tcctggcctt ttgctggcct tttgctcaca tgttctttcc tgcgttatcc  10860
cctgattctg tggataaccg tattaccgcc tttgagtgag ctgataccgc tcgccgcagc  10920
cgaacgaccg agcgcagcga gtcagtgagc gaggaagcgg aagagcgcct gatgcggtat  10980
tttctcctta cgcatctgtg cggtatttca caccgcatat ggtgcactct cagtacaatc  11040
tgctctgatg ccgcatagtt aagccagtat acactccgct atcgctacgt gactgggtca  11100
tggctgcgcc ccgacacccg ccaacacccg ctgacgcgcc ctgacgggct tgtctgctcc  11160
cggcatccgc ttacagacaa gctgtgaccg tctccgggag ctgcatgtgt cagaggtttt  11220
caccgtcatc accgaaacgc gcgaggcagc tgcggtaaag ctcatcagcg tggtcgtgaa  11280
gcgattcaca gatgtctgcc tgttcatccg cgtccagctc gttgagtttc tccagaagcg  11340
```

ttaatgtctg gcttctgata aagcgggcca tgttaagggc ggttttttcc tgtttggtca 11400
ctgatgcctc cgtgtaaggg ggatttctgt tcatgggggt aatgataccg atgaaacgag 11460
agaggatgct cacgatacgg gttactgatg atgaacatgc ccggttactg gaacgttgtg 11520
agggtaaaca actggcggta tggatgcggc gggaccagag aaaaatcact cagggtcaat 11580
gccagcgctt cgttaataca gatgtaggtg ttccacaggg tagccagcag catcctgcga 11640
tgcagatccg gaacataatg gtgcagggcg ctgacttccg cgtttccaga ctttacgaaa 11700
cacggaaacc gaagaccatt catgttgttg ctcaggtcgc agacgttttg cagcagcagt 11760
cgcttcacgt tcgctcgcgt atcggtgatt cattctgcta accagtaagg caaccccgcc 11820
agcctagccg ggtcctcaac gacaggagca cgatcatgcg cacccgtggc caggacccaa 11880
cgctgcccga gatgcgccgc gtgcggctgc tggagatggc ggacgcgatg gatatgttct 11940
gccaagctaa gctgcctgca ggtaatacga ctcactatag ccagcccccg attgggggcg 12000
aca 12003

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
atggcgccta ttaccgccta ctcccaacag acg 33

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
aatgtctgcg gtaccgccgg gggggatgag ttgtc 35

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
tagagtcctg gaaggacccg g 21

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
ggcctggagt ggttagctcc cc 22

<210> SEQ ID NO 15

<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
tggaaggacc cggactacg 19

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
gagtggttag ctccccgttc a 21

<210> SEQ ID NO 17
<211> LENGTH: 12573
<212> TYPE: DNA
<213> ORGANISM: Hepatitis C virus

<400> SEQUENCE: 17
gccagccccc gattgggggc gacactccac catagatcac tcccctgtga ggaactactg 60
tcttcacgca gaaagcgtct agccatggcg ttagtatgag tgtcgtgcag cctccaggac 120 ccccccctccc gggagagcca tagtggtctg cggaaccggt gagtacaccg gaattgccag 180
gacgaccggg tcctttcttg gatcaacccg ctcaatgcct ggagatttgg gcgtgccccc 240
gcgagactgc tagccgagta gtgttgggtc gcgaaaggcc ttgtggtact gcctgatagg 300
gtgcttgcga gtgccccggg aggtctcgta gaccgtgcac cgtttaaacc cccgtgctgc 360
tggaagtcga tttcaggctt agggtaaccg tggacctcga aaacagacgc acaaaaccaa 420
gttcaataga agggggtaca aaccagtacc accacgaaca agcacttctg tttccccggt 480
gatgtcgtat agactgcttg cgtggttgaa agcgacggat ccgttatccg cttatgtact 540
tcgagaagcc cagtaccacc tcggaatctt cgatgcgttg cgctcagcac tcaaccccag 600
agtgtagctt aggctgatga gtctggacat ccctcaccgg tgacggtggt ccaggctgcg 660
ttggcggcct acctatggct aacgccatgg gacgctagtt gtgaacaagg tgtgaagagc 720
ctattgagct acataagaat cctccggccc ctgaatgcgg ctaatcccaa cctcggagca 780
ggtggtcaca aaccagtgat tggcctgtcg taacgcgcaa gtccgtggcg gaaccgacta 840
ctttgggtgt ccgtgtttcc ttttatttta ttgtggctgc ttatggtgac aatcacagat 900
tgttatcata aagcgaattg gattggccat ccggtgaaag tgagactcat tatctatctg 960
tttgctggat ccgctccatt gagtgtgttt actctaagta caatttcaac agttatttca 1020
atcagacaat tgtatcataa tggcgggccc agaagacgcc aaaaacataa agaaaggccc 1080
ggcgccattc tatcctctag aggatggaac cgctggagag caactgcata aggctatgaa 1140
gagatacgcc ctggttcctg gaacaattgc ttttacagat gcacatatcg aggtgaacat 1200
cacgtacgcg gaatacttcg aaatgtccgt tcggttggca gaagctatga aacgatatgg 1260
gctgaataca aatcacagaa tcgtcgtatg cagtgaaaac tctcttcaat tctttatgcc 1320
ggtgttgggc gcgttattta tcggagttgc agttgcgccc gcgaacgaca tttataatga 1380
acgtgaattg ctcaacagta tgaacatttc gcagcctacc gtagtgtttg tttccaaaaa 1440

-continued

```
ggggttgcaa aaaattttga acgtgcaaaa aaaattacca ataatccaga aaattattat   1500
catggattct aaaacggatt accagggatt tcagtcgatg tacacgttcg tcacatctca   1560
tctacctccc ggttttaatg aatacgattt tgtaccagag tcctttgatc gtgacaaaac   1620
aattgcactg ataatgaatt cctctggatc tactgggtta cctaagggtg tggcccttcc   1680
gcatagaact gcctgcgtca gattctcgca tgccagagat cctatttttg gcaatcaaat   1740
cattccggat actgcgattt taagtgttgt tccattccat cacggttttg gaatgtttac   1800
tacactcgga tatttgatat gtggatttcg agtcgtctta atgtatagat ttgaagaaga   1860
gctgttttta cgatcccttc aggattacaa aattcaaagt gcgttgctag taccaaccct   1920
attttcattc ttcgccaaaa gcactctgat tgacaaatac gatttatcta atttacacga   1980
aattgcttct gggggcgcac ctctttcgaa agaagtcggg gaagcggttg caaaacgctt   2040
ccatcttcca gggatacgac aaggatatgg gctcactgag actacatcag ctattctgat   2100
tacacccgag ggggatgata aaccgggcgc ggtcggtaaa gttgttccat tttttgaagc   2160
gaaggttgtg gatctggata ccgggaaaac gctgggcgtt aatcagagag gcgaattatg   2220
tgtcagagga cctatgatta tgtccggtta tgtaaacaat ccggaagcga ccaacgcctt   2280
gattgacaag gatggatggc tacattctgg agacatagct tactgggacg aagacgaaca   2340
cttcttcata gttgaccgct tgaagtcttt aattaaatac aaaggatatc aggtggcccc   2400
cgctgaattg gaatcgatat tgttacaaca ccccaacatc ttcgacgcgg gcgtggcagg   2460
tcttcccgac gatgacgccg gtgaacttcc cgccgccgtt gttgttttgg agcacggaaa   2520
gacgatgacg gaaaaagaga tcgtggatta cgtcgccagt caagtaacaa ccgcgaaaaa   2580
gttgcgcgga ggagttgtgt ttgtggacga agtaccgaaa ggtcttaccg gaaaactcga   2640
cgcaagaaaa atcagagaga tcctcataaa ggccaagaag ggcggaaagt ccaaattgta   2700
agcggccgcg ttgttaaaca gaccacaacg gtttccctct agcgggatca attccgcccc   2760
ccccccctaa cgttactggc cgaagccgct tggaataagg ccggtgtgcg tttgtctata   2820
tgttattttc caccatattg ccgtcttttg gcaatgtgag ggcccggaaa cctggccctg   2880
tcttcttgac gagcattcct aggggtcttt cccctctcgc caaaggaatg caaggtctgt   2940
tgaatgtcgt gaaggaagca gttcctctgg aagcttcttg aagacaaaca acgtctgtag   3000
cgaccctttg caggcagcgg aaccccccac ctggcgacag gtgcctctgc ggccaaaagc   3060
cacgtgtata agatacacct gcaaaggcgg cacaacccca gtgccacgtt gtgagttgga   3120
tagttgtgga aagagtcaaa tggctctcct caagcgtatt caacaagggg ctgaaggatg   3180
cccagaaggt accccattgt atgggatctg atctggggcc tcggtgcaca tgctttacat   3240
gtgtttagtc gaggttaaaa aaacgtctag gccccccgaa ccacggggac gtggttttcc   3300
tttgaaaaac acgataatac catggcgcct attacggcct actcccaaca gacgcgaggc   3360
ctacttggct gcatcatcac tagcctcaca ggccgggaca ggaaccaggt cgagggggag   3420
gtccaagtgg tctccaccgc aacacaatct ttcctggcga cctgcgtcaa tggcgtgtgt   3480
tggactgtct atcatggtgc cggctcaaag acccttgccg gcccaaaggg cccaatcacc   3540
caaatgtaca ccaatgtgga ccaggacctc gtcggctggc aagcgccccc cggggcgcgt   3600
tccttgacac catgcacctg cggcagctcg gacctttact tggtcacgag gcatgccgat   3660
gtcattccgg tgcgccggcg gggcgacagc agggggagcc tactctcccc caggcccgtc   3720
tcctacttga agggctcttc gggcggtcca ctgctctgcc cctcggggca cgctgtgggc   3780
```

-continued

```
atctttcggg ctgccgtgtg cacccgaggg gttgcgaagg cggtggactt tgtacccgtc   3840
gagtctatgg gaaccactat gcggtccccg gtcttcacgg acaactcgtc ccctccggcc   3900
gtaccgcaga cattccaggt ggcccatcta cacgccccta ctggtagcgg caagagcact   3960
aaggtgccgg ctgcgtatgc agcccaaggg tataaggtgc ttgtcctgaa cccgtccgtc   4020
gccgccaccc taggtttcgg ggcgtatatg tctaaggcac atggtatcga ccctaacatc   4080
agaatcgggg taaggaccat caccacgggt gcccccatca cgtactccac ctatggcaag   4140
tttcttgccg acggtggttg ctctgggggc gcctatgaca tcataatatg tgatgagtgc   4200
cactcaactg actcgaccac tatcctgggc atcggcacag tcctggacca agcggagacg   4260
gctggagcgc gactcgtcgt gctcgccacc gctacgcctc cgggatcggt caccgtgcca   4320
catccaaaca tcgaggaggt ggctctgtcc agcactggag aaatcccctt ttatggcaaa   4380
gccatcccca tcgagaccat caaggggggg aggcacctca ttttctgcca ttccaagaag   4440
aaatgtgatg agctcgccgc gaagctgtcc ggcctcggac tcaatgctgt agcatattac   4500
cggggccttg atgtatccgt cataccaact agcggagacg tcattgtcgt agcaacggac   4560
gctctaatga cgggctttac cggcgatttc gactcagtga tcgactgcaa tacatgtgtc   4620
acccagacag tcgacttcag cctggacccg accttcacca ttgagacgac gaccgtgcca   4680
caagacgcgg tgtcacgctc gcagcggcga ggcaggactg gtaggggcag gatgggcatt   4740
tacaggtttg tgactccagg agaacggccc tcgggcatgt tcgattcctc ggttctgtgc   4800
gagtgctatg acgcgggctg tgcttggtac gagctcacgc ccgccgagac ctcagttagg   4860
ttgcgggctt acctaaacac accagggttg cccgtctgcc aggaccatct ggagttctgg   4920
gagagcgtct ttacaggcct cacccacata gacgcccatt tcttgtccca gactaagcag   4980
gcaggagaca acttccccta cctggtagca taccaggcta cggtgtgcgc cagggctcag   5040
gctccacctc catcgtggga ccaaatgtgg aagtgtctca tacggctaaa gcctacgctg   5100
cacgggccaa cgcccctgct gtataggctg ggagccgttc aaaacgaggt tactaccaca   5160
caccccataa ccaaatacat catggcatgc atgtcggctg acctggaggt cgtcacgagc   5220
acctgggtgc tggtaggcgg agtcctagca gctctggccg cgtattgcct gacaacaggc   5280
agcgtggtca ttgtgggcag gatcatcttg tccggaaagc cggccatcat tcccgacagg   5340
gaagtccttt accgggagtt cgatgagatg gaagagtgcg cctcacacct cccttacatc   5400
gaacagggaa tgcagctcgc cgaacaattc aaacagaagg caatcgggtt gctgcaaaca   5460
gccaccaagc aagcggaggc tgctgctccc gtggtggaat ccaagtggcg gaccctcgaa   5520
gccttctggg cgaagcatat gtggaatttc atcagcggga tacaatattt agcaggcttg   5580
tccactctgc ctggcaaccc cgcgatagca tcactgatgg cattcacagc ctctatcacc   5640
agcccgctca ccacccaaca taccctcctg tttaacatcc tgggggggatg ggtggccgcc   5700
caacttgctc ctcccagcgc tgcttctgct ttcgtaggcg ccggcatcgc tggagcggct   5760
gttggcagca taggccttgg gacggtgctt gtggatattt tggcaggtta tggagcaggg   5820
gtggcaggcg cgctcgtggc ctttaaggtc atgagcggcg agatgccctc caccgaggac   5880
ctggttaacc tactccctgc tatcctctcc cctggcgccc tagtcgtcgg ggtcgtgtgc   5940
gcagcgatac tgcgtcggca cgtgggccca ggggaggggg ctgtgcagtg gatgaaccgg   6000
ctgatagcgt tcgcttcgcg ggtaaccac gtctcccccca cgcactatgt gcctgagagc   6060
gacgctgcag cacgtgtcac tcagatcctc tctagtctta ccatcactca gctgctgaag   6120
aggcttcacc agtggatcaa cgaggactgc tccacgccat gctccggctc gtggctaaga   6180
```

-continued

```
gatgtttggg attggatatg cacggtgttg actgatttca agacctggct ccagtccaag   6240
ctcctgccgc gattgccggg agtccccttc ttctcatgtc aacgtgggta caagggagtc   6300
tggcggggcg acggcatcat gcaaaccacc tgcccatgtg gagcacagat caccggacat   6360
gtgaaaaacg gttccatgag gatcgtgggg cctaggacct gtagtaacac gtggcatgga   6420
acattcccca ttaacgcgta caccacgggc ccctgcacgc cctccccggc gccaaattat   6480
tctagggcgc tgtggcgggt ggctgctgag gagtacgtgg aggttacgcg ggtgggggat   6540
ttccactacg tgacgggcat gaccactgac aacgtaaagt gcccgtgtca ggttccggcc   6600
cccgaattct tcacagaagt ggatggggtg cggttgcaca ggtacgctcc agcgtgcaaa   6660
cccctcctac gggaggaggt cacattcctg gtcgggctca atcaatacct ggttgggtca   6720
cagctcccat gcgagcccga accggacgta gcagtgctca cttccatgct caccgacccc   6780
tcccacatta cggcggagac ggctaagcgt aggctggcca ggggatctcc cccctccttg   6840
gccagctcat cagctagcca gctgtctgcg ccttccttga aggcaacatg cactacccgt   6900
catgactccc cggacgctga cctcatcgag gccaacctcc tgtggcggca ggagatgggc   6960
gggaacatca cccgcgtgga gtcagaaaat aaggtagtaa ttttggactc tttcgagccg   7020
ctccaagcgg aggaggatga gagggaagta tccgttccgg cggagatcct gcggaggtcc   7080
aggaaattcc ctcgagcgat gcccatatgg gcacgcccgg attacaaccc tccactgtta   7140
gagtcctgga aggacccgga ctacgtccct ccagtggtac acgggtgtcc attgccgcct   7200
gccaaggccc ctccgatacc acctccacgg aggaagagga cggttgtcct gtcagaatct   7260
accgtgtctt ctgccttggc ggagctcgcc acaaagacct tcggcagctc cgaatcgtcg   7320
gccgtcgaca gcggcacggc aacggcctct cctgaccagc cctccgacga cggcgacgcg   7380
ggatccgacg ttgagtcgta ctcctccatg cccccccttg aggggggagcc gggggatccc   7440
gatctcagcg acgggtcttg gtctaccgta agcgaggagg ctagtgagga cgtcgtctgc   7500
tgctcgatgt cctacacatg gacaggcgcc ctgatcacgc catgcgctgc ggaggaaacc   7560
aagctgccca tcaatgcact gagcaactct ttgctccgtc accacaactt ggtctatgct   7620
acaacatctc gcagcgcaag cctgcggcag aagaaggtca cctttgacag actgcaggtc   7680
ctggacgacc actaccggga cgtgctcaag gagatgaagg cgaaggcgtc cacagttaag   7740
gctaaacttc tatccgtgga ggaagcctgt aagctgacgc ccccacattc ggccagatct   7800
aaatttggct atggggcaaa ggacgtccgg aacctatcca gcaaggccgt taaccacatc   7860
cgctccgtgt ggaaggactt gctggaagac actgagacac caattgacac caccatcatg   7920
gcaaaaaatg aggttttctg cgtccaacca gagaaggggg gccgcaagcc agctcgcctt   7980
atcgtattcc cagatttggg ggttcgtgtg tgcgagaaaa tggcccttta cgatgtggtc   8040
tccaccctcc ctcaggccgt gatgggctct tcatacggat tccaatactc tcctggacag   8100
cgggtcgagt tcctggtgaa tgcctggaaa gcgaagaaat gccctatggg cttcgcatat   8160
gacacccgct gttttgactc aacggtcact gagaatgaca tccgtgttga ggagtcaatc   8220
taccaatgtt gtgacttggc ccccgaagcc agacaggcca taaggtcgct cacagagcgg   8280
ctttacatcg ggggccccct gactaattct aaagggcaga actgcggcta tcgccggtgc   8340
cgcgcgagcg gtgtactgac gaccagctgc ggtaataccc tcacatgtta cttgaaggcc   8400
gctgcggcct gtcgagctgc gaagctccag gactgcacga tgctcgtatg cggagacgac   8460
cttgtcgtta tctgtgaaag cgcggggacc caagaggacg aggcgagcct acgggccttc   8520
```

acggaggcta tgactagata ctctgccccc cctggggacc cgcccaaacc agaatacgac 8580
ttggagttga taacatcatg ctcctccaat gtgtcagtcg cgcacgatgc atctggcaaa 8640
agggtgtact atctcacccg tgaccccacc acccccccttg cgcgggctgc gtgggagaca 8700
gctagacaca ctccagtcaa ttcctggcta ggcaacatca tcatgtatgc gcccaccttg 8760
tgggcaagga tgatcctgat gactcatttc ttctccatcc ttctagctca ggaacaactt 8820
gaaaaagccc tagattgtca gatctacggg gcctgttact ccattgagcc acttgaccta 8880
cctcagatca ttcaacgact ccatggcctt agcgcatttt cactccatag ttactctcca 8940
ggtgagatca atagggtggc ttcatgcctc aggaaacttg gggtaccgcc cttgcgagtc 9000
tggagacatc gggccagaag tgtccgcgct aggctactgt cccagggggg gagggctgcc 9060
acttgtggca agtacctctt caactgggca gtaaggacca agctcaaact cactccaatc 9120
ccggctgcgt cccagttgga tttatccagc tggttcgttg ctggttacag cgggggagac 9180
atatatcaca gcctgtctcg tgcccgaccc cgctggttca tgtggtgcct actcctactt 9240
tctgtagggg taggcatcta tctactcccc aaccgatgac ttaagacggg gagctaaaca 9300
ctccaggcca ataggccatc ctgttttttt cccttttttt ttttcttttt tttttttttt 9360
tttttttttt tttttttttc tcctttttttt ttcctctttt tttccttttc tttcctttgg 9420
tggctccatc ttagccctag tcacggctag ctgtgaaagg tccgtgagcc gcttgactgc 9480
agagagtgct gatactggcc tctctgcaga tcaagtacta ctagtccctt tagtgagggt 9540
taattcaatt cttgaagacg aaagggcctc gtgatacgcc tatttttata ggttaatgtc 9600
atgataataa tggtttctta gacgtcaggt ggcacttttc ggggaaatgt gcgcggaacc 9660
cctatttgtt tatttttcta aatacattca aatatgtatc cgctcatgag acaataaccc 9720
tgataaatgc ttcaataata ttgaaaaagg aagagtatga gtattcaaca tttccgtgtc 9780
gcccttattc ccttttttgc ggcattttgc cttcctgttt ttgctcaccc agaaacgctg 9840
gtgaaagtaa aagatgctga agatcagttg ggtgcacgag tgggttacat cgaactggat 9900
ctcaacagcg gtaagatcct tgagagtttt cgccccgaag aacgttttcc aatgatgagc 9960
acttttaaag ttctgctatg tggcgcggta ttatcccgtg ttgacgccgg gcaagagcaa 10020
ctcggtcgcc gcatacacta ttctcagaat gacttggttg agtactcacc agtcacagaa 10080
aagcatctta cggatggcat gacagtaaga gaattatgca gtgctgccat aaccatgagt 10140
gataacactg cggccaactt acttctgaca acgatcggag gaccgaagga gctaaccgct 10200
tttttgcaca acatggggga tcatgtaact cgccttgatc gttgggaacc ggagctgaat 10260
gaagccatac caaacgacga gcgtgacacc acgatgcctg cagcaatggc aacaacgttg 10320
cgcaaactat taactggcga actacttact ctagcttccc ggcaacaatt aatagactgg 10380
atggaggcgg ataaagttgc aggaccactt ctgcgctcgg cccttccggc tggctggttt 10440
attgctgata aatctggagc cggtgagcgt gggtctcgcg gtatcattgc agcactgggg 10500
ccagatggta agccctcccg tatcgtagtt atctacacga cggggagtca ggcaactatg 10560
gatgaacgaa atagacagat cgctgagata ggtgcctcac tgattaagca ttggtaactg 10620
tcagaccaag tttactcata tatactttag attgatttaa aacttcattt ttaatttaaa 10680
aggatctagg tgaagatcct ttttgataat ctcatgacca aaatccctta acgtgagttt 10740
tcgttccact gagcgtcaga ccccgtagaa aagatcaaag gatcttcttg agatcctttt 10800
tttctgcgcg taatctgctg cttgcaaaca aaaaaaccac cgctaccagc ggtggtttgt 10860
ttgccggatc aagagctacc aactcttttt ccgaaggtaa ctggcttcag cagagcgcag 10920
ataccaaata ctgtccttct agtgtagccg tagttaggcc accacttcaa gaactctgta 10980
gcaccgccta catacctcgc tctgctaatc ctgttaccag tggctgctgc cagtggcgat 11040
aagtcgtgtc ttaccgggtt ggactcaaga cgatagttac cggataaggc gcagcggtcg 11100
ggctgaacgg ggggttcgtg cacacagccc agcttggagc gaacgaccta caccgaactg 11160
agatacctac agcgtgagct atgagaaagc gccacgcttc ccgaagggag aaaggcggac 11220
aggtatccgg taagcggcag ggtcggaaca ggagagcgca cgagggagct tccaggggga 11280
aacgcctggt atctttatag tcctgtcggg tttcgccacc tctgacttga gcgtcgattt 11340
ttgtgatgct cgtcaggggg gcggagccta tggaaaaacg ccagcaacgc ggccttttta 11400
cggttcctgg ccttttgctg gccttttgct cacatgttct ttcctgcgtt atcccctgat 11460
tctgtggata accgtattac cgcctttgag tgagctgata ccgctcgccg cagccgaacg 11520
accgagcgca gcgagtcagt gagcgaggaa gcggaagagc gcctgatgcg gtattttctc 11580
cttacgcatc tgtgcggtat ttcacaccgc atatggtgca ctctcagtac aatctgctct 11640
gatgccgcat agttaagcca gtatacactc cgctatcgct acgtgactgg gtcatggctg 11700
cgccccgaca cccgccaaca cccgctgacg cgccctgacg ggcttgtctg ctcccggcat 11760
ccgcttacag acaagctgtg accgtctccg ggagctgcat gtgtcagagg ttttcaccgt 11820
catcaccgaa acgcgcgagg cagctgcggt aaagctcatc agcgtggtcg tgaagcgatt 11880
cacagatgtc tgcctgttca tccgcgtcca gctcgttgag tttctccaga agcgttaatg 11940
tctggcttct gataaagcgg gccatgttaa gggcggtttt ttcctgtttg gtcactgatg 12000
cctccgtgta agggggattt ctgttcatgg gggtaatgat accgatgaaa cgagagagga 12060
tgctcacgat acgggttact gatgatgaac atgcccggtt actggaacgt tgtgagggta 12120
aacaactggc ggtatggatg cggcgggacc agagaaaaat cactcagggt caatgccagc 12180
gcttcgttaa tacagatgta ggtgttccac agggtagcca gcagcatcct gcgatgcaga 12240
tccggaacat aatggtgcag ggcgctgact tccgcgtttc cagactttac gaaacacgga 12300
aaccgaagac cattcatgtt gttgctcagg tcgcagacgt tttgcagcag cagtcgcttc 12360
acgttcgctc gcgtatcggt gattcattct gctaaccagt aaggcaaccc cgccagccta 12420
gccgggtcct caacgacagg agcacgatca tgcgcacccg tggccaggac ccaacgctgc 12480
ccgagatgcg ccgcgtgcgg ctgctggaga tggcggacgc gatggatatg ttctgccaag 12540
ctaagctgcc tgcaggtaat acgactcact ata 12573

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
accgtaagcg aggagcttaa ggctagtgag gacgtc 36

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
gacgtcctca ctagccttaa gctcctcgct tacggt 36

<210> SEQ ID NO 20
<211> LENGTH: 12579
<212> TYPE: DNA
<213> ORGANISM: Hepatitis C virus

<400> SEQUENCE: 20
gccagccccc gattgggggc gacactccac catagatcac tcccctgtga ggaactactg 60
tcttcacgca gaaagcgtct agccatggcg ttagtatgag tgtcgtgcag cctccaggac 120
ccccctcccc gggagagcca tagtggtctg cggaaccggt gagtacaccg gaattgccag 180
gacgaccggg tcctttcttg gatcaacccg ctcaatgcct ggagatttgg gcgtgccccc 240
gcgagactgc tagccgagta gtgttgggtc gcgaaaggcc ttgtggtact gcctgatagg 300
gtgcttgcga gtgccccggg aggtctcgta gaccgtgcac cgtttaaacc cccgtgctgc 360
tggaagtcga tttcaggctt agggtaaccg tggacctcga aacagacgc acaaaaaccaa 420 gttcaataga agggggtaca aaccagtacc accacgaaca agcacttctg tttccccggt 480
gatgtcgtat agactgcttg cgtggttgaa agcgacggat ccgttatccg cttatgtact 540
tcgagaagcc cagtaccacc tcggaatctt cgatgcgttg cgctcagcac tcaaccccag 600
agtgtagctt aggctgatga gtctggacat ccctcaccgg tgacggtggt ccaggctgcg 660
ttggcggcct acctatggct aacgccatgg gacgctagtt gtgaacaagg tgtgaagagc 720
ctattgagct acataagaat cctccggccc ctgaatgcgg ctaatcccaa cctcggagca 780
ggtggtcaca aaccagtgat tggcctgtcg taacgcgcaa gtccgtggcg gaaccgacta 840
ctttgggtgt ccgtgtttcc ttttatttta ttgtggctgc ttatggtgac aatcacagat 900
tgttatcata aagcgaattg gattggccat ccggtgaaag tgagactcat tatctatctg 960
tttgctggat ccgctccatt gagtgtgttt actctaagta caatttcaac agttatttca 1020
atcagacaat tgtatcataa tggcgggccc agaagacgcc aaaaacataa agaaaggccc 1080
ggcgccattc tatcctctag aggatggaac cgctggagag caactgcata aggctatgaa 1140
gagatacgcc ctggttcctg gaacaattgc ttttacagat gcacatatcg aggtgaacat 1200
cacgtacgcg gaatacttcg aaatgtccgt tcggttggca gaagctatga aacgatatgg 1260
gctgaataca aatcacagaa tcgtcgtatg cagtgaaaac tctcttcaat tctttatgcc 1320
ggtgttgggc gcgttattta tcggagttgc agttgcgccc gcgaacgaca tttataatga 1380
acgtgaattg ctcaacagta tgaacatttc gcagcctacc gtagtgtttg tttccaaaaa 1440
ggggttgcaa aaaattttga acgtgcaaaa aaaattacca ataatccaga aaattattat 1500
catggattct aaaacggatt accagggatt tcagtcgatg tacacgttcg tcacatctca 1560
tctacctccc ggttttaatg aatacgattt tgtaccagag tcctttgatc gtgacaaaac 1620
aattgcactg ataatgaatt cctctggatc tactgggtta cctaagggtg tggcccttcc 1680
gcatagaact gcctgcgtca gattctcgca tgccagagat cctatttttg gcaatcaaat 1740
cattccggat actgcgattt taagtgttgt tccattccat cacggttttg gaatgtttac 1800
tacactcgga tatttgatat gtggatttcg agtcgtctta atgtatagat ttgaagaaga 1860
gctgttttta cgatcccttc aggattacaa aattcaaagt gcgttgctag taccaaccct 1920
attttcattc ttcgccaaaa gcactctgat tgacaaatac gatttatcta atttacacga 1980
aattgcttct gggggcgcac ctctttcgaa agaagtcggg gaagcggttg caaaacgctt 2040

-continued

```
ccatcttcca gggatacgac aaggatatgg gctcactgag actacatcag ctattctgat   2100
tacacccgag ggggatgata aaccgggcgc ggtcggtaaa gttgttccat tttttgaagc   2160
gaaggttgtg gatctggata ccgggaaaac gctgggcgtt aatcagagag gcgaattatg   2220
tgtcagagga cctatgatta tgtccggtta tgtaaacaat ccggaagcga ccaacgcctt   2280
gattgacaag gatggatggc tacattctgg agacatagct tactgggacg aagacgaaca   2340
cttcttcata gttgaccgct tgaagtcttt aattaaatac aaaggatatc aggtggcccc   2400
cgctgaattg gaatcgatat tgttacaaca ccccaacatc ttcgacgcgg gcgtggcagg   2460
tcttcccgac gatgacgccg gtgaacttcc cgccgccgtt gttgttttgg agcacggaaa   2520
gacgatgacg gaaaaagaga tcgtggatta cgtcgccagt caagtaacaa ccgcgaaaaa   2580
gttgcgcgga ggagttgtgt ttgtggacga agtaccgaaa ggtcttaccg gaaaactcga   2640
cgcaagaaaa atcagagaga tcctcataaa ggccaagaag ggcggaaagt ccaaattgta   2700
agcggccgcg ttgttaaaca gaccacaacg gtttccctct agcgggatca attccgcccc   2760
ccccccctaa cgttactggc cgaagccgct tggaataagg ccggtgtgcg tttgtctata   2820
tgttattttc caccatattg ccgtcttttg gcaatgtgag ggcccggaaa cctggccctg   2880
tcttcttgac gagcattcct aggggtcttt cccctctcgc caaaggaatg caaggtctgt   2940
tgaatgtcgt gaaggaagca gttcctctgg aagcttcttg aagacaaaca acgtctgtag   3000
cgaccctttg caggcagcgg aaccccccac ctggcgacag gtgcctctgc ggccaaaagc   3060
cacgtgtata agatacacct gcaaaggcgg cacaacccca gtgccacgtt gtgagttgga   3120
tagttgtgga aagagtcaaa tggctctcct caagcgtatt caacaagggg ctgaaggatg   3180
cccagaaggt accccattgt atgggatctg atctggggcc tcggtgcaca tgctttacat   3240
gtgtttagtc gaggttaaaa aaacgtctag gccccccgaa ccacggggac gtggttttcc   3300
tttgaaaaac acgataatac catggcgcct attacggcct actcccaaca gacgcgaggc   3360
ctacttggct gcatcatcac tagcctcaca ggccgggaca ggaaccaggt cgagggggag   3420
gtccaagtgg tctccaccgc aacacaatct ttcctggcga cctgcgtcaa tggcgtgtgt   3480
tggactgtct atcatggtgc cggctcaaag acccttgccg gcccaaaggg cccaatcacc   3540
caaatgtaca ccaatgtgga ccaggacctc gtcggctggc aagcgccccc cggggcgcgt   3600
tccttgacac catgcacctg cggcagctcg gacctttact tggtcacgag gcatgccgat   3660
gtcattccgg tgcgccggcg gggcgacagc agggggagcc tactctcccc caggcccgtc   3720
tcctacttga agggctcttc gggcggtcca ctgctctgcc cctcggggca cgctgtgggc   3780
atctttcggg ctgccgtgtg cacccgaggg gttgcgaagg cggtggactt tgtacccgtc   3840
gagtctatgg gaaccactat gcggtccccg gtcttcacgg acaactcgtc ccctccggcc   3900
gtaccgcaga cattccaggt ggcccatcta cacgccccta ctggtagcgg caagagcact   3960
aaggtgccgg ctgcgtatgc agcccaaggg tataaggtgc ttgtcctgaa cccgtccgtc   4020
gccgccaccc taggtttcgg ggcgtatatg tctaaggcac atggtatcga ccctaacatc   4080
agaatcgggg taaggaccat caccacgggt gcccccatca cgtactccac ctatggcaag   4140
tttcttgccg acggtggttg ctctgggggc gcctatgaca tcataatatg tgatgagtgc   4200
cactcaactg actcgaccac tatcctgggc atcggcacag tcctggacca agcggagacg   4260
gctggagcgc gactcgtcgt gctcgccacc gctacgcctc cgggatcggt caccgtgcca   4320
catccaaaca tcgaggaggt ggctctgtcc agcactggag aaatcccctt ttatggcaaa   4380
```

-continued

```
gccatcccca tcgagaccat caaggggggg aggcacctca ttttctgcca ttccaagaag   4440
aaatgtgatg agctcgccgc gaagctgtcc ggcctcggac tcaatgctgt agcatattac   4500
cggggccttg atgtatccgt cataccaact agcggagacg tcattgtcgt agcaacggac   4560
gctctaatga cgggctttac cggcgatttc gactcagtga tcgactgcaa tacatgtgtc   4620
acccagacag tcgacttcag cctggacccg accttcacca ttgagacgac gaccgtgcca   4680
caagacgcgg tgtcacgctc gcagcggcga ggcaggactg gtaggggcag gatgggcatt   4740
tacaggtttg tgactccagg agaacggccc tcgggcatgt tcgattcctc ggttctgtgc   4800
gagtgctatg acgcgggctg tgcttggtac gagctcacgc ccgccgagac ctcagttagg   4860
ttgcgggctt acctaaacac accagggttg cccgtctgcc aggaccatct ggagttctgg   4920
gagagcgtct ttacaggcct cacccacata gacgcccatt tcttgtccca gactaagcag   4980
gcaggagaca acttccccta cctggtagca taccaggcta cggtgtgcgc cagggctcag   5040
gctccacctc catcgtggga ccaaatgtgg aagtgtctca tacggctaaa gcctacgctg   5100
cacgggccaa cgcccctgct gtataggctg ggagccgttc aaaacgaggt tactaccaca   5160
caccccataa ccaaatacat catggcatgc atgtcggctg acctggaggt cgtcacgagc   5220
acctgggtgc tggtaggcgg agtcctagca gctctggccg cgtattgcct gacaacaggc   5280
agcgtggtca ttgtgggcag gatcatcttg tccggaaagc cggccatcat tcccgacagg   5340
gaagtccttt accgggagtt cgatgagatg gaagagtgcg cctcacacct cccttacatc   5400
gaacagggaa tgcagctcgc cgaacaattc aaacagaagg caatcgggtt gctgcaaaca   5460
gccaccaagc aagcggaggc tgctgctccc gtggtggaat ccaagtggcg gaccctcgaa   5520
gccttctggg cgaagcatat gtggaatttc atcagcggga tacaatattt agcaggcttg   5580
tccactctgc ctggcaaccc cgcgatagca tcactgatgg cattcacagc ctctatcacc   5640
agcccgctca ccacccaaca taccctcctg tttaacatcc tggggggatg ggtggccgcc   5700
caacttgctc ctcccagcgc tgcttctgct ttcgtaggcg ccggcatcgc tggagcggct   5760
gttggcagca taggccttgg gacggtgctt gtggatattt tggcaggtta tggagcaggg   5820
gtggcaggcg cgctcgtggc ctttaaggtc atgagcggcg agatgccctc caccgaggac   5880
ctggttaacc tactccctgc tatcctctcc cctggcgccc tagtcgtcgg ggtcgtgtgc   5940
gcagcgatac tgcgtcggca cgtgggccca ggggaggggg ctgtgcagtg gatgaaccgg   6000
ctgatagcgt tcgcttcgcg ggtaaccac gtctccccca cgcactatgt gcctgagagc   6060
gacgctgcag cacgtgtcac tcagatcctc tctagtctta ccatcactca gctgctgaag   6120
aggcttcacc agtggatcaa cgaggactgc tccacgccat gctccggctc gtggctaaga   6180
gatgtttggg attggatatg cacggtgttg actgatttca agacctggct ccagtccaag   6240
ctcctgccgc gattgccggg agtccccttc ttctcatgtc aacgtgggta caagggagtc   6300
tggcggggcg acggcatcat gcaaaccacc tgcccatgtg gagcacagat caccggacat   6360
gtgaaaaacg gttccatgag gatcgtgggg cctaggacct gtagtaacac gtggcatgga   6420
acattcccca ttaacgcgta caccacgggc ccctgcacgc cctccccggc gccaaattat   6480
tctagggcgc tgtggcgggt ggctgctgag gagtacgtgg aggttacgcg ggtgggggat   6540
ttccactacg tgacgggcat gaccactgac aacgtaaagt gcccgtgtca ggttccggcc   6600
cccgaattct tcacagaagt ggatggggtg cggttgcaca ggtacgctcc agcgtgcaaa   6660
cccctcctac gggaggaggt cacattcctg gtcgggctca atcaatacct ggttgggtca   6720
cagctcccat gcgagcccga accggacgta gcagtgctca cttccatgct caccgacccc   6780
```

-continued tcccacatta cggcggagac ggctaagcgt aggctggcca ggggatctcc cccctccttg 6840
gccagctcat cagctagcca gctgtctgcg ccttccttga aggcaacatg cactacccgt 6900
catgactccc cggacgctga cctcatcgag gccaacctcc tgtggcggca ggagatgggc 6960
gggaacatca cccgcgtgga gtcagaaaat aaggtagtaa ttttggactc tttcgagccg 7020
ctccaagcgg aggaggatga gagggaagta tccgttccgg cggagatcct gcggaggtcc 7080
aggaaattcc ctcgagcgat gcccatatgg gcacgcccgg attacaaccc tccactgtta 7140
gagtcctgga aggacccgga ctacgtccct ccagtggtac acgggtgtcc attgccgcct 7200
gccaaggccc ctccgatacc acctccacgg aggaagagga cggttgtcct gtcagaatct 7260
accgtgtctt ctgccttggc ggagctcgcc acaaagacct tcggcagctc cgaatcgtcg 7320
gccgtcgaca gcggcacggc aacggcctct cctgaccagc cctccgacga cggcgacgcg 7380
ggatccgacg ttgagtcgta ctcctccatg cccccccttg aggggggagcc gggggatccc 7440 gatctcagcg acgggtcttg gtctaccgta agcgaggagc ttaaggctag tgaggacgtc 7500
gtctgctgct cgatgtccta cacatggaca ggcgccctga tcacgccatg cgctgcggag 7560
gaaaccaagc tgcccatcaa tgcactgagc aactctttgc tccgtcacca caacttggtc 7620
tatgctacaa catctcgcag cgcaagcctg cggcagaaga aggtcacctt tgacagactg 7680
caggtcctgg acgaccacta ccgggacgtg ctcaaggaga tgaaggcgaa ggcgtccaca 7740
gttaaggcta aacttctatc cgtggaggaa gcctgtaagc tgacgccccc acattcggcc 7800
agatctaaat ttggctatgg ggcaaaggac gtccggaacc tatccagcaa ggccgttaac 7860
cacatccgct ccgtgtggaa ggacttgctg gaagacactg agacaccaat tgacaccacc 7920
atcatggcaa aaaatgaggt tttctgcgtc caaccagaga aggggggccg caagccagct 7980
cgccttatcg tattcccaga tttgggggtt cgtgtgtgcg agaaaatggc cctttacgat 8040
gtggtctcca ccctccctca ggccgtgatg ggctcttcat acggattcca atactctcct 8100
ggacagcggg tcgagttcct ggtgaatgcc tggaaagcga agaaatgccc tatgggcttc 8160
gcatatgaca cccgctgttt tgactcaacg gtcactgaga atgacatccg tgttgaggag 8220
tcaatctacc aatgttgtga cttggccccc gaagccagac aggccataag gtcgctcaca 8280
gagcggcttt acatcggggg cccccctgact aattctaaag ggcagaactg cggctatcgc 8340
cggtgccgcg cgagcggtgt actgacgacc agctgcggta ataccctcac atgttacttg 8400
aaggccgctg cggcctgtcg agctgcgaag ctccaggact gcacgatgct cgtatgcgga 8460
gacgaccttg tcgttatctg tgaaagcgcg ggggacccaag aggacgaggc gagcctacgg 8520
gccttcacgg aggctatgac tagatactct gcccccccctg ggacccgcc caaaccagaa 8580 tacgacttgg agttgataac atcatgctcc tccaatgtgt cagtcgcgca cgatgcatct 8640
ggcaaaaggg tgtactatct cacccgtgac ccccaccaccc cccttgcgcg ggctgcgtgg 8700
gagacagcta gacacactcc agtcaattcc tggctaggca acatcatcat gtatgcgccc 8760
accttgtggg caaggatgat cctgatgact catttcttct ccatccttct agctcaggaa 8820
caacttgaaa aagccctaga ttgtcagatc tacggggcct gttactccat tgagccactt 8880
gacctacctc agatcattca acgactccat ggccttagcg cattttcact ccatagttac 8940
tctccaggtg agatcaatag ggtggcttca tgcctcagga aacttggggt accgcccttg 9000
cgagtctgga gacatcgggc cagaagtgtc cgcgctaggc tactgtccca gggggggagg 9060
gctgccactt gtggcaagta cctcttcaac tgggcagtaa ggaccaagct caaactcact 9120

-continued

```
ccaatcccgg ctgcgtccca gttggattta tccagctggt tcgttgctgg ttacagcggg   9180
ggagacatat atcacagcct gtctcgtgcc cgaccccgct ggttcatgtg gtgcctactc   9240
ctactttctg taggggtagg catctatcta ctccccaacc gatgacttaa gacggggagc   9300
taaacactcc aggccaatag gccatcctgt ttttttccct ttttttttt cttttttttt   9360
ttttttttt ttttttttt tttttctcct tttttttcc tctttttttc cttttctttc   9420
ctttggtggc tccatcttag ccctagtcac ggctagctgt gaaaggtccg tgagccgctt   9480
gactgcagag agtgctgata ctggcctctc tgcagatcaa gtactactag tccctttagt   9540
gagggttaat tcaattcttg aagacgaaag ggcctcgtga tacgcctatt tttataggtt   9600
aatgtcatga taataatggt ttcttagacg tcaggtggca cttttcgggg aaatgtgcgc   9660
ggaacccctta tttgtttatt tttctaaata cattcaaata tgtatccgct catgagacaa   9720
taaccctgat aaatgcttca ataatattga aaaaggaaga gtatgagtat tcaacatttc   9780
cgtgtcgccc ttattccctt ttttgcggca ttttgccttc ctgtttttgc tcacccagaa   9840
acgctggtga aagtaaaaga tgctgaagat cagttgggtg cacgagtggg ttacatcgaa   9900
ctggatctca acagcggtaa gatccttgag agttttcgcc ccgaagaacg ttttccaatg   9960
atgagcactt ttaaagttct gctatgtggc gcggtattat cccgtgttga cgccgggcaa  10020
gagcaactcg gtcgccgcat acactattct cagaatgact tggttgagta ctcaccagtc  10080
acagaaaagc atcttacgga tggcatgaca gtaagagaat tatgcagtgc tgccataacc  10140
atgagtgata acactgcggc caacttactt ctgacaacga tcggaggacc gaaggagcta  10200
accgcttttt tgcacaacat gggggatcat gtaactcgcc ttgatcgttg ggaaccggag  10260
ctgaatgaag ccataccaaa cgacgagcgt gacaccacga tgcctgcagc aatggcaaca  10320
acgttgcgca aactattaac tggcgaacta cttactctag cttcccggca acaattaata  10380
gactggatgg aggcggataa agttgcagga ccacttctgc gctcggccct tccggctggc  10440
tggtttattg ctgataaatc tggagccggt gagcgtgggt ctcgcggtat cattgcagca  10500
ctggggccag atggtaagcc ctcccgtatc gtagttatct acacgacggg gagtcaggca  10560
actatggatg aacgaaatag acagatcgct gagataggtg cctcactgat taagcattgg  10620
taactgtcag accaagttta ctcatatata ctttagattg atttaaaact tcatttttaa  10680
tttaaaagga tctaggtgaa gatccttttt gataatctca tgaccaaaat cccttaacgt  10740
gagttttcgt tccactgagc gtcagacccc gtagaaaaga tcaaaggatc ttcttgagat  10800
cctttttttc tgcgcgtaat ctgctgcttg caaacaaaaa aaccaccgct accagcggtg  10860
gtttgtttgc cggatcaaga gctaccaact ctttttccga aggtaactgg cttcagcaga  10920
gcgcagatac caaatactgt ccttctagtg tagccgtagt taggccacca cttcaagaac  10980
tctgtagcac cgcctacata cctcgctctg ctaatcctgt taccagtggc tgctgccagt  11040
ggcgataagt cgtgtcttac cgggttggac tcaagacgat agttaccgga taaggcgcag  11100
cggtcgggct gaacgggggg ttcgtgcaca cagcccagct tggagcgaac gacctacacc  11160
gaactgagat acctacagcg tgagctatga gaaagcgcca cgcttcccga agggagaaag  11220
gcggacaggt atccggtaag cggcagggtc ggaacaggag agcgcacgag ggagcttcca  11280
gggggaaacg cctggtatct ttatagtcct gtcgggtttc gccacctctg acttgagcgt  11340
cgatttttgt gatgctcgtc aggggggcgg agcctatgga aaaacgccag caacgcggcc  11400
tttttacggt tcctggcctt ttgctggcct tttgctcaca tgttctttcc tgcgttatcc  11460
cctgattctg tggataaccg tattaccgcc tttgagtgag ctgataccgc tcgccgcagc  11520
```

cgaacgaccg agcgcagcga gtcagtgagc gaggaagcgg aagagcgcct gatgcggtat 11580
tttctcctta cgcatctgtg cggtatttca caccgcatat ggtgcactct cagtacaatc 11640
tgctctgatg ccgcatagtt aagccagtat acactccgct atcgctacgt gactgggtca 11700
tggctgcgcc ccgacacccg ccaacacccg ctgacgcgcc ctgacgggct tgtctgctcc 11760
cggcatccgc ttacagacaa gctgtgaccg tctccgggag ctgcatgtgt cagaggtttt 11820
caccgtcatc accgaaacgc gcgaggcagc tgcggtaaag ctcatcagcg tggtcgtgaa 11880
gcgattcaca gatgtctgcc tgttcatccg cgtccagctc gttgagtttc tccagaagcg 11940
ttaatgtctg gcttctgata aagcgggcca tgttaagggc ggtttttttcc tgtttggtca 12000 ctgatgcctc cgtgtaaggg ggatttctgt tcatgggggt aatgataccg atgaaacgag 12060
agaggatgct cacgatacgg gttactgatg atgaacatgc ccggttactg gaacgttgtg 12120
agggtaaaca actggcggta tggatgcggc gggaccagag aaaaatcact cagggtcaat 12180
gccagcgctt cgttaataca gatgtaggtg ttccacaggg tagccagcag catcctgcga 12240
tgcagatccg gaacataatg gtgcagggcg ctgacttccg cgtttccaga ctttacgaaa 12300
cacggaaacc gaagaccatt catgttgttg ctcaggtcgc agacgttttg cagcagcagt 12360
cgcttcacgt tcgctcgcgt atcggtgatt cattctgcta accagtaagg caaccccgcc 12420
agcctagccg ggtcctcaac gacaggagca cgatcatgcg cacccgtggc caggacccaa 12480
cgctgcccga gatgcgccgc gtgcggctgc tggagatggc ggacgcgatg gatatgttct 12540
gccaagctaa gctgcctgca ggtaatacga ctcactata 12579

<210> SEQ ID NO 21
<211> LENGTH: 10773
<212> TYPE: DNA
<213> ORGANISM: Hepatitis C virus

<400> SEQUENCE: 21
gccagccccc gattgggggc gacactccac catagatcac tcccctgtga ggaactactg 60
tcttcacgca gaaagcgtct agccatggcg ttagtatgag tgtcgtgcag cctccaggac 120 ccccccctccc gggagagcca tagtggtctg cggaaccggt gagtacaccg gaattgccag 180
gacgaccggg tcctttcttg gatcaacccg ctcaatgcct ggagatttgg gcgtgccccc 240
gcgagactgc tagccgagta gtgttgggtc gcgaaaggcc ttgtggtact gcctgatagg 300
gtgcttgcga gtgccccggg aggtctcgta gaccgtgcac cgtttaaacc cccgtgctgc 360
tggaagtcga tttcaggctt agggtaaccg tggacctcga aaacagacgc acaaaaccaa 420
gttcaataga agggggtaca aaccagtacc accacgaaca agcacttctg tttccccggt 480
gatgtcgtat agactgcttg cgtggttgaa agcgacggat ccgttatccg cttatgtact 540
tcgagaagcc cagtaccacc tcggaatctt cgatgcgttg cgctcagcac tcaaccccag 600
agtgtagctt aggctgatga gtctggacat ccctcaccgg tgacggtggt ccaggctgcg 660
ttggcggcct acctatggct aacgccatgg gacgctagtt gtgaacaagg tgtgaagagc 720
ctattgagct acataagaat cctccggccc ctgaatgcgg ctaatcccaa cctcggagca 780
ggtggtcaca aaccagtgat tggcctgtcg taacgcgcaa gtccgtggcg gaaccgacta 840
ctttgggtgt ccgtgtttcc ttttatttta ttgtggctgc ttatggtgac aatcacagat 900
tgttatcata aagcgaattg gattggccat ccggtgaaag tgagactcat tatctatctg 960
tttgctggat ccgctccatt gagtgtgttt actctaagta caatttcaac agttatttca 1020

```
atcagacaat tgtatcataa tggcgggccc agaagacgcc aaaaacataa agaaaggccc   1080
ggcgccattc tatcctctag aggatggaac cgctggagag caactgcata aggctatgaa   1140
gagatacgcc ctggttcctg gaacaattgc ttttacagat gcacatatcg aggtgaacat   1200
cacgtacgcg gaatacttcg aaatgtccgt tcggttggca gaagctatga aacgatatgg   1260
gctgaataca aatcacagaa tcgtcgtatg cagtgaaaac tctcttcaat tctttatgcc   1320
ggtgttgggc gcgttattta tcggagttgc agttgcgccc gcgaacgaca tttataatga   1380
acgtgaattg ctcaacagta tgaacatttc gcagcctacc gtagtgtttg tttccaaaaa   1440
ggggttgcaa aaaattttga acgtgcaaaa aaaattacca ataatccaga aaattattat   1500
catggattct aaaacggatt accagggatt tcagtcgatg tacacgttcg tcacatctca   1560
tctacctccc ggttttaatg aatacgattt tgtaccagag tcctttgatc gtgacaaaac   1620
aattgcactg ataatgaatt cctctggatc tactgggtta cctaagggtg tggcccttcc   1680
gcatagaact gcctgcgtca gattctcgca tgccagagat cctatttttg gcaatcaaat   1740
cattccggat actgcgattt taagtgttgt tccattccat cacggttttg gaatgtttac   1800
tacactcgga tatttgatat gtggatttcg agtcgtctta atgtatagat ttgaagaaga   1860
gctgttttta cgatcccttc aggattacaa aattcaaagt gcgttgctag taccaaccct   1920
attttcattc ttcgccaaaa gcactctgat tgacaaatac gatttatcta atttacacga   1980
aattgcttct gggggcgcac ctctttcgaa agaagtcggg gaagcggttg caaaacgctt   2040
ccatcttcca gggatacgac aaggatatgg gctcactgag actacatcag ctattctgat   2100
tacacccgag ggggatgata aaccgggcgc ggtcggtaaa gttgttccat tttttgaagc   2160
gaaggttgtg gatctggata ccgggaaaac gctgggcgtt aatcagagag gcgaattatg   2220
tgtcagagga cctatgatta tgtccggtta tgtaaacaat ccggaagcga ccaacgcctt   2280
gattgacaag gatggatggc tacattctgg agacatagct tactgggacg aagacgaaca   2340
cttcttcata gttgaccgct tgaagtcttt aattaaatac aaaggatatc aggtggcccc   2400
cgctgaattg gaatcgatat tgttacaaca ccccaacatc ttcgacgcgg gcgtggcagg   2460
tcttcccgac gatgacgccg gtgaacttcc cgccgccgtt gttgttttgg agcacggaaa   2520
gacgatgacg gaaaaagaga tcgtggatta cgtcgccagt caagtaacaa ccgcgaaaaa   2580
gttgcgcgga ggagttgtgt ttgtggacga agtaccgaaa ggtcttaccg gaaaactcga   2640
cgcaagaaaa atcagagaga tcctcataaa ggccaagaag ggcggaaagt ccaaattgta   2700
agcggccgcg ttgttaaaca gaccacaacg gtttccctct agcgggatca attccgcccc   2760
ccccccctaa cgttactggc cgaagccgct tggaataagg ccggtgtgcg tttgtctata   2820
tgttattttc caccatattg ccgtcttttg gcaatgtgag ggcccggaaa cctggccctg   2880
tcttcttgac gagcattcct aggggtcttt cccctctcgc caaaggaatg caaggtctgt   2940
tgaatgtcgt gaaggaagca gttcctctgg aagcttcttg aagacaaaca acgtctgtag   3000
cgaccctttg caggcagcgg aaccccccac ctggcgacag gtgcctctgc ggccaaaagc   3060
cacgtgtata agatacacct gcaaaggcgg cacaacccca gtgccacgtt gtgagttgga   3120
tagttgtgga aagagtcaaa tggctctcct caagcgtatt caacaagggg ctgaaggatg   3180
cccagaaggt accccattgt atgggatctg atctggggcc tcggtgcaca tgctttacat   3240
gtgtttagtc gaggttaaaa aaacgtctag gccccccgaa ccacggggac gtggttttcc   3300
tttgaaaaac acgataatac catggcgcct attacggcct actcccaaca gacgcgaggc   3360
ctacttggct gcatcatcac tagcctcaca ggccgggaca ggaaccaggt cgagggggag   3420
```

-continued

```
gtccaagtgg tctccaccgc aacacaatct ttcctggcga cctgcgtcaa tggcgtgtgt   3480
tggactgtct atcatggtgc cggctcaaag acccttgccg gcccaaaggg cccaatcacc   3540
caaatgtaca ccaatgtgga ccaggacctc gtcggctggc aagcgccccc cggggcgcgt   3600
tccttgacac catgcacctg cggcagctcg gacctttact tggtcacgag gcatgccgat   3660
gtcattccgg tgcgccggcg gggcgacagc agggggagcc tactctcccc caggcccgtc   3720
tcctacttga agggctcttc gggcggtcca ctgctctgcc cctcggggca cgctgtgggc   3780
atctttcggg ctgccgtgtg cacccgaggg gttgcgaagg cggtggactt tgtacccgtc   3840
gagtctatgg gaaccactat gcggtccccg gtcttcacgg acaactcgtc ccctccggcc   3900
gtaccgcaga cattccaggt ggcccatcta cacgccccta ctggtagcgg caagagcact   3960
aaggtgccgg ctgcgtatgc agcccaaggg tataaggtgc ttgtcctgaa cccgtccgtc   4020
gccgccaccc taggtttcgg ggcgtatatg tctaaggcac atggtatcga ccctaacatc   4080
agaatcgggg taaggaccat caccacgggt gcccccatca cgtactccac ctatggcaag   4140
tttcttgccg acggtggttg ctctgggggc gcctatgaca tcataatatg tgatgagtgc   4200
cactcaactg actcgaccac tatcctgggc atcggcacag tcctggacca agcggagacg   4260
gctggagcgc gactcgtcgt gctcgccacc gctacgcctc cgggatcggt caccgtgcca   4320
catccaaaca tcgaggaggt ggctctgtcc agcactggag aaatcccctt ttatggcaaa   4380
gccatcccca tcgagaccat caaggggggg aggcacctca ttttctgcca ttccaagaag   4440
aaatgtgatg agctcgccgc gaagctgtcc ggcctcggac tcaatgctgt agcatattac   4500
cggggccttg atgtatccgt cataccaact agcggagacg tcattgtcgt agcaacggac   4560
gctctaatga cgggctttac cggcgatttc gactcagtga tcgactgcaa tacatgtgtc   4620
acccagacag tcgacttcag cctggacccg accttcacca ttgagacgac gaccgtgcca   4680
caagacgcgg tgtcacgctc gcagcggcga ggcaggactg gtaggggcag gatgggcatt   4740
tacaggtttg tgactccagg agaacggccc tcgggcatgt tcgattcctc ggttctgtgc   4800
gagtgctatg acgcgggctg tgcttggtac gagctcacgc ccgccgagac ctcagttagg   4860
ttgcgggctt acctaaacac accagggttg cccgtctgcc aggaccatct ggagttctgg   4920
gagagcgtct ttacaggcct cacccacata gacgcccatt tcttgtccca gactaagcag   4980
gcaggagaca acttccccta cctggtagca taccaggcta cggtgtgcgc cagggctcag   5040
gctccacctc catcgtggga ccaaatgtgg aagtgtctca tacggctaaa gcctacgctg   5100
cacgggccaa cgcccctgct gtataggctg ggagccgttc aaaacgaggt tactaccaca   5160
caccccataa ccaaatacat catggcatgc atgtcggctg acctggaggt cgtcacgagc   5220
acctgggtgc tggtaggcgg agtcctagca gctctggccg cgtattgcct gacaacaggc   5280
agcgtggtca ttgtgggcag gatcatcttg tccggaaagc cggccatcat tcccgacagg   5340
gaagtccttt accgggagtt cgatgagatg gaagagtgcg cctcacacct cccttacatc   5400
gaacagggaa tgcagctcgc cgaacaattc aaacagaagg caatcgggtt gctgcaaaca   5460
gccaccaagc aagcggaggc tgctgctccc gtggtggaat ccaagtggcg gaccctcgaa   5520
gccttctggg cgaagcatat gtggaatttc atcagcggga tacaatattt agcaggcttg   5580
tccactctgc ctggcaaccc cgcgatagca tcactgatgg cattcacagc ctctatcacc   5640
agcccgctca ccacccaaca taccctcctg tttaacatcc tgggggggatg ggtggccgcc   5700
caacttgctc ctcccagcgc tgcttctgct ttcgtaggcg ccggcatcgc tggagcggct   5760
```

-continued gttggcagca taggccttgg gacggtgctt gtggatattt tggcaggtta tggagcaggg 5820
gtggcaggcg cgctcgtggc ctttaaggtc atgagcggcg agatgccctc caccgaggac 5880
ctggttaacc tactccctgc tatcctctcc cctggcgccc tagtcgtcgg ggtcgtgtgc 5940
gcagcgatac tgcgtcggca cgtgggccca ggggaggggg ctgtgcagtg gatgaaccgg 6000
ctgatagcgt tcgcttcgcg gggtaaccac gtctccccca cgcactatgt gcctgagagc 6060
gacgctgcag cacgtgtcac tcagatcctc tctagtctta ccatcactca gctgctgaag 6120
aggcttcacc agtggatcaa cgaggactgc tccacgccat gctccggctc gtggctaaga 6180
gatgtttggg attggatatg cacggtgttg actgatttca agacctggct ccagtccaag 6240
ctcctgccgc gattgccggg agtccccttc ttctcatgtc aacgtgggta caagggagtc 6300
tggcggggcg acggcatcat gcaaaccacc tgcccatgtg gagcacagat caccggacat 6360
gtgaaaaacg gttccatgag gatcgtgggg cctaggacct gtagtaacac gtggcatgga 6420
acattcccca ttaacgcgta caccacgggc ccctgcacgc cctccccggc gccaaattat 6480
tctagggcgc tgtggcgggt ggctgctgag gagtacgtgg aggttacgcg ggtgggggat 6540
ttccactacg tgacgggcat gaccactgac aacgtaaagt gcccgtgtca ggttccggcc 6600
cccgaattct tcacagaagt ggatggggtg cggttgcaca ggtacgctcc agcgtgcaaa 6660
cccctcctac gggaggaggt cacattcctg gtcgggctca atcaatacct ggttgggtca 6720
cagctcccat gcgagcccga accggacgta gcagtgctca cttccatgct caccgacccc 6780
tcccacatta cggcggagac ggctaagcgt aggctggcca ggggatctcc cccctccttg 6840
gccagctcat cagctagcca gctgtctgcg ccttccttga aggcaacatg cactacccgt 6900
catgactccc cggacgctga cctcatcgag gccaacctcc tgtggcggca ggagatgggc 6960
gggaacatca cccgcgtgga gtcagaaaat aaggtagtaa ttttggactc tttcgagccg 7020
ctccaagcgg aggaggatga gagggaagta tccgttccgg cggagatcct gcggaggtcc 7080
aggaaattcc ctcgagcgat gcccatatgg gcacgcccgg attacaaccc tccactgtta 7140
gagtcctgga aggacccgga ctacgtccct ccagtggtac acgggtgtcc attgccgcct 7200
gccaaggccc cttcgatacc acctccacgg aggaagagga cggttgtcct gtcagaatct 7260
accgtgtctt ctgccttggc ggagctcgcc acaaagacct tcggcagctc cgaatcgtcg 7320
gccgtcgaca gcggcacggc aacggcctct cctgaccagc cctccgacga cggcgacgcg 7380
ggatccgacg ttgagtcgta ctcctccatg cccccccttg agggggagcc gggggatccc 7440
gatctcagcg acgggtcttg gtctaccgta agcgaggagc ttaagacggg gagctaaaca 7500
ctccaggcca ataggccatc ctgttttttt cccttttttt ttttcttttt tttttttttt 7560
tttttttttt tttttttttc tccttttttt ttcctctttt tttccttttc tttcctttgg 7620
tggctccatc ttagccctag tcacggctag ctgtgaaagg tccgtgagcc gcttgactgc 7680
agagagtgct gatactggcc tctctgcaga tcaagtacta ctagtccctt tagtgagggt 7740
taattcaatt cttgaagacg aaagggcctc gtgatacgcc tatttttata ggttaatgtc 7800
atgataataa tggtttctta gacgtcaggt ggcacttttc ggggaaatgt gcgcggaacc 7860
cctatttgtt tatttttcta aatacattca aatatgtatc cgctcatgag acaataaccc 7920
tgataaatgc ttcaataata ttgaaaaagg aagagtatga gtattcaaca tttccgtgtc 7980
gcccttattc cctttttttgc ggcattttgc cttcctgttt ttgctcaccc agaaacgctg 8040
gtgaaagtaa aagatgctga agatcagttg ggtgcacgag tgggttacat cgaactggat 8100
ctcaacagcg gtaagatcct tgagagtttt cgccccgaag aacgttttcc aatgatgagc 8160

```
acttttaaag ttctgctatg tggcgcggta ttatcccgtg ttgacgccgg gcaagagcaa   8220
ctcggtcgcc gcatacacta ttctcagaat gacttggttg agtactcacc agtcacagaa   8280
aagcatctta cggatggcat gacagtaaga gaattatgca gtgctgccat aaccatgagt   8340
gataacactg cggccaactt acttctgaca acgatcggag gaccgaagga gctaaccgct   8400
tttttgcaca acatggggga tcatgtaact cgccttgatc gttgggaacc ggagctgaat   8460
gaagccatac caaacgacga gcgtgacacc acgatgcctg cagcaatggc aacaacgttg   8520
cgcaaactat taactggcga actacttact ctagcttccc ggcaacaatt aatagactgg   8580
atggaggcgg ataaagttgc aggaccactt ctgcgctcgg cccttccggc tggctggttt   8640
attgctgata aatctggagc cggtgagcgt gggtctcgcg gtatcattgc agcactgggg   8700
ccagatggta agccctcccg tatcgtagtt atctacacga cggggagtca ggcaactatg   8760
gatgaacgaa atagacagat cgctgagata ggtgcctcac tgattaagca ttggtaactg   8820
tcagaccaag tttactcata tatactttag attgatttaa aacttcattt ttaatttaaa   8880
aggatctagg tgaagatcct ttttgataat ctcatgacca aaatccctta acgtgagttt   8940
tcgttccact gagcgtcaga ccccgtagaa aagatcaaag gatcttcttg agatcctttt   9000
tttctgcgcg taatctgctg cttgcaaaca aaaaaaccac cgctaccagc ggtggtttgt   9060
ttgccggatc aagagctacc aactcttttt ccgaaggtaa ctggcttcag cagagcgcag   9120
ataccaaata ctgtccttct agtgtagccg tagttaggcc accacttcaa gaactctgta   9180
gcaccgccta catacctcgc tctgctaatc ctgttaccag tggctgctgc cagtggcgat   9240
aagtcgtgtc ttaccgggtt ggactcaaga cgatagttac cggataaggc gcagcggtcg   9300
ggctgaacgg ggggttcgtg cacacagccc agcttggagc gaacgaccta caccgaactg   9360
agatacctac agcgtgagct atgagaaagc gccacgcttc ccgaagggag aaaggcggac   9420
aggtatccgg taagcggcag ggtcggaaca ggagagcgca cgagggagct tccaggggga   9480
aacgcctggt atctttatag tcctgtcggg tttcgccacc tctgacttga gcgtcgattt   9540
ttgtgatgct cgtcaggggg gcggagccta tggaaaaacg ccagcaacgc ggccttttta   9600
cggttcctgg ccttttgctg gccttttgct cacatgttct ttcctgcgtt atcccctgat   9660
tctgtggata accgtattac cgcctttgag tgagctgata ccgctcgccg cagccgaacg   9720
accgagcgca gcgagtcagt gagcgaggaa gcggaagagc gcctgatgcg gtattttctc   9780
cttacgcatc tgtgcggtat ttcacaccgc atatggtgca ctctcagtac aatctgctct   9840
gatgccgcat agttaagcca gtatacactc cgctatcgct acgtgactgg gtcatggctg   9900
cgccccgaca cccgccaaca cccgctgacg cgccctgacg ggcttgtctg ctcccggcat   9960
ccgcttacag acaagctgtg accgtctccg ggagctgcat gtgtcagagg ttttcaccgt  10020
catcaccgaa acgcgcgagg cagctgcggt aaagctcatc agcgtggtcg tgaagcgatt  10080
cacagatgtc tgcctgttca tccgcgtcca gctcgttgag tttctccaga agcgttaatg  10140
tctggcttct gataaagcgg gccatgttaa gggcggtttt ttcctgtttg gtcactgatg  10200
cctccgtgta agggggattt ctgttcatgg gggtaatgat accgatgaaa cgagagagga  10260
tgctcacgat acgggttact gatgatgaac atgcccggtt actggaacgt tgtgagggta  10320
aacaactggc ggtatggatg cggcgggacc agagaaaaat cactcagggt caatgccagc  10380
gcttcgttaa tacagatgta ggtgttccac agggtagcca gcagcatcct gcgatgcaga  10440
tccggaacat aatggtgcag ggcgctgact tccgcgtttc cagactttac gaaacacgga  10500
```

aaccgaagac cattcatgtt gttgctcagg tcgcagacgt tttgcagcag cagtcgcttc 10560
acgttcgctc gcgtatcggt gattcattct gctaaccagt aaggcaaccc cgccagccta 10620
gccgggtcct caacgacagg agcacgatca tgcgcacccg tggccaggac ccaacgctgc 10680
ccgagatgcg ccgcgtgcgg ctgctggaga tggcggacgc gatggatatg ttctgccaag 10740
ctaagctgcc tgcaggtaat acgactcact ata 10773

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
ggcgccattc tatccactag aggatggaac c 31

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
ggttccatcc tctagtggat agaatggcgc c 31

<210> SEQ ID NO 24
<211> LENGTH: 63
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
gagtgctgat actggcctct ctgcagatca agtctagaaa gtccctttag tgagggttaa 60
ttc 63

<210> SEQ ID NO 25
<211> LENGTH: 63
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
gaattaaccc tcactaaagg gactttctag acttgatctg cagagaggcc agtatcagca 60
ctc 63

<210> SEQ ID NO 26
<211> LENGTH: 12579
<212> TYPE: DNA
<213> ORGANISM: Hepatitis C virus

<400> SEQUENCE: 26
gccagccccc gattgggggc gacactccac catagatcac tcccctgtga ggaactactg 60
tcttcacgca gaaagcgtct agccatggcg ttagtatgag tgtcgtgcag cctccaggac 120 ccccccctccc gggagagcca tagtggtctg cggaaccggt gagtacaccg gaattgccag 180

```
gacgaccggg tcctttcttg gatcaacccg ctcaatgcct ggagatttgg gcgtgccccc    240
gcgagactgc tagccgagta gtgttgggtc gcgaaaggcc ttgtggtact gcctgatagg    300
gtgcttgcga gtgccccggg aggtctcgta gaccgtgcac cgtttaaacc cccgtgctgc    360
tggaagtcga tttcaggctt agggtaaccg tggacctcga aaacagacgc acaaaaccaa    420
gttcaataga agggggtaca aaccagtacc accacgaaca agcacttctg tttccccggt    480
gatgtcgtat agactgcttg cgtggttgaa agcgacggat ccgttatccg cttatgtact    540
tcgagaagcc cagtaccacc tcggaatctt cgatgcgttg cgctcagcac tcaaccccag    600
agtgtagctt aggctgatga gtctggacat ccctcaccgg tgacggtggt ccaggctgcg    660
ttggcggcct acctatggct aacgccatgg gacgctagtt gtgaacaagg tgtgaagagc    720
ctattgagct acataagaat cctccggccc ctgaatgcgg ctaatcccaa cctcggagca    780
ggtggtcaca aaccagtgat tggcctgtcg taacgcgcaa gtccgtggcg gaaccgacta    840
ctttgggtgt ccgtgtttcc ttttatttta ttgtggctgc ttatggtgac aatcacagat    900
tgttatcata aagcgaattg gattggccat ccggtgaaag tgagactcat tatctatctg    960
tttgctggat ccgctccatt gagtgtgttt actctaagta caatttcaac agttatttca   1020
atcagacaat tgtatcataa tggcgggccc agaagacgcc aaaaacataa agaaaggccc   1080
ggcgccattc tatccactag aggatggaac cgctggagag caactgcata aggctatgaa   1140
gagatacgcc ctggttcctg gaacaattgc ttttacagat gcacatatcg aggtgaacat   1200
cacgtacgcg gaatacttcg aaatgtccgt tcggttggca gaagctatga aacgatatgg   1260
gctgaataca aatcacagaa tcgtcgtatg cagtgaaaac tctcttcaat tctttatgcc   1320
ggtgttgggc gcgttattta tcggagttgc agttgcgccc gcgaacgaca tttataatga   1380
acgtgaattg ctcaacagta tgaacatttc gcagcctacc gtagtgtttg tttccaaaaa   1440
ggggttgcaa aaaattttga acgtgcaaaa aaaattacca ataatccaga aaattattat   1500
catggattct aaaacggatt accagggatt tcagtcgatg tacacgttcg tcacatctca   1560
tctacctccc ggttttaatg aatacgattt tgtaccagag tcctttgatc gtgacaaaac   1620
aattgcactg ataatgaatt cctctggatc tactgggtta cctaagggtg tggcccttcc   1680
gcatagaact gcctgcgtca gattctcgca tgccagagat cctatttttg gcaatcaaat   1740
cattccggat actgcgattt taagtgttgt tccattccat cacggttttg gaatgtttac   1800
tacactcgga tatttgatat gtggatttcg agtcgtctta atgtatagat ttgaagaaga   1860
gctgttttta cgatcccttc aggattacaa aattcaaagt gcgttgctag taccaaccct   1920
attttcattc ttcgccaaaa gcactctgat tgacaaatac gatttatcta atttacacga   1980
aattgcttct gggggcgcac ctctttcgaa agaagtcggg gaagcggttg caaaacgctt   2040
ccatcttcca gggatacgac aaggatatgg gctcactgag actacatcag ctattctgat   2100
tacacccgag gggatgata aaccgggcgc ggtcggtaaa gttgttccat tttttgaagc   2160
gaaggttgtg gatctggata ccgggaaaac gctgggcgtt aatcagagag gcgaattatg   2220
tgtcagagga cctatgatta tgtccggtta tgtaaacaat ccggaagcga ccaacgcctt   2280
gattgacaag gatggatggc tacattctgg agacatagct tactgggacg aagacgaaca   2340
cttcttcata gttgaccgct tgaagtcttt aattaaatac aaaggatatc aggtggcccc   2400
cgctgaattg gaatcgatat tgttacaaca ccccaacatc ttcgacgcgg gcgtggcagg   2460
tcttcccgac gatgacgccg gtgaacttcc cgccgccgtt gttgttttgg agcacggaaa   2520
```

-continued

```
gacgatgacg gaaaaagaga tcgtggatta cgtcgccagt caagtaacaa ccgcgaaaaa   2580
gttgcgcgga ggagttgtgt ttgtggacga agtaccgaaa ggtcttaccg gaaaactcga   2640
cgcaagaaaa atcagagaga tcctcataaa ggccaagaag ggcggaaagt ccaaattgta   2700
agcggccgcg ttgttaaaca gaccacaacg gtttccctct agcgggatca attccgcccc   2760
ccccccctaa cgttactggc cgaagccgct tggaataagg ccggtgtgcg tttgtctata   2820
tgttattttc caccatattg ccgtcttttg gcaatgtgag ggcccggaaa cctggccctg   2880
tcttcttgac gagcattcct aggggtcttt cccctctcgc caaaggaatg caaggtctgt   2940
tgaatgtcgt gaaggaagca gttcctctgg aagcttcttg aagacaaaca acgtctgtag   3000
cgaccctttg caggcagcgg aaccccccac ctggcgacag gtgcctctgc ggccaaaagc   3060
cacgtgtata agatacacct gcaaaggcgg cacaacccca gtgccacgtt gtgagttgga   3120
tagttgtgga aagagtcaaa tggctctcct caagcgtatt caacaagggg ctgaaggatg   3180
cccagaaggt accccattgt atgggatctg atctggggcc tcggtgcaca tgctttacat   3240
gtgtttagtc gaggttaaaa aaacgtctag gccccccgaa ccacggggac gtggttttcc   3300
tttgaaaaac acgataatac catggcgcct attacggcct actcccaaca gacgcgaggc   3360
ctacttggct gcatcatcac tagcctcaca ggccgggaca ggaaccaggt cgagggggag   3420
gtccaagtgg tctccaccgc aacacaatct ttcctggcga cctgcgtcaa tggcgtgtgt   3480
tggactgtct atcatggtgc cggctcaaag acccttgccg gcccaaaggg cccaatcacc   3540
caaatgtaca ccaatgtgga ccaggacctc gtcggctggc aagcgccccc cggggcgcgt   3600
tccttgacac catgcacctg cggcagctcg gacctttact tggtcacgag gcatgccgat   3660
gtcattccgg tgcgccggcg gggcgacagc agggggagcc tactctcccc caggcccgtc   3720
tcctacttga agggctcttc gggcggtcca ctgctctgcc cctcggggca cgctgtgggc   3780
atctttcggg ctgccgtgtg cacccgaggg gttgcgaagg cggtggactt tgtacccgtc   3840
gagtctatgg gaaccactat gcggtccccg gtcttcacgg acaactcgtc ccctccggcc   3900
gtaccgcaga cattccaggt ggcccatcta cacgccccta ctggtagcgg caagagcact   3960
aaggtgccgg ctgcgtatgc agcccaaggg tataaggtgc ttgtcctgaa cccgtccgtc   4020
gccgccaccc taggtttcgg ggcgtatatg tctaaggcac atggtatcga ccctaacatc   4080
agaatcgggg taaggaccat caccacgggt gccccccatca cgtactccac ctatggcaag   4140
tttcttgccg acggtggttg ctctgggggc gcctatgaca tcataatatg tgatgagtgc   4200
cactcaactg actcgaccac tatcctgggc atcggcacag tcctggacca agcggagacg   4260
gctggagcgc gactcgtcgt gctcgccacc gctacgcctc cgggatcggt caccgtgcca   4320
catccaaaca tcgaggaggt ggctctgtcc agcactggag aaatcccctt ttatggcaaa   4380
gccatcccca tcgagaccat caaggggggg aggcacctca ttttctgcca ttccaagaag   4440
aaatgtgatg agctcgccgc gaagctgtcc ggcctcggac tcaatgctgt agcatattac   4500
cggggccttg atgtatccgt cataccaact agcggagacg tcattgtcgt agcaacggac   4560
gctctaatga cgggctttac cggcgatttc gactcagtga tcgactgcaa tacatgtgtc   4620
acccagacag tcgacttcag cctggacccg accttcacca ttgagacgac gaccgtgcca   4680
caagacgcgg tgtcacgctc gcagcggcga ggcaggactg gtaggggcag gatgggcatt   4740
tacaggtttg tgactccagg agaacggccc tcgggcatgt tcgattcctc ggttctgtgc   4800
gagtgctatg acgcgggctg tgcttggtac gagctcacgc ccgccgagac ctcagttagg   4860
ttgcgggctt acctaaacac accagggttg cccgtctgcc aggaccatct ggagttctgg   4920
```

```
gagagcgtct ttacaggcct cacccacata gacgcccatt tcttgtccca gactaagcag   4980
gcaggagaca acttccccta cctggtagca taccaggcta cggtgtgcgc cagggctcag   5040
gctccacctc catcgtggga ccaaatgtgg aagtgtctca tacggctaaa gcctacgctg   5100
cacgggccaa cgcccctgct gtataggctg ggagccgttc aaaacgaggt tactaccaca   5160
caccccataa ccaaatacat catggcatgc atgtcggctg acctggaggt cgtcacgagc   5220
acctgggtgc tggtaggcgg agtcctagca gctctggccg cgtattgcct gacaacaggc   5280
agcgtggtca ttgtgggcag gatcatcttg tccggaaagc cggccatcat tcccgacagg   5340
gaagtccttt accgggagtt cgatgagatg gaagagtgcg cctcacacct cccttacatc   5400
gaacagggaa tgcagctcgc cgaacaattc aaacagaagg caatcgggtt gctgcaaaca   5460
gccaccaagc aagcggaggc tgctgctccc gtggtggaat ccaagtggcg gaccctcgaa   5520
gccttctggg cgaagcatat gtggaatttc atcagcggga tacaatattt agcaggcttg   5580
tccactctgc ctggcaaccc cgcgatagca tcactgatgg cattcacagc ctctatcacc   5640
agcccgctca ccacccaaca taccctcctg tttaacatcc tgggggggatg ggtggccgcc   5700
caacttgctc ctcccagcgc tgcttctgct ttcgtaggcg ccggcatcgc tggagcggct   5760
gttggcagca taggccttgg gacggtgctt gtggatattt tggcaggtta tggagcaggg   5820
gtggcaggcg cgctcgtggc ctttaaggtc atgagcggcg agatgccctc caccgaggac   5880
ctggttaacc tactccctgc tatcctctcc cctggcgccc tagtcgtcgg ggtcgtgtgc   5940
gcagcgatac tgcgtcggca cgtgggccca ggggaggggg ctgtgcagtg gatgaaccgg   6000
ctgatagcgt tcgcttcgcg ggtaaccac gtctccccca cgcactatgt gcctgagagc    6060
gacgctgcag cacgtgtcac tcagatcctc tctagtctta ccatcactca gctgctgaag   6120
aggcttcacc agtggatcaa cgaggactgc tccacgccat gctccggctc gtggctaaga   6180
gatgtttggg attggatatg cacggtgttg actgatttca agacctggct ccagtccaag   6240
ctcctgccgc gattgccggg agtccccttc ttctcatgtc aacgtgggta caagggagtc   6300
tggcggggcg acggcatcat gcaaaccacc tgcccatgtg gagcacagat caccggacat   6360
gtgaaaaacg gttccatgag gatcgtgggg cctaggacct gtagtaacac gtggcatgga   6420
acattcccca ttaacgcgta caccacgggc ccctgcacgc cctccccggc gccaaattat   6480
tctagggcgc tgtggcgggt ggctgctgag gagtacgtgg aggttacgcg ggtgggggat   6540
ttccactacg tgacgggcat gaccactgac aacgtaaagt gcccgtgtca ggttccggcc   6600
cccgaattct tcacagaagt ggatggggtg cggttgcaca ggtacgctcc agcgtgcaaa   6660
cccctcctac gggaggaggt cacattcctg gtcgggctca atcaatacct ggttgggtca   6720
cagctcccat gcgagcccga accggacgta gcagtgctca cttccatgct caccgacccc   6780
tcccacatta cggcggagac ggctaagcgt aggctggcca ggggatctcc cccctccttg   6840
gccagctcat cagctagcca gctgtctgcg ccttccttga aggcaacatg cactacccgt   6900
catgactccc cggacgctga cctcatcgag gccaacctcc tgtggcggca ggagatgggc   6960
gggaacatca cccgcgtgga gtcagaaaat aaggtagtaa ttttggactc tttcgagccg   7020
ctccaagcgg aggaggatga gagggaagta tccgttccgg cggagatcct gcggaggtcc   7080
aggaaattcc ctcgagcgat gcccatatgg gcacgcccgg attacaaccc tccactgtta   7140
gagtcctgga aggacccgga ctacgtccct ccagtggtac acgggtgtcc attgccgcct   7200
gccaaggccc ctccgatacc acctccacgg aggaagagga cggttgtcct gtcagaatct   7260
```

-continued

```
accgtgtctt ctgccttggc ggagctcgcc acaaagacct tcggcagctc cgaatcgtcg   7320
gccgtcgaca gcggcacggc aacggcctct cctgaccagc cctccgacga cggcgacgcg   7380
ggatccgacg ttgagtcgta ctcctccatg ccccccttg agggggagcc gggggatccc   7440
gatctcagcg acgggtcttg gtctaccgta agcgaggagc ttaaggctag tgaggacgtc   7500
gtctgctgct cgatgtccta cacatggaca ggcgccctga tcacgccatg cgctgcggag   7560
gaaaccaagc tgcccatcaa tgcactgagc aactctttgc tccgtcacca caacttggtc   7620
tatgctacaa catctcgcag cgcaagcctg cggcagaaga aggtcacctt tgacagactg   7680
caggtcctgg acgaccacta ccgggacgtg ctcaaggaga tgaaggcgaa ggcgtccaca   7740
gttaaggcta aacttctatc cgtggaggaa gcctgtaagc tgacgccccc acattcggcc   7800
agatctaaat ttggctatgg ggcaaaggac gtccggaacc tatccagcaa ggccgttaac   7860
cacatccgct ccgtgtggaa ggacttgctg gaagacactg agacaccaat tgacaccacc   7920
atcatggcaa aaaatgaggt tttctgcgtc caaccagaga aggggggccg caagccagct   7980
cgccttatcg tattcccaga tttgggggtt cgtgtgtgcg agaaaatggc cctttacgat   8040
gtggtctcca ccctccctca ggccgtgatg ggctcttcat acggattcca atactctcct   8100
ggacagcggg tcgagttcct ggtgaatgcc tggaaagcga agaaatgccc tatgggcttc   8160
gcatatgaca cccgctgttt tgactcaacg gtcactgaga atgacatccg tgttgaggag   8220
tcaatctacc aatgttgtga cttggccccc gaagccagac aggccataag gtcgctcaca   8280
gagcggcttt acatcggggg ccccctgact aattctaaag ggcagaactg cggctatcgc   8340
cggtgccgcg cgagcggtgt actgacgacc agctgcggta ataccctcac atgttacttg   8400
aaggccgctg cggcctgtcg agctgcgaag ctccaggact gcacgatgct cgtatgcgga   8460
gacgaccttg tcgttatctg tgaaagcgcg gggacccaag aggacgaggc gagcctacgg   8520
gccttcacgg aggctatgac tagatactct gccccccctg gggacccgcc caaaccagaa   8580
tacgacttgg agttgataac atcatgctcc tccaatgtgt cagtcgcgca cgatgcatct   8640
ggcaaaaggg tgtactatct cacccgtgac ccccaccacc cccttgcgcg ggctgcgtgg   8700
gagacagcta gacacactcc agtcaattcc tggctaggca acatcatcat gtatgcgccc   8760
accttgtggg caaggatgat cctgatgact catttcttct ccatccttct agctcaggaa   8820
caacttgaaa aagccctaga ttgtcagatc tacggggcct gttactccat tgagccactt   8880
gacctacctc agatcattca acgactccat ggccttagcg cattttcact ccatagttac   8940
tctccaggtg agatcaatag ggtggcttca tgcctcagga aacttggggt accgcccttg   9000
cgagtctgga gacatcgggc cagaagtgtc cgcgctaggc tactgtccca gggggggagg   9060
gctgccactt gtggcaagta cctcttcaac tgggcagtaa ggaccaagct caaactcact   9120
ccaatcccgg ctgcgtccca gttggattta tccagctggt tcgttgctgg ttacagcggg   9180
ggagacatat atcacagcct gtctcgtgcc cgaccccgct ggttcatgtg gtgcctactc   9240
ctactttctg taggggtagg catctatcta ctccccaacc gatgacttaa gacggggagc   9300
taaacactcc aggccaatag gccatcctgt ttttttccct ttttttttt cttttttttt   9360
ttttttttt ttttttttt tttttctcct tttttttcc tcttttttc cttttctttc   9420
ctttggtggc tccatcttag ccctagtcac ggctagctgt gaaaggtccg tgagccgctt   9480
gactgcagag agtgctgata ctggcctctc tgcagatcaa gtctagaaag tccctttagt   9540
gagggttaat tcaattcttg aagacgaaag ggcctcgtga tacgcctatt tttataggtt   9600
aatgtcatga taataatggt ttcttagacg tcaggtggca cttttcgggg aaatgtgcgc   9660
```

```
ggaacccta tttgtttatt tttctaaata cattcaaata tgtatccgct catgagacaa   9720
taaccctgat aaatgcttca ataatattga aaaaggaaga gtatgagtat tcaacatttc   9780
cgtgtcgccc ttattccctt ttttgcggca ttttgccttc ctgtttttgc tcacccagaa   9840
acgctggtga aagtaaaaga tgctgaagat cagttgggtg cacgagtggg ttacatcgaa   9900
ctggatctca acagcggtaa gatccttgag agttttcgcc ccgaagaacg ttttccaatg   9960
atgagcactt ttaaagttct gctatgtggc gcggtattat cccgtgttga cgccgggcaa  10020
gagcaactcg gtcgccgcat acactattct cagaatgact tggttgagta ctcaccagtc  10080
acagaaaagc atcttacgga tggcatgaca gtaagagaat tatgcagtgc tgccataacc  10140
atgagtgata acactgcggc caacttactt ctgacaacga tcggaggacc gaaggagcta  10200
accgcttttt tgcacaacat gggggatcat gtaactcgcc ttgatcgttg ggaaccggag  10260
ctgaatgaag ccataccaaa cgacgagcgt gacaccacga tgcctgcagc aatggcaaca  10320
acgttgcgca aactattaac tggcgaacta cttactctag cttcccggca acaattaata  10380
gactggatgg aggcggataa agttgcagga ccacttctgc gctcggccct tccggctggc  10440
tggtttattg ctgataaatc tggagccggt gagcgtgggt ctcgcggtat cattgcagca  10500
ctggggccag atggtaagcc ctcccgtatc gtagttatct acacgacggg gagtcaggca  10560
actatggatg aacgaaatag acagatcgct gagataggtg cctcactgat taagcattgg  10620
taactgtcag accaagttta ctcatatata ctttagattg atttaaaact tcatttttaa  10680
tttaaaagga tctaggtgaa gatccttttt gataatctca tgaccaaaat cccttaacgt  10740
gagttttcgt tccactgagc gtcagacccc gtagaaaaga tcaaaggatc ttcttgagat  10800
cctttttttc tgcgcgtaat ctgctgcttg caaacaaaaa aaccaccgct accagcggtg  10860
gtttgtttgc cggatcaaga gctaccaact ctttttccga aggtaactgg cttcagcaga  10920
gcgcagatac caaatactgt ccttctagtg tagccgtagt taggccacca cttcaagaac  10980
tctgtagcac cgcctacata cctcgctctg ctaatcctgt taccagtggc tgctgccagt  11040
ggcgataagt cgtgtcttac cgggttggac tcaagacgat agttaccgga taaggcgcag  11100
cggtcgggct gaacgggggg ttcgtgcaca cagcccagct tggagcgaac gacctacacc  11160
gaactgagat acctacagcg tgagctatga gaaagcgcca cgcttcccga agggagaaag  11220
gcggacaggt atccggtaag cggcagggtc ggaacaggag agcgcacgag ggagcttcca  11280
gggggaaacg cctggtatct ttatagtcct gtcgggtttc gccacctctg acttgagcgt  11340
cgatttttgt gatgctcgtc aggggggcgg agcctatgga aaaacgccag caacgcggcc  11400
tttttacggt tcctggcctt ttgctggcct tttgctcaca tgttctttcc tgcgttatcc  11460
cctgattctg tggataaccg tattaccgcc tttgagtgag ctgataccgc tcgccgcagc  11520
cgaacgaccg agcgcagcga gtcagtgagc gaggaagcgg aagagcgcct gatgcggtat  11580
tttctcctta cgcatctgtg cggtatttca caccgcatat ggtgcactct cagtacaatc  11640
tgctctgatg ccgcatagtt aagccagtat acactccgct atcgctacgt gactgggtca  11700
tggctgcgcc ccgacacccg ccaacacccg ctgacgcgcc ctgacgggct tgtctgctcc  11760
cggcatccgc ttacagacaa gctgtgaccg tctccgggag ctgcatgtgt cagaggtttt  11820
caccgtcatc accgaaacgc gcgaggcagc tgcggtaaag ctcatcagcg tggtcgtgaa  11880
gcgattcaca gatgtctgcc tgttcatccg cgtccagctc gttgagtttc tccagaagcg  11940
ttaatgtctg gcttctgata aagcgggcca tgttaagggc ggtttttttcc tgtttggtca  12000
```

```
ctgatgcctc cgtgtaaggg ggatttctgt tcatgggggt aatgataccg atgaaacgag  12060
agaggatgct cacgatacgg gttactgatg atgaacatgc ccggttactg gaacgttgtg  12120
agggtaaaca actggcggta tggatgcggc gggaccagag aaaaatcact cagggtcaat  12180
gccagcgctt cgttaataca gatgtaggtg ttccacaggg tagccagcag catcctgcga  12240
tgcagatccg gaacataatg gtgcagggcg ctgacttccg cgtttccaga ctttacgaaa  12300
cacggaaacc gaagaccatt catgttgttg ctcaggtcgc agacgttttg cagcagcagt  12360
cgcttcacgt tcgctcgcgt atcggtgatt cattctgcta accagtaagg caaccccgcc  12420
agcctagccg ggtcctcaac gacaggagca cgatcatgcg cacccgtggc caggacccaa  12480
cgctgcccga gatgcgccgc gtgcggctgc tggagatggc ggacgcgatg gatatgttct  12540
gccaagctaa gctgcctgca ggtaatacga ctcactata                         12579
```

<210> SEQ ID NO 27
<211> LENGTH: 12579
<212> TYPE: DNA
<213> ORGANISM: Hepatitis C virus

<400> SEQUENCE: 27

```
gccagccccc gattgggggc gacactccac catagatcac tcccctgtga ggaactactg     60
tcttcacgca gaaagcgtct agccatggcg ttagtatgag tgtcgtgcag cctccaggac    120
ccccccctccc gggagagcca tagtggtctg cggaaccggt gagtacaccg gaattgccag   180
gacgaccggg tcctttcttg gatcaacccg ctcaatgcct ggagatttgg gcgtgccccc    240
gcgagactgc tagccgagta gtgttgggtc gcgaaaggcc ttgtggtact gcctgatagg    300
gtgcttgcga gtgccccggg aggtctcgta gaccgtgcac cgtttaaacc cccgtgctgc    360
tggaagtcga tttcaggctt agggtaaccg tggacctcga aaacagacgc acaaaaccaa    420
gttcaataga agggggtaca aaccagtacc accacgaaca agcacttctg tttccccggt    480
gatgtcgtat agactgcttg cgtggttgaa agcgacggat ccgttatccg cttatgtact    540
tcgagaagcc cagtaccacc tcggaatctt cgatgcgttg cgctcagcac tcaaccccag    600
agtgtagctt aggctgatga gtctggacat ccctcaccgg tgacggtggt ccaggctgcg    660
ttggcggcct acctatggct aacgccatgg gacgctagtt gtgaacaagg tgtgaagagc    720
ctattgagct acataagaat cctccggccc ctgaatgcgg ctaatcccaa cctcggagca    780
ggtggtcaca aaccagtgat tggcctgtcg taacgcgcaa gtccgtggcg gaaccgacta    840
ctttgggtgt ccgtgtttcc ttttatttta ttgtggctgc ttatggtgac aatcacagat    900
tgttatcata aagcgaattg gattggccat ccggtgaaag tgagactcat tatctatctg    960
tttgctggat ccgctccatt gagtgtgttt actctaagta caatttcaac agttatttca   1020
atcagacaat tgtatcataa tggcgggccc agaagacgcc aaaaacataa agaaaggccc   1080
ggcgccattc tatccactag aggatggaac cgctggagag caactgcata aggctatgaa   1140
gagatacgcc ctggttcctg gaacaattgc ttttacagat gcacatatcg aggtgaacat   1200
cacgtacgcg gaatacttcg aaatgtccgt tcggttggca gaagctatga aacgatatgg   1260
gctgaataca aatcacagaa tcgtcgtatg cagtgaaaac tctcttcaat tctttatgcc   1320
ggtgttgggc gcgttattta tcggagttgc agttgcgccc gcgaacgaca tttataatga   1380
acgtgaattg ctcaacagta tgaacatttc gcagcctacc gtagtgtttg tttccaaaaa   1440
ggggttgcaa aaaattttga acgtgcaaaa aaaattacca ataatccaga aaattattat   1500
catggattct aaaacggatt accagggatt tcagtcgatg tacacgttcg tcacatctca   1560
```

```
tctacctccc ggttttaatg aatacgattt tgtaccagag tcctttgatc gtgacaaaac   1620
aattgcactg ataatgaatt cctctggatc tactgggtta cctaagggtg tggcccttcc   1680
gcatagaact gcctgcgtca gattctcgca tgccagagat cctatttttg gcaatcaaat   1740
cattccggat actgcgattt taagtgttgt tccattccat cacggttttg gaatgtttac   1800
tacactcgga tatttgatat gtggatttcg agtcgtctta atgtatagat ttgaagaaga   1860
gctgttttta cgatcccttc aggattacaa aattcaaagt gcgttgctag taccaaccct   1920
attttcattc ttcgccaaaa gcactctgat tgacaaatac gatttatcta atttacacga   1980
aattgcttct gggggcgcac ctctttcgaa agaagtcggg gaagcggttg caaaacgctt   2040
ccatcttcca gggatacgac aaggatatgg gctcactgag actacatcag ctattctgat   2100
tacacccgag gggggatgata aaccgggcgc ggtcggtaaa gttgttccat tttttgaagc   2160
gaaggttgtg gatctggata ccgggaaaac gctgggcgtt aatcagagag gcgaattatg   2220
tgtcagagga cctatgatta tgtccggtta tgtaaacaat ccggaagcga ccaacgcctt   2280
gattgacaag gatggatggc tacattctgg agacatagct tactgggacg aagacgaaca   2340
cttcttcata gttgaccgct tgaagtcttt aattaaatac aaaggatatc aggtggcccc   2400
cgctgaattg gaatcgatat tgttacaaca ccccaacatc ttcgacgcgg gcgtggcagg   2460
tcttcccgac gatgacgccg gtgaacttcc cgccgccgtt gttgttttgg agcacggaaa   2520
gacgatgacg gaaaaagaga tcgtggatta cgtcgccagt caagtaacaa ccgcgaaaaa   2580
gttgcgcgga ggagttgtgt ttgtggacga agtaccgaaa ggtcttaccg gaaaactcga   2640
cgcaagaaaa atcagagaga tcctcataaa ggccaagaag ggcggaaagt ccaaattgta   2700
agcggccgcg ttgttaaaca gaccacaacg gtttccctct agcgggatca attccgcccc   2760
cccccctaa cgttactggc cgaagccgct tggaataagg ccggtgtgcg tttgtctata   2820
tgttattttc caccatattg ccgtcttttg gcaatgtgag ggcccggaaa cctggccctg   2880
tcttcttgac gagcattcct aggggtcttt cccctctcgc caaaggaatg caaggtctgt   2940
tgaatgtcgt gaaggaagca gttcctctgg aagcttcttg aagacaaaca acgtctgtag   3000
cgaccctttg caggcagcgg aaccccccac ctggcgacag gtgcctctgc ggccaaaagc   3060
cacgtgtata agatacacct gcaaaggcgg cacaacccca gtgccacgtt gtgagttgga   3120
tagttgtgga aagagtcaaa tggctctcct caagcgtatt caacaagggg ctgaaggatg   3180
cccagaaggt accccattgt atgggatctg atctggggcc tcggtgcaca tgctttacat   3240
gtgtttagtc gaggttaaaa aaacgtctag gccccccgaa ccacggggac gtggttttcc   3300
tttgaaaaac acgataatac catggcgcct attacggcct actcccaaca gacgcgaggc   3360
ctacttggct gcatcatcac tagcctcaca ggccgggaca ggaaccaggt cgagggggag   3420
gtccaagtgg tctccaccgc aacacaatct ttcctggcga cctgcgtcaa tggcgtgtgt   3480
tggactgtct atcatggtgc cggctcaaag acccttgccg gcccaaaggg cccaatcacc   3540
caaatgtaca ccaatgtgga ccaggacctc gtcggctggc aagcgccccc cggggcgcgt   3600
tccttgacac catgcacctg cggcagctcg gacctttact tggtcacgag gcatgccgat   3660
gtcattccgg tgcgccggcg gggcgacagc agggggagcc tactctcccc caggcccgtc   3720
tcctacttga agggctcttc gggcggtcca ctgctctgcc cctcggggca cgctgtgggc   3780
atctttcggg ctgccgtgtg cacccgaggg gttgcgaagg cggtggactt tgtacccgtc   3840
gagtctatgg gaaccactat gcggtccccg gtcttcacgg acaactcgtc ccctccggcc   3900
```

-continued

```
gtaccgcaga cattccaggt ggcccatcta cacgccccta ctggtagcgg caagagcact   3960
aaggtgccgg ctgcgtatgc agcccaaggg tataaggtgc ttgtcctgaa cccgtccgtc   4020
gccgccaccc taggtttcgg ggcgtatatg tctaaggcac atggtatcga ccctaacatc   4080
agaatcgggg taaggaccat caccacgggt gcccccatca cgtactccac ctatggcaag   4140
tttcttgccg acggtggttg ctctgggggc gcctatgaca tcataatatg tgatgagtgc   4200
cactcaactg actcgaccac tatcctgggc atcggcacag tcctggacca agcggagacg   4260
gctggagcgc gactcgtcgt gctcgccacc gctacgcctc cgggatcggt caccgtgcca   4320
catccaaaca tcgaggaggt ggctctgtcc agcactggag aaatcccctt ttatggcaaa   4380
gccatcccca tcgagaccat caaggggggg aggcacctca ttttctgcca ttccaagaag   4440
aaatgtgatg agctcgccgc gaagctgtcc ggcctcggac tcaatgctgt agcatattac   4500
cggggccttg atgtatccgt cataccaact agcggagacg tcattgtcgt agcaacggac   4560
gctctaatga cgggctttac cggcgatttc gactcagtga tcgactgcaa tacatgtgtc   4620
acccagacag tcgacttcag cctggacccg accttcacca ttgagacgac gaccgtgcca   4680
caagacgcgg tgtcacgctc gcagcggcga ggcaggactg gtaggggcag gatgggcatt   4740
tacaggtttg tgactccagg agaacggccc tcgggcatgt tcgattcctc ggttctgtgc   4800
gagtgctatg acgcgggctg tgcttggtac gagctcacgc ccgccgagac ctcagttagg   4860
ttgcgggctt acctaaacac accagggttg cccgtctgcc aggaccatct ggagttctgg   4920
gagagcgtct ttacaggcct cacccacata gacgcccatt tcttgtccca gactaagcag   4980
gcaggagaca acttccccta cctggtagca taccaggcta cggtgtgcgc cagggctcag   5040
gctccacctc catcgtggga ccaaatgtgg aagtgtctca tacggctaaa gcctacgctg   5100
cacgggccaa cgcccctgct gtataggctg ggagccgttc aaaacgaggt tactaccaca   5160
caccccataa ccaaatacat catggcatgc atgtcggctg acctggaggt cgtcacgagc   5220
acctgggtgc tggtaggcgg agtcctagca gctctggccg cgtattgcct gacaacaggc   5280
agcgtggtca ttgtgggcag gatcatcttg tccggaaagc cggccatcat tcccgacagg   5340
gaagtccttt accgggagtt cgatgagatg gaagagtgcg cctcacacct cccttacatc   5400
gaacagggaa tgcagctcgc cgaacaattc aaacagaagg caatcgggtt gctgcaaaca   5460
gccaccaagc aagcggaggc tgctgctccc gtggtggaat ccaagtggcg gaccctcgaa   5520
gccttctggg cgaagcatat gtggaatttc atcagcggga tacaatattt agcaggcttg   5580
tccactctgc ctggcaaccc cgcgatagca tcactgatgg cattcacagc ctctatcacc   5640
agcccgctca ccacccaaca taccctcctg tttaacatcc tgggggggatg ggtggccgcc   5700
caacttgctc ctcccagcgc tgcttctgct ttcgtaggcg ccggcatcgc tggagcggct   5760
gttggcagca taggccttgg gacggtgctt gtggatattt tggcaggtta tggagcaggg   5820
gtggcaggcg cgctcgtggc ctttaaggtc atgagcggcg agatgccctc caccgaggac   5880
ctggttaacc tactccctgc tatcctctcc cctggcgccc tagtcgtcgg ggtcgtgtgc   5940
gcagcgatac tgcgtcggca cgtgggccca ggggaggggg ctgtgcagtg gatgaaccgg   6000
ctgatagcgt tcgcttcgcg ggtaaccac gtctccccca cgcactatgt gcctgagagc   6060
gacgctgcag cacgtgtcac tcagatcctc tctagtctta ccatcactca gctgctgaag   6120
aggcttcacc agtggatcaa cgaggactgc tccacgccat gctccggctc gtggctaaga   6180
gatgtttggg attggatatg cacggtgttg actgatttca agacctggct ccagtccaag   6240
ctcctgccgc gattgccggg agtcccettc ttctcatgtc aacgtgggta caagggagtc   6300
```

-continued

```
tggcggggcg acggcatcat gcaaaccacc tgcccatgtg gagcacagat caccggacat   6360
gtgaaaaacg gttccatgag gatcgtgggg cctaggacct gtagtaacac gtggcatgga   6420
acattcccca ttaacgcgta caccacgggc ccctgcacgc cctccccggc gccaaattat   6480
tctagggcgc tgtggcgggt ggctgctgag gagtacgtgg aggttacgcg ggtgggggat   6540
ttccactacg tgacgggcat gaccactgac aacgtaaagt gcccgtgtca ggttccggcc   6600
cccgaattct tcacagaagt ggatggggtg cggttgcaca ggtacgctcc agcgtgcaaa   6660
cccctcctac gggaggaggt cacattcctg gtcgggctca atcaatacct ggttgggtca   6720
cagctcccat gcgagcccga accggacgta gcagtgctca cttccatgct caccgacccc   6780
tcccacatta cggcggagac ggctaagcgt aggctggcca ggggatctcc cccctccttg   6840
gccagctcat cagctagcca gctgtctgcg ccttccttga aggcaacatg cactacccgt   6900
catgactccc cggacgctga cctcatcgag gccaacctcc tgtggcggca ggagatgggc   6960
gggaacatca cccgcgtgga gtcagaaaat aaggtagtaa ttttggactc tttcgagccg   7020
ctccaagcgg aggaggatga gagggaagta tccgttccgg cggagatcct gcggaggtcc   7080
aggaaattcc ctcgagcgat gcccatatgg gcacgcccgg attacaaccc tccactgtta   7140
gagtcctgga aggacccgga ctacgtccct ccagtggtac acgggtgtcc attgccgcct   7200
gccaaggccc ctccgatacc acctccacgg aggaagagga cggttgtcct gtcagaatct   7260
accgtgtctt ctgccttggc ggagctcgcc acaaagacct tcggcagctc cgaatcgtcg   7320
gccgtcgaca gcggcacggc aacggcctct cctgaccagc cctccgacga cggcgacgcg   7380
ggatccgacg ttgagtcgta ctcctccatg cccccccttg agggggagcc gggggatccc   7440
gatctcagcg acgggtcttg gtctaccgta agcgaggagc ttaaggctag tgaggacgtc   7500
gtctgctgct cgatgtccta cacatggaca ggcgccctga tcacgccatg cgctgcggag   7560
gaaaccaagc tgcccatcaa tgcactgagc aactctttgc tccgtcacca caacttggtc   7620
tatgctacaa catctcgcag cgcaagcctg cggcagaaga aggtcacctt tgacagactg   7680
caggtcctgg acgaccacta ccgggacgtg ctcaaggaga tgaaggcgaa ggcgtccaca   7740
gttaaggcta aacttctatc cgtggaggaa gcctgtaagc tgacgccccc acattcggcc   7800
agatctaaat ttggctatgg ggcaaaggac gtccggaacc tatccagcaa ggccgttaac   7860
cacatccgct ccgtgtggaa ggacttgctg gaagacactg agacaccaat tgacaccacc   7920
atcatggcaa aaaatgaggt tttctgcgtc caaccagaga aggggggccg caagccagct   7980
cgccttatcg tattcccaga tttggggggtt cgtgtgtgcg agaaaatggc cctttacgat   8040
gtggtctcca ccctccctca ggccgtgatg ggctcttcat acggattcca atactctcct   8100
ggacagcggg tcgagttcct ggtgaatgcc tggaaagcga agaaatgccc tatgggcttc   8160
gcatatgaca cccgctgttt tgactcaacg gtcactgaga atgacatccg tgttgaggag   8220
tcaatctacc aatgttgtga cttggccccc gaagccagac aggccataag gtcgctcaca   8280
gagcggcttt acatcggggg cccccctgact aattctaaag ggcagaactg cggctatcgc   8340
cggtgccgcg cgagcggtgt actgacgacc agctgcggta ataccctcac atgttacttg   8400
aaggccgctg cggcctgtcg agctgcgaag ctccaggact gcacgatgct cgtatgcgga   8460
gacgaccttg tcgttatctg tgaaagcgcg gggacccaag aggacgaggc gagcctacgg   8520
gccttcacgg aggctatgac tagatactct gcccccccctg gggacccgcc caaaccagaa   8580
tacgacttgg agttgataac atcatgctcc tccaatgtgt cagtcgcgca cgatgcatct   8640
```

-continued

```
ggcaaaaggg tgtactatct cacccgtgac cccaccaccc cccttgcgcg ggctgcgtgg   8700
gagacagcta gacacactcc agtcaattcc tggctaggca acatcatcat gtatgcgccc   8760
accttgtggg caaggatgat cctgatgact catttcttct ccatccttct agctcaggaa   8820
caacttgaaa aagccctaga ttgtcagatc tacggggcct gttactccat tgagccactt   8880
gacctacctc agatcattca acgactccat ggccttagcg cattttcact ccatagttac   8940
tctccaggtg agatcaatag ggtggcttca tgcctcagga aacttggggt accgcccttg   9000
cgagtctgga gacatcgggc cagaagtgtc cgcgctaggc tactgtccca gggggggagg   9060
gctgccactt gtggcaagta cctcttcaac tgggcagtaa ggaccaagct caaactcact   9120
ccaatcccgg ctgcgtccca gttggattta tccagctggt tcgttgctgg ttacagcggg   9180
ggagacatat atcacagcct gtctcgtgcc cgaccccgct ggttcatgtg gtgcctactc   9240
ctactttctg taggggtagg catctatcta ctccccaacc gatgacttaa gacggggagc   9300
taaacactcc aggccaatag gccatcctgt ttttttccct tttttttttt cttttttttt   9360
tttttttttt tttttttttt tttttctcct ttttttttcc tcttttttttc cttttctttc   9420
ctttggtggc tccatcttag ccctagtcac ggctagctgt gaaaggtccg tgagccgctt   9480
gactgcagag agtgctgata ctggcctctc tgcagatcaa gtctagaaag tccctttagt   9540
gagggttaat tcaattcttg aagacgaaag ggcctcgtga tacgcctatt tttataggtt   9600
aatgtcatga taataatggt ttcttagacg tcaggtggca cttttcgggg aaatgtgcgc   9660
ggaacccccta tttgtttatt tttctaaata cattcaaata tgtatccgct catgagacaa   9720
taaccctgat aaatgcttca ataatattga aaaaggaaga gtatgagtat tcaacatttc   9780
cgtgtcgccc ttattccctt ttttgcggca ttttgccttc ctgtttttgc tcacccagaa   9840
acgctggtga aagtaaaaga tgctgaagat cagttgggtg cacgagtggg ttacatcgaa   9900
ctggatctca acagcggtaa gatccttgag agttttcgcc ccgaagaacg ttttccaatg   9960
atgagcactt ttaaagttct gctatgtggc gcggtattat cccgtgttga cgccgggcaa  10020
gagcaactcg gtcgccgcat acactattct cagaatgact tggttgagta ctcaccagtc  10080
acagaaaagc atcttacgga tggcatgaca gtaagagaat tatgcagtgc tgccataacc  10140
atgagtgata acactgcggc caacttactt ctgacaacga tcggaggacc gaaggagcta  10200
accgcttttt tgcacaacat gggggatcat gtaactcgcc ttgatcgttg ggaaccggag  10260
ctgaatgaag ccataccaaa cgacgagcgt gacaccacga tgcctgcagc aatggcaaca  10320
acgttgcgca aactattaac tggcgaacta cttactctag cttcccggca acaattaata  10380
gactggatgg aggcggataa agttgcagga ccacttctgc gctcggccct tccggctggc  10440
tggtttattg ctgataaatc tggagccggt gagcgtgggt ctcgcggtat cattgcagca  10500
ctggggccag atggtaagcc ctcccgtatc gtagttatct acacgacggg gagtcaggca  10560
actatggatg aacgaaatag acagatcgct gagataggtg cctcactgat taagcattgg  10620
taactgtcag accaagttta ctcatatata ctttagattg atttaaaact tcatttttaa  10680
tttaaaagga tctaggtgaa gatccttttt gataatctca tgaccaaaat cccttaacgt  10740
gagttttcgt tccactgagc gtcagacccc gtagaaaaga tcaaaggatc ttcttgagat  10800
cctttttttc tgcgcgtaat ctgctgcttg caaacaaaaa aaccaccgct accagcggtg  10860
gtttgtttgc cggatcaaga gctaccaact ctttttccga aggtaactgg cttcagcaga  10920
gcgcagatac caaatactgt ccttctagtg tagccgtagt taggccacca cttcaagaac  10980
tctgtagcac cgcctacata cctcgctctg ctaatcctgt taccagtggc tgctgccagt  11040
```

ggcgataagt cgtgtcttac cgggttggac tcaagacgat agttaccgga taaggcgcag 11100
cggtcgggct gaacgggggg ttcgtgcaca cagcccagct tggagcgaac gacctacacc 11160
gaactgagat acctacagcg tgagctatga gaaagcgcca cgcttcccga agggagaaag 11220
gcggacaggt atccggtaag cggcagggtc ggaacaggag agcgcacgag ggagcttcca 11280
gggggaaacg cctggtatct ttatagtcct gtcgggtttc gccacctctg acttgagcgt 11340
cgatttttgt gatgctcgtc aggggggcgg agcctatgga aaaacgccag caacgcggcc 11400
tttttacggt tcctggcctt ttgctggcct tttgctcaca tgttctttcc tgcgttatcc 11460
cctgattctg tggataaccg tattaccgcc tttgagtgag ctgataccgc tcgccgcagc 11520
cgaacgaccg agcgcagcga gtcagtgagc gaggaagcgg aagagcgcct gatgcggtat 11580
tttctcctta cgcatctgtg cggtatttca caccgcatat ggtgcactct cagtacaatc 11640
tgctctgatg ccgcatagtt aagccagtat acactccgct atcgctacgt gactgggtca 11700
tggctgcgcc ccgacacccg ccaacacccg ctgacgcgcc ctgacgggct tgtctgctcc 11760
cggcatccgc ttacagacaa gctgtgaccg tctccgggag ctgcatgtgt cagaggtttt 11820
caccgtcatc accgaaacgc gcgaggcagc tgcggtaaag ctcatcagcg tggtcgtgaa 11880
gcgattcaca gatgtctgcc tgttcatccg cgtccagctc gttgagtttc tccagaagcg 11940
ttaatgtctg gcttctgata aagcgggcca tgttaagggc ggtttttttcc tgtttggtca 12000 ctgatgcctc cgtgtaaggg ggatttctgt tcatgggggt aatgataccg atgaaacgag 12060
agaggatgct cacgatacgg gttactgatg atgaacatgc ccggttactg gaacgttgtg 12120
agggtaaaca actggcggta tggatgcggc gggaccagag aaaaatcact cagggtcaat 12180
gccagcgctt cgttaataca gatgtaggtg ttccacaggg tagccagcag catcctgcga 12240
tgcagatccg gaacataatg gtgcagggcg ctgacttccg cgtttccaga ctttacgaaa 12300
cacggaaacc gaagaccatt catgttgttg ctcaggtcgc agacgttttg cagcagcagt 12360
cgcttcacgt tcgctcgcgt atcggtgatt cattctgcta accagtaagg caaccccgcc 12420
agcctagccg ggtcctcaac gacaggagca cgatcatgcg cacccgtggc caggacccaa 12480
cgctgcccga gatgcgccgc gtgcggctgc tggagatggc ggacgcgatg gatatgttct 12540
gccaagctaa gctgcctgca ggtaatacga ctcactata 12579

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
aagcgaggag cttaaggcyr gtgaggacgt 30

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
agctccccgt cttaagtcay cggttgggg 29

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
gggacctcac cgctcatgat 20

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
ctcaccgctc atgatcttga atgc 24

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
cggaggtcat tacgtgcaaa tg 22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
cgtgcaaatg gccatcatca ag 22

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
gcgcttactg gcacctatg 19

<210> SEQ ID NO 35
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
aggcacgccg atgtcat 17

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
cgggaccttg gtgctctt 18

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
cggcactgtc cttgacca 18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
gagtcgaagt cgccggta 18

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
ccgagactac agttaggcta cg 22

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
gcatgtcatg atgtatttgg tg 22

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
acgaggacct tccccagt 18

<210> SEQ ID NO 42

<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 42
gctgccggtg ggagcatg 18

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 43
gagcatgcag gtgggccac 19

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 44
gcggcgacat catcaacgg 19

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 45
catcaacggc ttgcccgtct c 21

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 46
gacctttacc tggtcacgag 20

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 47
gctgtccaga acttgcagtc tgtc 24

<210> SEQ ID NO 48
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48

cctttggcaa gcactgcgtg                                             20


<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49

ctgcgtggtc atagtgggca g                                           21


<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50

tgtcttgtcc gggaagccgg                                             20


<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51

cgtcactgcc atactcagca                                             20


<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52

cgtcccgttt ttgacatg                                               18


<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53

tgactcaacc ctggtgatgt t                                           21


<210> SEQ ID NO 54
<211> LENGTH: 17
<212> TYPE: DNA
```

-continued

<213> ORGANISM: Artificial Sequence
<220> FEATURE:
<223> OTHER INFORMATION: Description of Artificial Sequence: Synthetic
primer

<400> SEQUENCE: 54
cggtggtcct caccgaa 17

<210> SEQ ID NO 55
<211> LENGTH: 15
<212> TYPE: DNA
<213> ORGANISM: Artificial Sequence
<220> FEATURE:
<223> OTHER INFORMATION: Description of Artificial Sequence: Synthetic
primer

<400> SEQUENCE: 55
ttgtccggga agccg 15

<210> SEQ ID NO 56
<211> LENGTH: 16
<212> TYPE: DNA
<213> ORGANISM: Artificial Sequence
<220> FEATURE:
<223> OTHER INFORMATION: Description of Artificial Sequence: Synthetic
primer

<400> SEQUENCE: 56
tggcaagcac tgcgtg 16

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 57
ttgacgtcca tgctcactg 19

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 58
aggccggagt gtttacccca ac 22

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 59
ggagtgttta ccccaacctt ca 22

<210> SEQ ID NO 60
<211> LENGTH: 23
<212> TYPE: DNA
<213> ORGANISM: Artificial Sequence -continued
<220> FEATURE:
<223> OTHER INFORMATION: Description of Artificial Sequence: Synthetic
primer

<400> SEQUENCE: 60
tgactatgaa ccacctgtgg tcc 23

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 61
cacctgtggt ccatggctg 19

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 62
catcaactcc gtgtggaaag 20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 63
cagcgggtat catacgagaa 20

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 64
gcaccatgct cgtgtgtg 18

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 65
gtcatcagta tcatcctcgc c 21

<210> SEQ ID NO 66
<211> LENGTH: 19
<212> TYPE: DNA
<213> ORGANISM: Artificial Sequence
<220> FEATURE:

<223> OTHER INFORMATION: Description of Artificial Sequence: Synthetic primer

<400> SEQUENCE: 66
cgactccatg gtcttagcg 19

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
gagcgccttc tgtttgaatt g 21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
ctgtttgaat tgctcggcga g 21

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
atgcatgctg gtgcggaa 18

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
tggtgcggaa agtcgctgg 19

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
ggtcattatg tccaaatggc 20

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
cggcagctcg gaccttta 18

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
cacttggaat gtctgcggta c 21

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
gatgagtgcc actcaactga ct 22

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
cgtctgttgc cacgacaa 18

<210> SEQ ID NO 76
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
ctatgacgcg ggctgtg 17

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
agccgtatga gacacttcca c 21

<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
gcatagacca tgttgtggtg acg 23

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 79
gtgacgcagc aaagagttgc tca 23

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 80
agcgtggtca ttgtgggcag 20

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 81
gggcaggatc atcttgtccg g 21

<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 82
ttcccaaggc ctatgctg 18

<210> SEQ ID NO 83
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 83
ggatgaaccg gctgatagc 19

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 84
atggaaccgt ttttgacatg t 21

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 85
gggcatgacc actgacaac 19

<210> SEQ ID NO 86
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 86
ccacaggagg ttggcct 17

<210> SEQ ID NO 87
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 87
cacgggtgcc cattgc 16

<210> SEQ ID NO 88
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 88
aaggagatga aggcgaagg 19

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 89
catcacggcc tgaggaag 18

<210> SEQ ID NO 90
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 90
tcgctcacag agcggct 17

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 91
tggaggagca tgatgttatc a 21

<210> SEQ ID NO 92
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 92
cgactccatg gtcttagcg 19

<210> SEQ ID NO 93
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 93
gtaggtggac tggcacttac atctatga 28

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 94
cgctattagc ccttggtagg tgg 23

<210> SEQ ID NO 95
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 95
aaatgcccgc accataccc 19

<210> SEQ ID NO 96
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 96

-continued

```
ggcttctcgc cagacatgat ctt                                              23


<210> SEQ ID NO 97
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97

cacggacttc ccgtgtc                                                     17


<210> SEQ ID NO 98
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98

tgccagttgg ggcatg                                                      16


<210> SEQ ID NO 99
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99

tccgggcagc tgtgtg                                                      16


<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100

cgtcttgagg gacagtctgt g                                                21


<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101

ggagggtgag atccccttct a                                                21


<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102

gaagttccac atgtgtttgg c                                                21
```

<210> SEQ ID NO 103
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 103
gtagtgctct gtgagtgcta cg 22

<210> SEQ ID NO 104
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 104
atcttacacg gactccccgt gtc 23

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 105
atgcggggac atcttacacg g 21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 106
tggggcatgc aagtacccga c 21

<210> SEQ ID NO 107
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 107
cactgccagt tggggcatg 19

<210> SEQ ID NO 108
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 108
tacggatacc atactttgtg agggc 25

<210> SEQ ID NO 109
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 109
tctctgctac ggataccata ctttg 25

<210> SEQ ID NO 110
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 110
tccaccagta tcttacccag gccta 25

<210> SEQ ID NO 111
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 111
acgtccacca gtatcttacc ca 22

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 112
acgagtgtgt accctggtga 20

<210> SEQ ID NO 113
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 113
gacccctgta cctgcgg 17

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 114
gcaagtagcc cacctggtaa g 21

-continued

<210> SEQ ID NO 115
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 115
gccattcagt ggacgccac 19

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 116
ccttgagttg gtataacgga gac 23

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 117
gctctgtgag tgctatgatg c 21

<210> SEQ ID NO 118
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 118
ggtaggacca gtcagtgtag gttt 24

<210> SEQ ID NO 119
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 119
caacgaagcc agtggctc 18

<210> SEQ ID NO 120
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 120
tgcatggcct cccggtttc 19

<210> SEQ ID NO 121

<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 121
catgtggaga catcctgcat gg 22

<210> SEQ ID NO 122
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 122
ttggtgcatg caagtagccc ac 22

<210> SEQ ID NO 123
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 123
cgctgcctgt tggtgcatg 19

<210> SEQ ID NO 124
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 124
cttctgtacc atcagagtac ctgatca 27

<210> SEQ ID NO 125
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 125
gtgagccttc tgtaccatca gagtac 26

<210> SEQ ID NO 126
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 126
atggagtgta gctagggttt gcc 23

<210> SEQ ID NO 127
<211> LENGTH: 23

<212> TYPE: DNA
<213> ORGANISM: Artificial Sequence
<220> FEATURE:
<223> OTHER INFORMATION: Description of Artificial Sequence: Synthetic
primer

<400> SEQUENCE: 127
tgtagctagg gtttgccgct cta 23

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 128
gaaccaccca ctgtcctagg 20

<210> SEQ ID NO 129
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 129
gcacactatg actcagtctt gca 23

<210> SEQ ID NO 130
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 130
catcttttcg cacaccctg 19

<210> SEQ ID NO 131
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 131
tacgtaggag ggcccatg 18

<210> SEQ ID NO 132
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 132
agcgctaccg atacgtttg 19

<210> SEQ ID NO 133
<211> LENGTH: 18
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 133

ccggccataa ttgaaagg                                                    18


<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134

atgctcgtgc gctccgtgat                                                  20


<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135

ctttgcatgc tcgtgcgctc                                                  20


<210> SEQ ID NO 136
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136

tactatgggc tcaatgacag cttgttg                                          27


<210> SEQ ID NO 137
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137

ggtagctact atgggctcaa tgacagc                                          27


<210> SEQ ID NO 138
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138

tacttccaga tgatcatact gagc                                             24


<210> SEQ ID NO 139
<211> LENGTH: 21
<212> TYPE: DNA
<213> ORGANISM: Artificial Sequence
```

<220> FEATURE:
<223> OTHER INFORMATION: Description of Artificial Sequence: Synthetic primer

<400> SEQUENCE: 139
acttatactt ggttacccgc g 21

<210> SEQ ID NO 140
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 140
tcttaccgct gccggtc 17

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 141
tcttagatca ggctgagacg g 21

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 142
ctgttgttgg tatgacggac a 21

<210> SEQ ID NO 143
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 143
agcccgctga gaccaca 17

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 144
atgtagtgtt ggcttaagcc g 21

<210> SEQ ID NO 145
<211> LENGTH: 17
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 145
ctgccggtcg gggcatg 17

<210> SEQ ID NO 146
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
ggtcggggca tgaaggtatc ctac 24

<210> SEQ ID NO 147
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
cttgcggaga tattctttgc gg 22

<210> SEQ ID NO 148
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
ttgcgggctg cccgtctc 18

<210> SEQ ID NO 149
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
cgacgttgaa tagactaggt tatgatgtct 30

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
ccctagcggc ctactgcttg 20

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 151
ggcctactgc ttgtcagtcg g 21

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 152
gcctactgct tgtcagtcgg 20

<210> SEQ ID NO 153
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 153
atacccccta tggcagcg 18

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 154
acagtggatg aacaggctca t 21

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 155
tgacaggaaa tgaagggcag 20

<210> SEQ ID NO 156
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 156
tgaagtggat ggggtgaga 19

<210> SEQ ID NO 157
<211> LENGTH: 18
<212> TYPE: DNA
<213> ORGANISM: Artificial Sequence
<220> FEATURE:
<223> OTHER INFORMATION: Description of Artificial Sequence: Synthetic primer -continued

<400> SEQUENCE: 157
tgaggcctat gcgtctgg 18

<210> SEQ ID NO 158
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 158
caccaactgt cgatggatg 19

<210> SEQ ID NO 159
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 159
ttatgatgtc tcaacaagga gttgctga 28

<210> SEQ ID NO 160
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 160
agtgttatct taccagctca ccgagc 26

<210> SEQ ID NO 161
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 161
atcttaccag ctcaccgagc tggc 24

<210> SEQ ID NO 162
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 162
gtatcctcca gcccttccta tctg 24

<210> SEQ ID NO 163
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 163
cagcccttcc tatctgggct ag 22

<210> SEQ ID NO 164
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 164
tcgggtatag tgcgaagga 19

<210> SEQ ID NO 165
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 165
cttcagcaga cgttcgacc 19

<210> SEQ ID NO 166
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 166
tacatcaagg ccacagcg 18

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 167
ctggagtgtg acgagctgtt 20

<210> SEQ ID NO 168
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 168
cttggagaca tcgggcac 18

<210> SEQ ID NO 169
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 169
gcgcgtccct tacttcgtga g 21

<210> SEQ ID NO 170
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 170
gctcctgcgc gtcccttac 19

<210> SEQ ID NO 171
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 171
gtagccagcg aggatgtcca ctag 24

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 172
catctcgccg ctcatgatct t 21

<210> SEQ ID NO 173
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 173
gcgtccctta cttcgtgag 19

<210> SEQ ID NO 174
<211> LENGTH: 16
<212> TYPE: DNA
<213> ORGANISM: Artificial Sequence
<220> FEATURE:
<223> OTHER INFORMATION: Description of Artificial Sequence: Synthetic
primer

<400> SEQUENCE: 174
ccgtgcgcag gagagg 16

<210> SEQ ID NO 175
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 175
cacggtcttg gaccaagc 18

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 176
gcctggtacg aactgacacc 20

<210> SEQ ID NO 177
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 177
gccacttcct gttggtgc 18

<210> SEQ ID NO 178
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 178
ctgagtcaaa gtcgccggt 19

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 179
gacatgcagg ccatgatgta 20

<210> SEQ ID NO 180
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 180
taaggggatt acctgtctcg gc 22

<210> SEQ ID NO 181
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 181
agttgtgttc acgcccatgg ag 22

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 182
gggactttgg tgctcttgcc 20

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 183
tcgatgccat atgccttgga c 21

<210> SEQ ID NO 184
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 184
tttcagtggg cagcgtggt 19

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 185
agcgtggtga tcgtcgggag 20

<210> SEQ ID NO 186
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 186
cctgcaggcg gtcgaagg 18

<210> SEQ ID NO 187
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 187
cgaaggtcac cttcttctgc cg 22

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 188
agacatgagg gaagcaatgg 20

<210> SEQ ID NO 189
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 189
tgtgcagtgg atgaaccg 18

<210> SEQ ID NO 190
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 190
actctgcgaa cctccacg 18

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 191
gttgacagac ccatcacaca t 21

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 192
tcgtctgtct caaccctggt 20

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 193
tcttactcgt caatgcctcc 20

<210> SEQ ID NO 194
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 194
cggggtaaca caagataaca tcaag 25

<210> SEQ ID NO 195
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 195
accctaaggt cggagtgtta agct 24

<210> SEQ ID NO 196
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 196
acaagataac atcaagtgcc cctg 24

<210> SEQ ID NO 197
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 197
aaggtcggag tgttaagctg ccta 24

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 198
cttattcgtc aatgcctcca c 21

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 199
atcatggcca aaaatgaggt 20

<210> SEQ ID NO 200

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 200
gccttcacgg aggctatgac 20

<210> SEQ ID NO 201
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 201
tgtggcatat acctctttaa ctgg 24

<210> SEQ ID NO 202
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 202
ggagtcaaag cagcggg 17

<210> SEQ ID NO 203
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 203
caggaattga ctggagtgtg tc 22

<210> SEQ ID NO 204
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 204
gcacaggagt aaatagcggg 20

<210> SEQ ID NO 205
<211> LENGTH: 329
<212> TYPE: DNA
<213> ORGANISM: Hepatitis C virus

<400> SEQUENCE: 205
agtcaccgag aatgatatcc gtgttgagga gtcaatttac caatgctgtg acttggcccc 60
cgaagccaaa caggccataa ggtcgctcac agagcggctt tayatcgggg gtcccctgac 120
taattcaaaa gggcagaact gcggttatcg ccggtgccgc gcgagcggcg tgctgacgac 180
cagctgcggt aataccctca cctgttactt gaaggccacc gcggcctgtc gagctgcaaa 240
gctccaggac tgcacgatgc tcgtgtgcgg ggacgacctt gtcgttatct gtgaaagcgc 300
gggaacccaa gaggacgcgg cgaacctac 329

<210> SEQ ID NO 206
<211> LENGTH: 329
<212> TYPE: DNA
<213> ORGANISM: Hepatitis C virus

<400> SEQUENCE: 206
tgtcacygag agtgacatcc gygttgagga gtcaatctac caatgttgtg acttggcccc 60
cgaagccaga caggccataa agtcgctcac agagcggctt tayatcgggg gtcccctgac 120
taaytcaaaa ggrcagaact gcggytatcg ccggtgccgc gcgagcggcg tgctgacgac 180
tagctgcggy aacaccctca cmtgttacyt gaaggcctct gcagcctgtc gagctgcraa 240
gctccaggac tgcacgatgc tcgtgtgcgg ggacgacctt gtcgttatct gcgagagtgc 300
tgggacccag gaggacgygg cgagcctac 329

<210> SEQ ID NO 207
<211> LENGTH: 329
<212> TYPE: DNA
<213> ORGANISM: Hepatitis C virus

<400> SEQUENCE: 207
ggtcactgag aatgacattc gtgtcgagga gtcgatctac caatgctgtg acttggcccc 60
cgaagccaga cargccataa ggtcgctcac ggagcggctt tatatcgggg gtcccctgac 120
taattcaaaa gggcagaact gcggttatcg ccggtgccgc gcgagcggtg tactgacgac 180
cagctgtggt aataccctca catgttactt gaaggcctct gcggcctgtc gagctgccaa 240
gctccaggac tgcacgatgc tcgtgaacgg agacgacctt gtcgttatct gtgagagcgc 300
gggaacccaa raggacgcag cgaacctac 329

<210> SEQ ID NO 208
<211> LENGTH: 329
<212> TYPE: DNA
<213> ORGANISM: Hepatitis C virus

<400> SEQUENCE: 208
rgtcaccgag agkgacatcc gtgttgagga gtcratytac caatgttgtg acttggcccc 60
cgaagccaga caggccataa agtcgctcac rgagcggctc tatatcgggg gccccctgac 120
taattcaaaa gggcagaact gcggttatcg ccggtgccgc gccagcggcg trctgacgac 180
cagctgcggt aataccctca catgttactt gaaggcctct gcggcctgtc gagctgcaaa 240
gctccaggac tgcacgatgc ttgtgtgygg agacgaccty gtcgttatct gtgagagcgc 300
ggggacccag gaggacgcgg cgagcctac 329

<210> SEQ ID NO 209
<211> LENGTH: 329
<212> TYPE: DNA
<213> ORGANISM: Hepatitis C virus

<400> SEQUENCE: 209
ggtcactgag agtgayatcc gtgtygagga gtcaatatac caatgttgtg acttggcccc 60
cgaagccaga caggccataa agtcgctcac agagcggctc tatgttgggg gtcccctgac 120
taaytcaaaa gggcagaact gcggttatcg ccggtgccgc gccagcggcg tgctgacgac 180
cagctgcggt aataccctca cttgttactt gaaagcctct gcrgcctgtc gagctgcgaa 240
gctccaggac tgcacgatgc tcgtgtgtgg agacgacctt gtcgttatct gcgaaagcgc 300
gggaacccag gaggacgcgg cgagcctac 329

<210> SEQ ID NO 210
<211> LENGTH: 329
<212> TYPE: DNA
<213> ORGANISM: Hepatitis C virus

<400> SEQUENCE: 210
agtcactgag agtgacatcc gcgttgagga gtcaatctac caatgttgtg acttggcccc 60
cgaagccaaa caggccataa agtcgctcac agagcggctt tacatcgggg gtcccctgac 120
taattcaaaa gggcagaact gcggctatcg ccggtgccgc gccagcggcg tactgacgac 180
cagctgtggt aataccctca catgttactt gaaagcctct gcggcctgtc gagctgcaaa 240
gctccaggac tgcacgatgc tcgtgtgcgg agacgacctt gtcgttatct gtgagagcgc 300
gggaacccag gaggacgcgg cgagcctac 329

<210> SEQ ID NO 211
<211> LENGTH: 329
<212> TYPE: DNA
<213> ORGANISM: Hepatitis C virus

<400> SEQUENCE: 211
ggtcactgag agtgatatcc gtactgagga gtctatttac caatgttgtg acctggcccc 60
cgaagctaga caagtcataa ggtcgctcac agagcggctt tayatygggg gcccccctgac 120 yaattcaaaa gggcagaact gcggttatcg ccggtgccgy gcgagcggcg tgctgacgac 180
tagctgcggt aataccctca catgttactt gaaggcctct gcggcctgtc gagctgcaaa 240
gctccgggac tgcacgatgc tcgtgtgcgg agacgacctc gtcgttatct gtgaaagcgc 300
ggggacccag gaggacgcgg ctagcctac 329

<210> SEQ ID NO 212
<211> LENGTH: 329
<212> TYPE: DNA
<213> ORGANISM: Hepatitis C virus

<400> SEQUENCE: 212
agtcaccgag aatgatatcc gtgttgagga gtcaatttac caatgctgtg acttggcccc 60
cgaagccaaa caggccataa ggtcgctcac agagcggctt tayatcgggg gtcccctgac 120
taattcaaaa gggcagaact gcggttatcg ccggtgccgc gcgagcggcg tgctgacgac 180
cagctgcggt aataccctca cctgttactt gaaggccacc gcggcctgtc gagctgcaaa 240
gctccaggac tgcacgatgc tcgtgtgcgg ggacgacctt gtcgttatct gtgaaagcgc 300
gggaacccaa gaggacgcgg cgaacctac 329

<210> SEQ ID NO 213
<211> LENGTH: 329
<212> TYPE: DNA
<213> ORGANISM: Hepatitis C virus

<400> SEQUENCE: 213
ggtcacygag agygacatcc gtactgagga gtcaatttac caatgttgtg acttggcccc 60
cgaagccaga caggttataa ggtcgctcac agagcggctt tatatcgggg gtcctytgac 120
taattcaaaa gggcagaact gcggctatcg ccggtgtcgc gcaagcggcg tgctgacgac 180
cagctgcggc aataccctca catgttacct gaaggccact gcagcctgtc gagctgcgaa 240
gctccaggac tgcacaatgc ttgtgtgtgg ggacgacctt gtcgtyatct gtgagagcgc 300
ggggacccaa gaggacgcag cgagcctac 329

<210> SEQ ID NO 214
<211> LENGTH: 329
<212> TYPE: DNA
<213> ORGANISM: Hepatitis C virus

<400> SEQUENCE: 214
ggtcactgag aatgacatyc gtgttgagga gtcaatttac caatgttgtg acttggcycc 60
cgaagccaga caggycataa ggtcgctcac agagcggctt tayatcgggg gtccyctaac 120
caattcaaaa gggcaaaact gcggttatcg ccggtgtcgc gcragcggcg tgctgacgac 180
tagctgcggc aayaccctta catgttactt gaargcctct gcrgcctgtc gagctgcgaa 240
gctccaggac tgcacgatgc tcgtgtgcgg agacgacctc gtcgttatct gtgagagcgc 300
ggggacccac gaggatgcgg cgagcctac 329

<210> SEQ ID NO 215
<211> LENGTH: 543
<212> TYPE: DNA
<213> ORGANISM: Hepatitis C virus

<400> SEQUENCE: 215
gcgcctatca cggcctacgc ccarcaaaca cggggcttgt ttggctgtat catcactagc 60
ctcacaggcc gggacaagaa ccaggtcgag ggggaggtcc aagtggtttc caccgccaca 120
caatctttcc tggcgacctg tgtcaacggt gtktgttgga ctgtcttcca cggcgccggt 180
tcaaagaccc tggctggccc aaagggycca atcacccaaa tgtacaccaa tgtagaccag 240
gacctcgtcg gctggccggc ccccccyggg gcgcgctctc tracaccatg cacctgtggc 300
agctcggacc tttacttggt cacgaggcat gctgatgtta tcccggtgcg ccggcggggc 360
gacagtaggg gragcctact ctcccccagg cctgtgtcct acttaaaagg ctcttcgggt 420
ggwccrctgc tctgcccctc ggggcacgct gtgggcgtct tccgggctgc tgtgtgcacc 480
cggggggtcg cgaaggcggt ggactttgta cccgtagagt ctatggagac taccatgcgg 540
tcc 543

<210> SEQ ID NO 216
<211> LENGTH: 543
<212> TYPE: DNA
<213> ORGANISM: Hepatitis C virus

<400> SEQUENCE: 216
gcgcccatca cggcctacgc ccaacaracg aggggcctac ttggctgtat catcaccagc 60
ctcacaggcc gggacaagaa ccaggtygag ggggaggttc aggtggtctc cactgcaaca 120
cagtccttcc tggcracttg catcaacggc gtgtgttgga ctgtctttca tggagccggc 180
tctaagaccc tagccggccc aaaggggccg atcacccaga tgtacaccaa tgtagaccag 240
gacctcgtcg gctggcaagc gcccccyggg gcgcgttcct tgacaccgtg cacctgcggc 300
agctcggacc tttacttggt cacgaggcat gccgatgtca ttccggtgcg ccggcgaggt 360
gacagcaggg ggagcttgct ctcccccggg cccatttcyt acttraaagg ctcttcgggt 420
ggtccrytgc tctgcccctc ggggcacgcy gtgggcatct tccgggctgc cgtgtgcacy 480
cggggggttg ccaaggcrgt ggattttgta cccgttgagt ctatggaaac tacyatgcgg 540
tcc 543

<210> SEQ ID NO 217
<211> LENGTH: 543
<212> TYPE: DNA
<213> ORGANISM: Hepatitis C virus

<400> SEQUENCE: 217
gcgcctatta cggcctacgc ccaacagacg aggggcctat taggctgcat catcactagc 60
ctcacaggcc gagacaagaa ccaggtcgag ggggaggttc aggtggtttc taccgcaaca 120
caatccttcc tagcgacttg cgtcaacggc gtgtgttgga ctgtctatca tggcgccggc 180
tctaagacct tagccggccc aaaggggcct gtcacccaaa tgtacaccaa tgtagaccaa 240
gacctcgtcg gctggccagc gccccccggg gcgcgttcct tgacaccatg tacttgcggc 300
agttcggacc tttacttggt cacgagacat gccgatgtca ttccggtgcg ccggcggggc 360
gacagcaggg ggagcctgct ctcccccagg cctgtctcct atttgaaggg ctcttcgggt 420
ggtccactgc tctgcccttc agggcacgcc gtgggcatct tccgggctgc cgtgtgcacc 480
cgaggggttg ccaaggcggt ggactttgtg cccgtcgagt ccatggaaac tactatgcgg 540
tct 543

<210> SEQ ID NO 218
<211> LENGTH: 543
<212> TYPE: DNA
<213> ORGANISM: Hepatitis C virus

<400> SEQUENCE: 218
gcgcctatca cggcttactc ccaacagacg cggggcctgc ttggctgcat catcacyagc 60
ctcacaggca grgacaagaa ccaggtcgag gggaagtcc aagtggtttc caccgcaaca 120
caatcttttc tagcgacctg tgtcaacggc gtgtgttgga ctgttttcca tggcgccggc 180
tcaaaaacct tagccggccc aaagggcccg gtcacccaaa tgtacaccaa tgtagaccag 240
gacctcgtcg gctggcaggc gcctaccggg gcgcgttctt taacaccatg cacctgcggc 300
agctcggacc tttatttggt cacgaggcat gctgatgtca ttccggtgcg ccggcggggc 360
gacagccggg ggagtctact ctcccccagg cccgtctcct acttgaaggg ctcctcgggt 420
ggtccgctgc tctgcccctc ggggcatgca gtgggcatct tccgggctgc cgtgtgcacc 480
cggggggtcg caaaggcagt ggacttcata cccgttgagt ctatggaaac tactatgcgg 540
tcc 543

<210> SEQ ID NO 219
<211> LENGTH: 543
<212> TYPE: DNA
<213> ORGANISM: Hepatitis C virus

<400> SEQUENCE: 219
gcgcctatca cagcctactc ccaacagacg cggggcctgc ttggctgcat catcactagc 60
ctcacaggcc gggacaagaa ccaggtcgag ggggaggttc aagtggtttc caccgcgaca 120
caatctttcc tggcgacctg cgtcaacggc gtgtgttgga ctgtctacca tggtgccggc 180
tcgaagaccc tagccggccc aaagggcccg atcacccaaa tgtacaccaa tgtagaccag 240
gacctcgtcg gctggccggc gccctccgga gcgcgctcct tgacaccgtg cacctgcggc 300
agctcagacc tytacttggt cacgaggcat gctgatgttg ttccggtgcg ccggcggggc 360

-continued

```
gacagcaggg gaagcctact ctcccccagg cccatttcct acttgaaggg ctcttcgggt    420

ggcccgctgc tttgcccctc ggggcacgcg gtgggcatct tccgggctgc tgtatgcacc    480

cggggggtcg cgaaggcggt ggactttgta cccgttgagt ctatggaaac caccatgcgg    540

tct                                                                  543
```

<210> SEQ ID NO 220
<211> LENGTH: 543
<212> TYPE: DNA
<213> ORGANISM: Hepatitis C virus

<400> SEQUENCE: 220

```
gcgcctatta cggcctactc ccaacagacg cgaggcctac ttggctgcat catcactagc     60

ctcacaggcc gggacaggaa ccaggtcgag gggaggtcc aagtggtctc caccgcaaca    120

caatctttcc tggcgacctg cgtcaatggc gtgtgttgga ctgtctatca tggtgccggc    180

tcaaagaccc ttgccggccc aaagggccca atcacccaaa tgtacaccaa tgtggaccag    240

gacctcgtcg gctggcaagc gccccccggg gcgcgttcct tgacaccatg cacctgcggc    300

agctcggacc tttacttggt cacgaggcat gccgatgtca ttccggtgcg ccggcggggc    360

gacagcaggg ggagcctact ctcccccagg cccgtctcct acttgaaggg ctcttcgggc    420

ggtccactgc tctgcccctc ggggcacgct gtgggcatct ttcgggctgc cgtgtgcacc    480

cgaggggttg cgaaggcggt ggactttgta cccgtcgagt ctatggaaac cactatgcgg    540

tcc                                                                  543
```

<210> SEQ ID NO 221
<211> LENGTH: 181
<212> TYPE: PRT
<213> ORGANISM: Hepatitis C virus

<400> SEQUENCE: 221

```
Ala Pro Ile Thr Ala Tyr Ser Gln Gln Thr Arg Gly Leu Leu Gly Cys
1               5                   10                  15

Ile Ile Thr Ser Leu Thr Gly Arg Asp Arg Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Tyr His Gly Ala Gly Ser Lys Thr Leu
    50                  55                  60

Ala Gly Pro Lys Gly Pro Ile Thr Gln Met Tyr Thr Asn Val Asp Gln
65                  70                  75                  80

Asp Leu Val Gly Trp Gln Ala Pro Pro Gly Ala Arg Ser Leu Thr Pro
                85                  90                  95

Cys Thr Cys Gly Ser Ser Asp Leu Tyr Leu Val Thr Arg His Ala Asp
            100                 105                 110

Val Ile Pro Val Arg Arg Arg Gly Asp Ser Arg Gly Ser Leu Leu Ser
        115                 120                 125

Pro Arg Pro Val Ser Tyr Leu Lys Gly Ser Ser Gly Gly Pro Leu Leu
    130                 135                 140

Cys Pro Ser Gly His Ala Val Gly Ile Phe Arg Ala Ala Val Cys Thr
145                 150                 155                 160

Arg Gly Val Ala Lys Ala Val Asp Phe Val Pro Val Glu Ser Met Glu
                165                 170                 175

Thr Thr Met Arg Ser
            180
```

<210> SEQ ID NO 222
<211> LENGTH: 181
<212> TYPE: PRT
<213> ORGANISM: Hepatitis C virus
<220> FEATURE:
<221> NAME/KEY: MOD_RES
<222> LOCATION: (104)..(104)
<223> OTHER INFORMATION: Any amino acid

<400> SEQUENCE: 222

Ala Pro Ile Thr Ala Tyr Ser Gln Gln Thr Arg Gly Leu Leu Gly Cys
1 5 10 15

Ile Ile Thr Ser Leu Thr Gly Arg Asp Lys Asn Gln Val Glu Gly Glu
20 25 30

Val Gln Val Val Ser Thr Ala Thr Gln Ser Phe Leu Ala Thr Cys Val
35 40 45

Asn Gly Val Cys Trp Thr Val Tyr His Gly Ala Gly Ser Lys Thr Leu
50 55 60

Ala Gly Pro Lys Gly Pro Ile Thr Gln Met Tyr Thr Asn Val Asp Gln
65 70 75 80

Asp Leu Val Gly Trp Pro Ala Pro Ser Gly Ala Arg Ser Leu Thr Pro
85 90 95

Cys Thr Cys Gly Ser Ser Asp Xaa Tyr Leu Val Thr Arg His Ala Asp
100 105 110

Val Val Pro Val Arg Arg Arg Gly Asp Ser Arg Gly Ser Leu Leu Ser
115 120 125

Pro Arg Pro Ile Ser Tyr Leu Lys Gly Ser Ser Gly Gly Pro Leu Leu
130 135 140

Cys Pro Ser Gly His Ala Val Gly Ile Phe Arg Ala Ala Val Cys Thr
145 150 155 160

Arg Gly Val Ala Lys Ala Val Asp Phe Val Pro Val Glu Ser Met Glu
165 170 175

Thr Thr Met Arg Ser
180

<210> SEQ ID NO 223
<211> LENGTH: 1776
<212> TYPE: DNA
<213> ORGANISM: Hepatitis C virus

<400> SEQUENCE: 223
tcgatgtcct acacgtggac gggcgccctg atcacgccgt gcgccgcgga ggaaagcaag 60
ctgcctatca atgcattgag caactcactg ctgcgtcacc acaatatggt ttatgctaca 120
acatcccgca gcgcaagcca gcggcagaag aaggtcactt ttgacagact gcaagtcctg 180
gacgaccact accgggacgt gctcaaggag atgaaggcga aggcgtccac agttaaggct 240
aagcttctat ctgtagagga agcctgtaaa ctgacgcccc cacattcggc cagatccaaa 300
tttggctayg gggcaaagga cgtccggaac ctatccagca aggccgttaa ccacatccgc 360
tccgtgtgga aggacttgct ggaagacact gagacaccaa ttgacaccac catcatggca 420
aaaaacgagg tyttctgcgt ccaaccagag aaaggaggcc gcaagccagc tcgccttatc 480
gtgttcccag acttgggagt tcgtgtgtgc gagaaaatgg ccctttacga cgtggtctcc 540
actcttcctc aagccgtgat gggctcctca tatggattcc agtactctcc tggacagcgg 600
gttgaattcc tggtgaatgc ctggaagtcg aagaagaacc ctatgggctt cgcatatgac 660
acccgctgtt ttgactcaac agtcactgag agtgacatcc gcgttgagga gtcaatctac 720
caatgttgtg acttggcccc cgaagccaaa caggccataa agtcgctcac agagcggctt 780
tacatcgggg gtcccctgac taattcaaaa gggcagaact gcggctatcg ccggtgccgc 840
gccagcggcg tactgacgac cagctgtggt aataccctca catgttactt gaaagcctct 900
gcggcctgtc gagctgcaaa gctccaggac tgcacgatgc tcgtgtgcgg agacgacctt 960
gtcgttatct gtgagagcgc gggaacccag gaggacgcgg cgagcctacg agtcttcacg 1020
gaggctatga ctaggtactc cgcccccccc ggggacccgc cccagccaga gtacgacttg 1080
gagttgataa catcatgctc ctccaacgtg tcggtcgcgc acgatgcatc cggcaaacgg 1140
gtgtattacc tcacccgtga ccccaccacc cccctcgcga gggctgcgtg ggaaacagct 1200
agacacactc cagttaattc ttggctaggc aacatcatta tgtatgcgcc caccctgtgg 1260
gcaaggatga ttttgatgac tcacttcttc tccatccttc tagctcaaga acaacttgaa 1320
aaagccctgg attgtcagat ctacggggcc tgctactcca ttgagccact tgacctacct 1380
cagatcattc arcgactcca tggtcttagc gcattttcac tccacagtta ctctccaggt 1440
gagatcaata gggtggcttc atgcctcagg aaacttgggg taccgccctt gcgagtctgg 1500
agacatcggg ccagaagtgt ccgcgctaag ctactgtccc aggggggggag ggctgccatt 1560 tgtggcaagt acctcttcaa ctgggcrgta aggaccaagc tcaaactcac tccaatcccg 1620
gcagcgtccc agttggactt gtccgactgg ttcgttgccg gctacagcgg gggagacata 1680
tatcacagcc tgtctcgtgc ccgaccccgc tggttcctgt ggtgcctact cctgctttct 1740
gcgggggtag gcatctactt gctccccaac cgatga 1776

<210> SEQ ID NO 224
<211> LENGTH: 1776
<212> TYPE: DNA
<213> ORGANISM: Hepatitis C virus

<400> SEQUENCE: 224
tcgatgtcct acacatggac aggcgcttta atcacaccat gcgctgcgga ggaaagcaag 60
ctgcccatca acgcgctgag caactccctg ctgcgycacc acaatatggt gtatgccaca 120
acatcccgca gcgcaagcca rcggcagaag aargtcactt ttgacagact gcaagtcctg 180
gacgaycatt accgggacgt rctcaaggag gtgaaggcga aggcgtccac agttaaggcy 240
aaacttctat ccgtagaaga ggcctgcaaa ctsacgcccc cacactcagc caaatccaar 300
tttggctatg gggcraagga cgtccggaac ctatccagca aggccgtyaa ccacatccac 360
tccgtgtgga aggacttgct ggaggacact gaaacaccaa ttgacactac catcatggca 420
aaaaatgagg ttttctgcgt tcaaccggaa aagggaggcc gcaagccagc tcgccttatc 480
gtgttcccag acctgggggt tcgtgtgtgc gagaaaatgg ccctctacga cgtggtytcy 540
acccttcctc aggccgtgat gggcccctca tacgggttcc agtactctcc tggacagcgg 600
gtcgagttcc tggtgaatgc ctggaaatca aagaaatgcc ctatgggctt cgcatatgac 660
acccgctgtt ttgactcaac ggtcactgag agtgatatcc gtactgagga gtctatttac 720
caatgttgtg acctggcccc cgaagctaga caagtcataa ggtcgctcac agagcggctt 780
tayatygggg gcccccctgac yaattcaaaa gggcagaact gcggttatcg ccggtgccgy 840
gcgagcggcg tgctgacgac tagctgcggt aataccctca catgttactt gaaggcctct 900
gcggcctgtc gagctgcaaa gctccgggac tgcacgatgc tcgtgtgcgg agacgacctc 960
gtcgttatct gtgaaagcgc ggggacccag gaggacgcgg ctagcctacg agtcttcacg 1020

```
gaggctatga ctaggtactc agcccccccc ggggacccgc cccaaccaga gtacgacttg   1080
gagttgataa catcatgctc ctccaacgtg tcggtcgcgc acgacgcatm tggcaagagg   1140
gtgtactacc tcacccgtga ccccaccacc cccctcgcgc gggctgcgtg ggagacagct   1200
agacacactc caattaactc ctggctaggc aacatcatca tgtatgcgcc cacyytatgg   1260
gcaaggatga ttctgatgac tcacttcttc tccatccttc trgcycagga acaacttgaa   1320
aaagccctag attgccarat ctayggggcc tgttactcca ttgaaccact tgacctacct   1380
cagatcattc agcgactcca tggtctyagc gcattttcac tccatagtta ctctccaggt   1440
gagatcaata gggtggcttc aagcctcagg aaacttgggg tgccrcccctt gcgagtctgg   1500
agacatcggg ccaggagygt ccgcgctaag ctactgtccc arggagggag ggcygccacg   1560
tgtggtaagt acctcttcaa ctgggcagta aggaccaagc tyaaactcac tccaatcccg   1620
gctgcgtccc agctggactt gtccagctgg ttcgtygctg gttacagcgg gggagacata   1680
tatcacagcc tgtctcgtgc ccgrccccgc tggttcatgt ggtgcctact cctactctct   1740
gtaggggtag gcatctayct gctccccaay cgatga                            1776
```

<210> SEQ ID NO 225
<211> LENGTH: 1776
<212> TYPE: DNA
<213> ORGANISM: Hepatitis C virus

<400> SEQUENCE: 225

```
tcgatgtcct acacatggac aggcgccctg atcacgccat gcgctgcgga ggaaagcaag     60
ctgcccatca acccgttgag caactctttg ctgcgtcacc ataayatggt atacgctaca    120
acatcccgca gcgcaagcct acggcagaag aaggtcactt ttgacagact gcaagtcctg    180
gacgaccact accgggacgt gcttaaggag atgaaggcga aggcgtccac agttaaggct    240
aagcttctat ctgtagaaga agcctgcaaa ctgacacccc cacactcggc cagatccaaa    300
tttggctatg ggcaaagga cgtccggagc ctatccagca aggccgtcaa ccacatcaac     360
tccgtgtgga aggacttgct ggaagacact gagacaccaa ttgacaccac catcatggca    420
aaaaatgagg ttttctgcgt ccaaccagag aaaggaggcc gcaagccagc ccgccttatc    480
gtgttcccag acttaggggt tcgcgtgtgc gagaagatgg ccctttatga cgtggtctcc    540
acccttcctc aggccgtgat gggctcctcg tacggattcc aatactctcc tggacagcgg    600
gtcgagttcc tggtgaatgc ctggaaatca aagaaatgcc ctatgggctt ctcatatgac    660
acccgctgtt ttgactcaac agtcaccgag aatgatatcc gtgttgagga gtcaatttac    720
caatgctgtg acttggcccc cgaagccaaa caggccataa ggtcgctcac agagcggctt    780
tayatcgggg gtcccctgac taattcaaaa gggcagaact gcggttatcg ccggtgccgc    840
gcgagcggcg tgctgacgac cagctgcggt aataccctca cctgttactt gaaggccacc    900
gcggcctgtc gagctgcaaa gctccaggac tgcacgatgc tcgtgtgcgg ggacgacctt    960
gtcgttatct gtgaaagcgc gggaacccaa gaggacgcgg cgaacctacg agtcttcacg   1020
gaggctatga ctaggtattc tgcccccccc ggggacccgc cccaaccaga atacgacttg   1080
garttgataa catcatgctc ctccaacgtg tcggtcgcgc acgatgcatc tggcaagcgg   1140
gtgtaytacc tcacccgcga ccccaccacc cccctygcac gggctgcgtg ggaracagct   1200
agacacactc cagttaactc ctggctaggc aacattatca tgtatgcgcc caccttatgg   1260
gcaaggatga tcctgatgac tcacttcttc tccatccttc tagctcagga acaacttgaa   1320
```

```
aaagccctgg attgycaaat ctacggggcc tgttactcca ttgagccact tgacctacct   1380

cagatcattc agcgactcca tggccttagc gcattttcac tccacagtta ctctccaggt   1440

gagatcaata gggtggcttc atgcctcagg aaacttgggg taccaccctt gcgagtctgg   1500

agacatcggg ccagaagtgt ccgcgctaag ctactgtccc agggagggag ggccgccact   1560

tgtggcaggt acctcttcaa ttgggcagta aggaccaagc ttaaactcac tccaatcccg   1620

gctgcgtccc agttggactt gtccggctgg ttcgttgctg ggtacagcgg gggagacata   1680

tatcacagcc tgtctcgtgc ccgaccccgc tggttcctgt ggtgcctact cctactttct   1740

gtaggggtag gcatctacct gctccccaac cgatga                             1776


<210> SEQ ID NO 226
<211> LENGTH: 1776
<212> TYPE: DNA
<213> ORGANISM: Hepatitis C virus

<400> SEQUENCE: 226

tcgatgtcct ayacatggac aggcgccctg atcacgccat gcgccgcgga rgaaagcaag     60

ctgcccatca atgcgttgag caactctttg ctgcgtcacc ataayatggt ctacgccaca    120

acatcccgca gcgcaagcca gcggcagaag aaggtcacct ttgacagact gcaggtcctg    180

gacgaccact accgggacgt gcttaaggag atgaaggcga aggcgtccac agttaaggct    240

agacttctat cygtagaaga agcctgcaag ctgacgcccc cacactcagc cagatccaaa    300

tttggctatg gggcgaagga cgtccggaac ctatctagca aggccgttaa ccacatccgc    360

tccgtgtgga aggacttgct ggaagacact gaaacaccaa tcgacgctac catcatggca    420

aaaaatgagg ttttctgcgt ccaaccagag aaaggaggtc gcaagccrgc tcgccttatc    480

gtgttcccag atttgggagt ccgtgtgtgc gagaaaatgg ccctttacga cgtggtctcc    540

acccttcctc aggccgtgat gggcccctca tacggattcc aatactctcc tggacagcgg    600

gtcgagttcc tggtgaatgc ctggaaatca aagaaaaacc ctatgggctt ctcatatgac    660

acccgctgyt ttgactctac ggtcacygag agygacatcc gtactgagga gtcaatttac    720

caatgttgtg acttggcccc cgaagccaga caggttataa ggtcgctcac agagcggctt    780

tatatcgggg gtcctytgac taattcaaaa gggcagaact gcggctatcg ccggtgtcgc    840

gcaagcggcg tgctgacgac cagctgcggc aataccctca catgttacct gaaggccact    900

gcagcctgtc gagctgcgaa gctccaggac tgcacaatgc ttgtgtgtgg ggacgacctt    960

gtcgtyatct gtgagagcgc ggggacccaa gaggacgcag cgagcctacg agtcttcacg   1020

gaggctatga ctaggtactc tgctccccc ggggacccgc cccggccgga atacgacttg   1080

garttaataa catcatgctc ctccaacgtg tcggtcgcgc acgacgcaca yggcaaaagg   1140

gtgtactacc tcacccgtga ccccaccacc ccccttgcgc gggcygcatg ggagacagct   1200

agacacactc cagtcaactc ctggctaggc aacatcatca tgtatgcgcc caccttgtgg   1260

gcaaggatga tyctgatgac ycatttcttc tccatccttc tagcccagga gcaacttgaa   1320

aaagccctag attgtcagat ctacggggcc tgttactcca ttgagccact tgacctacct   1380

cagatcattc agcgactcca tggtcttagc gcattttcac tccacagtta ctctccaggt   1440

gagatcaata gggtggcttc atgcctcagg aaacttgggg taccacccct gcgagtctgg   1500

agacatcggg ccagaagtgt ccgcgctaag ctgctgtccc gggggggag ggctgccact   1560

tgtggcaagt acctcttcaa ctgggcrgta aggaccaagc tcaaactcac tccaatcccg   1620

gctgcgttca agctggactt gtccggctgg ttcgttgctg gttacagcgg gggagacata   1680
```

tatcacagcc tgtctcgtgc ccgaccccgc tggttyrtgt ggtgcctact cctactttct 1740
gtaggggtag gcatctacct gctccccaac cgatga 1776

<210> SEQ ID NO 227
<211> LENGTH: 1776
<212> TYPE: DNA
<213> ORGANISM: Hepatitis C virus

<400> SEQUENCE: 227
tcgatgtcct acacatggac aggcgccttg atcacaccgt gcgctgcgga rgagagcaag 60
ctgcccatca aygcgctgag caactctttg ytgcgycacc ataacatgrt ctatgccaca 120
acatcccgca gcgcyagcca amggcagarg aaggtcactt ttgayagact gcargtcctg 180
gacgaccact accgggacgt gctyaaggag atgaaggcga aggcgtccac agtcaaggct 240
aaacttctat ccgtagarga agcctgyaag ctgacrcccc cacactcggc cagatcyaaa 300
tttggctatg ggcaaagga cgtccggaac ctatccagca aggccgttaa ccacatccac 360
tccgtgtgga aggacttgct ggaagacact gacacaccaa ttgacaccac catcatggca 420
aaaaatgagg ttttctgyat ccaaccagag aaaggaggcc gcaagccagc tcgccttatc 480
gtrtacccag acctgggggt ccgrgtgtgc gagaagatgg ctctttayga tgtggtctcc 540
acycttcctc aggccgtgat gggcccctcr tacggatttc agtactctcc tggacagcgg 600
gttgagttcc tggtgaawgc ctggaartca aagaaatgcc ctatgggctt cgcrtatgac 660
acccgctgct tygactcrac ggtcactgag aatgacatyc gtgttgagga gtcaatttac 720
caatgttgtg acttggcycc cgaagccaga caggycataa ggtcgctcac agagcggctt 780
tayatcgggg gtccyctaac caattcaaaa gggcaaaact gcggttatcg ccggtgtcgc 840
gcragcggcg tgctgacgac tagctgcggc aayaccctta catgttactt gaargcctct 900
gcrgcctgtc gagctgcgaa gctccaggac tgcacgatgc tcgtgtgcgg agacgacctc 960
gtcgttatct gtgagagcgc ggggacccac gaggatgcgg cgagcctacg agtcttyacg 1020
gaggctatga ctaggtactc cgcccccccy ggggacccgc ctcagccaga atacgactta 1080
gagctgataa catcatgctc ttccaaygtg tcrgtcgcgc acgatgcatc yggcaaaagg 1140
gtrtactacc tcacccgtga ccccaccacc cccottgcrc gggctgcgtg ggaracagct 1200
agacacactc cagtyaactc ctggctaggc aacatcatca tgtaygcgcc caccytatgg 1260
gcaaggatga tcctgatgac tcatttcttc tccatccttc tagctcagga gcaacttgaa 1320
aaagccctag attgtcagat ctayggggcc tgttactcca ttgaaccact tgacctacct 1380
caaatcattc arcgactcca tggtattagc gcgttttcac tccayagtta ctctccaggw 1440
gagatcaata gggtggcttc atgcctcagg aaacttgggg taccrcccct gcgagtctgg 1500
agacatcggg ccaggagtgt ccgcgctaag ytactgtccc aggggggggag ggctgccact 1560 tgtggcaart acctcttcaa ctgggcagta araaccaagc ttaatctcac tccaattccg 1620
gctgcgtcca agctggattt atccrgctgg ttcgttgccg gytacagcgg gggagacata 1680
tatcacagcg tgtctcmtgc ccgaccccgc tggttcatgt ggtgcctrct cctactktct 1740
gtaggrgtag gcatctacct gctycccaac cgatga 1776

<210> SEQ ID NO 228
<211> LENGTH: 1776
<212> TYPE: DNA
<213> ORGANISM: Hepatitis C virus -continued

```
<400> SEQUENCE: 228

tcgatgtcct acacatggac aggcgccctg atcacgccat gcgctgcgga ggaaaccaag      60

ctgcccatca atgcactgag caactctttg ctccgtcacc acaacttggt ctatgctaca     120

acatctcgca gcgcaagcct gcggcagaag aaggtcacct ttgacagact gcaggtcctg     180

gacgaccact accgggacgt gctcaaggag atgaaggcga aggcgtccac agttaaggct     240

aaacttctat ccgtggagga agcctgtaag ctgacgcccc cacattcggc cagatctaaa     300

tttggctatg gggcaaagga cgtccggaac ctatccagca aggccgttaa ccacatccgc     360

tccgtgtgga aggacttgct ggaagacact gagacaccaa ttgacaccac catcatggca     420

aaaaatgagg ttttctgcgt ccaaccagag aagggggcc gcaagccagc tcgccttatc      480

gtattcccag atttgggggt tcgtgtgtgc gagaaaatgg ccctttacga tgtggtctcc     540

accctccctc aggccgtgat gggctcttca tacggattcc aatactctcc tggacagcgg     600

gtcgagttcc tggtgaatgc ctggaaagcg aagaaatgcc ctatgggctt cgcatatgac     660

acccgctgtt ttgactcaac ggtcactgag aatgacatcc gtgttgagga gtcaatctac     720

caatgttgtg acttggcccc cgaagccaga caggccataa ggtcgctcac agagcggctt     780

tacatcgggg gccccctgac taattctaaa gggcagaact gcggctatcg ccggtgccgc     840

gcgagcggtg tactgacgac cagctgcggt aatacccctca catgttactt gaaggccgct     900

gcggcctgtc gagctgcgaa gctccaggac tgcacgatgc tcgtatgcgg agacgacctt     960

gtcgttatct gtgaaagcgc ggggacccaa gaggacgagg cgagcctacg ggccttcacg    1020

gaggctatga ctagatactc tgccccccct ggggacccgc ccaaaccaga atacgacttg    1080

gagttgataa catcatgctc ctccaatgtg tcagtcgcgc acgatgcatc tggcaaaagg    1140

gtgtactatc tcacccgtga ccccaccacc ccccttgcgc gggctgcgtg ggagacagct    1200

agacacactc cagtcaattc ctggctaggc aacatcatca tgtatgcgcc caccttgtgg    1260

gcaaggatga tcctgatgac tcatttcttc tccatccttc tagctcagga acaacttgaa    1320

aaagccctag attgtcagat ctacggggcc tgttactcca ttgagccact tgacctacct    1380

cagatcattc aacgactcca tggccttagc gcattttcac tccatagtta ctctccaggt    1440

gagatcaata gggtggcttc atgcctcagg aaacttgggg taccgccctt gcgagtctgg    1500

agacatcggg ccagaagtgt ccgcgctagg ctactgtccc aggggggag ggctgccact     1560

tgtggcaagt acctcttcaa ctgggcagta aggaccaagc tcaaactcac tccaatcccg    1620

gctgcgtccc agttggattt atccagctgg ttcgttgctg gttacagcgg gggagacata    1680

tatcacagcc tgtctcgtgc ccgaccccgc tggttcatgt ggtgcctact cctactttct    1740

gtaggggtag gcatctatct actccccaac cgatga                              1776
```

METHOD FOR DETERMINING DRUG RESISTANCE MUTATIONS IN ANY OF THE NON-STRUCTURAL PROTEIN REGIONS NS3 TO NS5B OF HEPATITIS C VIRUS (HCV) FOR GENOTYPES 1 TO 6

SEQUENCE LISTING

The instant application contains a Sequence Listing which has been submitted electronically in ASCII format and is hereby incorporated by reference in its entirety. Said ASCII copy, created on Jul. 18, 2014, is named VIP0030USPCT_SL.txt and is 169,634 bytes in size.

This application is the national stage of PCT Application No. PCT/EP2009/062986 filed Oct. 6, 2009, which claims priority from European Patent Application No. 08165949.2, filed Oct. 6, 2008, the entire disclosures of which are hereby incorporated in their entirety.

The present invention relates to a method for determining drug resistance mutations in any of the non-structural protein regions NS3 to NS5B of Hepatitis C Virus (HCV) for genotypes 1 to 6, more in particular for subtype specific genotypes 1a, 1b, 2a, 2b, 3a, 4a and 4d.

HCV is a single stranded, positive-sense RNA virus, with a genome of around 9,600 bases belonging to the Flaviviridae family of viruses in the hepacivirus genus. The NS5B region of the RNA polygene encodes a 65 kDa RNA dependent RNA polymerase (RdRp), which is essential to viral replication. Following the initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis, leading to cirrhosis, end-stage liver disease, and HCC (hepatocellular carcinoma), making it the leading cause of liver transplantations.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

There are six major HCV genotypes and more than 50 subtypes, which are differently distributed geographically. HCV genotype 1 is the predominant genotype in Europe and the USA. The extensive genetic heterogeneity of HCV has important diagnostic and clinical implications, perhaps explaining difficulties in vaccine development and the lack of response to current therapy.

The genetic variability of HCV complicates amplification, sequencing and genotyping processes. These processes rely on the use of so-called primers complementary to and capable of hybridizing to corresponding nucleic acid sequences of the HCV genome. Due to the high degree of variability of the HCV genome, primers complementary to one HCV species may not be complementary to another species.

To determine the subtype of an HCV clinical isolate an accurate and direct method is sequencing the viral genome in a region that is sufficiently divergent among various species in order to distinguish between HCV genotypes and subtypes accordingly. Phylogenetic analysis of the sequences generated from these regions is used to determine the subtype of clinical isolates.

Several selective and potent antiviral drugs against chronic hepatitis C virus (HCV) infection are currently evaluated in clinical trials. The emergence of drug resistance mutations was proven in previous trials, creating a need for patients to be monitored for the development of such drug-resistance mutations.

In order to improve the identification of HCV types and subtypes for purposes of clinical analysis and therapeutic decision making by a treating physician, there is a continuing need to improve sequencing-based HCV assays.

The hepatitis C virus is, as mentioned above, currently classified into at least 6 major genotypes (FIG. 1). Each genotype differs from the other by 30% to 35% on nucleotide level and may be further divided into several subtypes with sequence diversity typically between 20% and 25% (Simmonds et al., Hepatology 2005; 42(4), 962-973).

The present invention relates to the development of subtype-specific assays for HCV genotype resistance analysis suitable for clinical trial support and regulatory filings.

In more detail the invention relates to genotyping assays covering the complete coding region from NS3 to NS5B as developed on a large panel of clinical samples including protocols for subtypes 1a, 1b, 2a, 2b, 3a, 4a and 4d.

The current invention relates to a NS5B sequence-based subtyping assay detecting all six HCV genotypes and discriminating between the different subtypes.

One aspect of the invention concerns a method for determining drug resistance mutations in any of the non-structural protein regions NS3 to NS5B of Hepatitis C Virus (HCV) for genotypes 1 to 6, more in particular for subtype specific genotypes 1a, 1b, 2a, 2b, 3a, 4a and 4d, present in a sample comprising:

a) obtaining said sample from a patient, b) extracting viral genetic material from said sample, c) amplification of the NS5B region of HCV to generate a DNA amplicon of 388 base pairs by using primers having the sequences selected from the group consisting of SEQ ID NO's 1-5, d) sequencing of the amplicon to obtain a sequence of 329 base pairs by using the sequences selected from the group consisting of SEQ ID NO's 3-5, e) performing phylogenetic tree analysis using the 329 base pair sequence information of NS5B to obtain HCV-subtype information in said patient sample, f 1) using subtype-specific primers having the sequences selected from either the group consisting of SEQ ID NO's 6-9, 42-45, 104-107, 120-123, 145-148 or 180-183 for the generation of a DNA amplicon comprising the non-structural protein NS3 (N-terminal 181 amino acids), g 1) sequencing the NS3 amplicon to obtain a sequence of 543 base pairs by using the sequences selected from the group consisting of SEQ ID NO's 8 and 9; 43 and 45-46; 104 and 106; 120 and 122; 146 and 148 or 180 and 182 or f 2) using subtype-specific primers having the sequences selected from the group consisting of SEQ ID NO's 13-16, 54 and 59-66, 124-133, 158 and 160-168 or 194-197 for the generation of a DNA amplicon comprising NS5B polymerase, g 2) sequencing the NS5B polymerase amplicon to obtain a sequence of 1776 base pairs by using the sequences selected from the group consisting of SEQ ID NO's 15-16 and 87-92; 54, 59 and 61-66; 124 and 127-133; 158-159, 161 and 163-168 or 197-204 or f 3) using subtype-specific primers having the sequences selected from the group consisting of SEQ ID NO's 30-33, 67-70, 93-96, 108-111, 134-137 or 169-172 for the generation of a DNA amplicon comprising NS3/4A, g 3) sequencing the NS3/4A protease amplicon to obtain a sequence of 2055 base pairs by using the sequences selected from the group consisting of SEQ ID NO's 34-41; 68 and 71-77; 95 and 97-103; 112-119; 136 and 138-144 or 171 and 173-179 or f 4) using subtype-specific primers having the sequences selected from the group consisting of SEQ ID NO's 47-50, 78-81, 149-151 and 159 or 184-187 for the generation of a DNA amplicon comprising NS4B/5A, g 4) sequencing the NS4B/5A amplicon to obtain a sequence of the two genes NS4B and NS5A by using the sequences selected from the group consisting of SEQ ID NO's 51-57; 79 and 81-87; 152-159 or 185 and 187-193;

h) aligning the sequence obtained in step (g 1), (g 2), (g 3) or (g 4) with a reference or wild-type HCV sequence, i) determining drug resistance mutation(s) in the viral genetic material present in patient sample.

Another embodiment of the current invention is that above method further comprises the steps for performing a NS3 phenotyping assay by j) generating a NS3 amplicon starting from the DNA amplicon comprising the NS3 (N-terminal 181 amino acids) as obtained in step (f 1) of claim 1 using primers having the sequence of SEQ ID NO 11 and 12, k) inserting, by InFusion™ cloning or in vitro recombination, said amplicon obtained in step (j) into a NS3 deleted replication incompetent marker containing shuttle vector having the sequence of SEQ ID NO 10 to obtain a NS3 replication competent recombinant HCV replicon, l) generating RNA, by in vitro transcription, from said HCV replicon obtained in step (k)

m) transfecting said RNA into suitable cells, n) determining, based on the expression of the marker gene, the $EC_{50}$ value and/or fold change as a measure for the presence of drug resistance mutations in a sample.

In another embodiment the invention relates to the above mentioned method further comprising the steps for performing a NS5B phenotyping assay by o) generating a NS5B amplicon starting from the DNA amplicon comprising the NS5B as obtained in step (f 2) of claim 1 using primers having the sequence of SEQ ID NO 28 and 29, p) inserting, by in vitro recombination, said amplicon obtained in step (o) into a NS5B deleted replication incompetent marker containing shuttle vector having the sequence of SEQ ID NO 21 or SEQ ID NO 27 to obtain a NS5B replication competent recombinant HCV replicon, q) generating RNA, by in vitro transcription, from said HCV replicon obtained in step (p)

r) transfecting said RNA into suitable cells, s) determining, based on the expression of the marker gene, the $EC_{50}$ value and/or fold change as a measure for the presence of drug resistance mutations in a sample.

Part of the invention is also a vector comprising the HCV genome and a deletion spanning the HCV NS3 N-terminal 181 amino acid region, in particular vector pFK I341 PI luc ΔNS3 7-192_ET (SEQ ID NO. 10) and a vector comprising the HCV genome and a deletion spanning the HCV NS5B region, in particular vector pFK_I1341_PI_NS3-3_ET_dNS5a/b__5a440-5b591-Scla (SEQ ID NO 21) and the vector comprising the HCV genome and a deletion spanning the HCV NS5B region, in particular vector pFK_I341_PI_NS3-3_ET_dNS5a/b__5a440-5b591-XbaI (SEQ ID NO 27).

Besides the use of any of the above vectors in any of the methods mentioned, also the primers with SEQ ID NO 1-5 for the amplification of the HCV NS5B region, as obtained from a sample of an HCV-infected patient, belong to the invention.

The use of the primers with SEQ ID NO 1-5 for the preparation of a sequence-based subtyping HCV assay to detect HCV genotypes 1, 2, 3 and 4 and to discriminate between the subtypes 1a, 1b, 2a, 2b, 3a, 4a and 4d, belongs in particular to the current invention.

EXPLANATION OF FIGURES

FIG. 2: Overview of amplicons for the integrated HCV platform.

FIG. 3: Development status of the HCV subtyping and subtype-specific genotyping assays and their performance characteristics. Numbers in brackets show the number of tested samples.

FIG. 5: process overview

Figure 1:
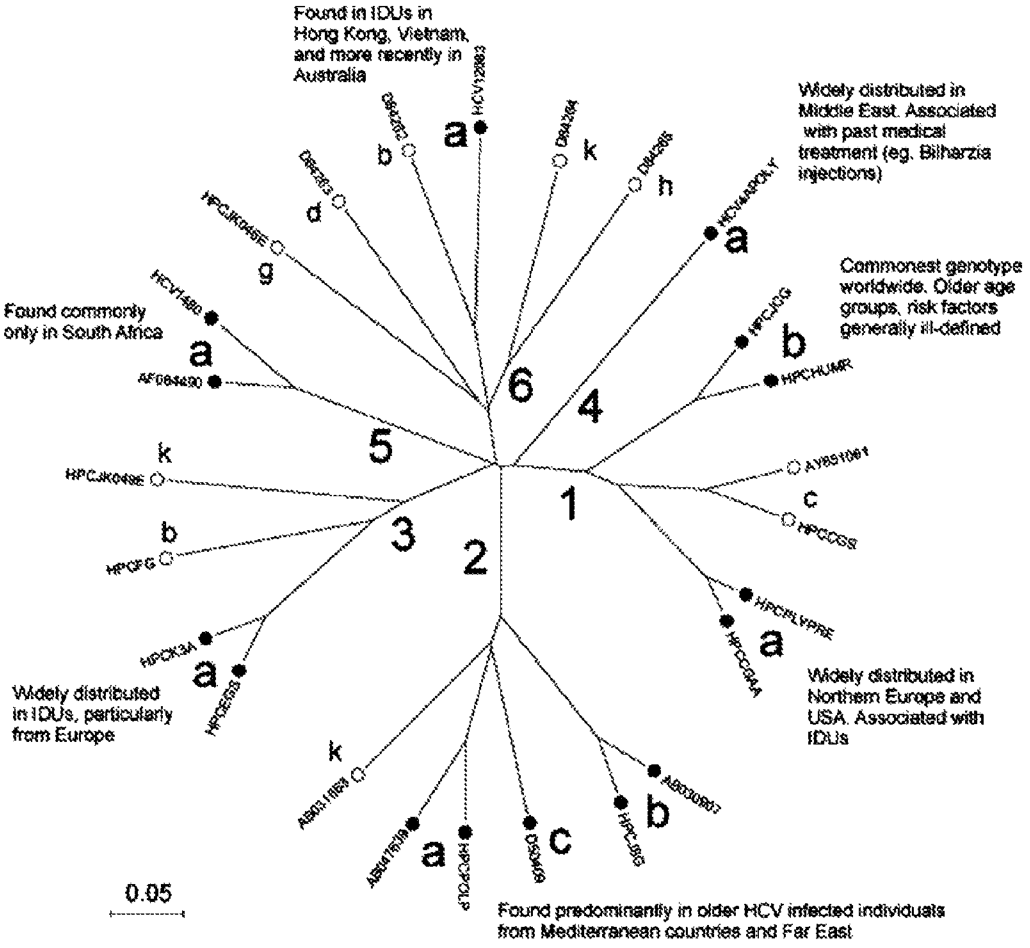
FIG. 1: Phylogenetic tree of complete open-reading frame sequences of HCV showing the major 6 genotypes and their most common subtypes. (Simmonds et al. 2005 Hepatology 2005; 42(4), 962-973)
Figure 4:
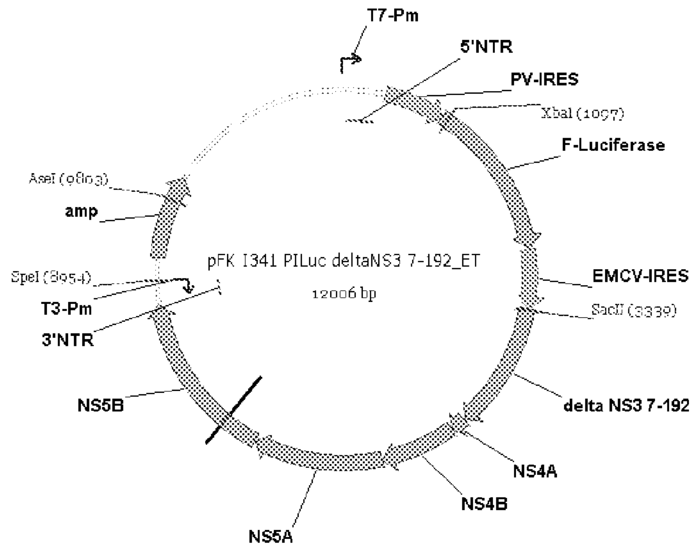
FIG. 4: Vector pFK I341 PI luc ΔNS3 7-192_ET (SEQ ID NO. 10)

A panel of 603 clinical samples covering all six genotypes (G) was collected. Two test systems were developed: a NS5B sequence-based subtyping assay and a set of subtype-specific genotyping assays to determine drug-resistance mutations in the following target regions: (1) protease inhibitors (complete NS3/4A and the N-terminal 181 as of NS3), (2) polymerase inhibitors (complete NS5B), and (3) others (complete NS4B/5A region). All primer sets have been optimized for subtype specificity and to allow the same PCR protocol to be used for a target region independent of the subtype (FIG. 2). All methods and protocols were optimized and validated to support high-throughput processing of the genotypic resistance assays in a routine operational setting.

The NS5B sequence-based subtyping assay was tested on a set of 603 clinical samples containing all six genotypes with a clinical sensitivity (amplification success rate of high viral load samples) of 91%.

For the subtype-specific genotyping assays, sets of clinical samples of, on average, n=94 for G1a/b, n=16 for G2a/b, n=76 for G3a, and n=83 for G4a/d were tested in the different assays to evaluate the clinical sensitivity. Amplification success rates between 90% and 100% and sequencing success rates between 95% and 100% were achieved (FIG. 3).

EXAMPLE SECTION

General Outline

The general process flow is visualized in FIG. 5. It starts with the determination of the HCV subtype of a clinical sample (Subtyping). This subtype information is then used in the subsequent Genotyping process to select the appropriate subtype-specific primers for amplification and sequencing of the target region of interest. The end result of the Genotyping process is the nucleotide and amino acid sequence information of that region. By comparison to a wildtype or viral reference sequence it provides information about the occurrence of amino acid changes. PCR products from the Genotyping process will be used in the Phenotyping process to generate chimeric subgenomic replicons for drug susceptibility assessment. The results of the phenotyping are $EC_{50}$ values which can be used for interpretation of drug susceptibility (i.e. by calculating $EC_{50}$ fold change values) of the clinical isolate. Sequence information of the target region and drug susceptibility can be compared.

1. Subtyping

An amplicon was generated from patient-derived viral plasma RNA by One-step RT-PCR followed by nested PCR. This amplicon, further referred to as the NS5B subtyping amplicon, contains a 329 bp sequence of the NS5B polymerase domain, which is used for phylogenetic tree analysis in order to obtain subtype information of the clinical isolate. The assay is called the NS5B sequence-based subtyping assay. The subtype information of the clinical isolate will be used in a next step to select the appropriate subtype-specific amplification and sequencing primers in order to obtain sequence information of the region of interest in the genotyping assay.

2. Genotyping

Using subtype-specific primers, an amplicon of the NS3 protease domain (containing the catalytic domain) is generated from patient-derived viral plasma RNA by One-Step RT-PCR followed by nested PCR. This amplicon, further referred to as the NS3 amplicon, contains the catalytic domain of the NS3 protease. This amplicon is going to be sequenced with subtype-specific sequencing primers in the HCV NS3 protease genotypic assay.

Using subtype-specific primers, an amplicon of the complete NS5B polymerase can also be generated from patient-derived viral plasma RNA by One-Step RT-PCR followed by nested PCR. This amplicon, further referred to as the NS5B amplicon, contains the complete NS5B gene. This amplicon is going to be sequenced with subtype-specific sequencing primers in the HCV NS5B polymerase genotypic assay.

The same can be achieved using subtype-specific primers for other dedicated HCV regions like NS3/NS4A or NS4B/NS5A and the like.

3. Phenotyping

A NS3-deleted replication incompetent shuttle vector, further referred to as the delta[NS3] backbone, has been generated based on the subgenomic replicon con1b sequence. The NS3 amplicon is generated, from patient-derived material, replicon plasmid DNA, synthetic genes or PCR products of replicon RNA, by PCR using the One-Step RT-PCR product of the HCV NS3 protease genotypic assay. In-Fusion™ cloning (Clontech) of the PCR-generated NS3 amplicon and the delta[NS3] backbone resulted in a replication-competent recombinant HCV replicon that was used in experiments to evaluate HCV NS3 phenotypic drug resistance.

A NS5B-deleted replication incompetent shuttle vector, further referred to as the delta[NS5B] backbone has been generated based on the subgenomic replicon con1b sequence. The NS5B amplicon is generated, from patient-derived material, replicon plasmid DNA, synthetic genes or PCR products of replicon RNA, by PCR using the One-Step RT-PCR product of the HCV NS5B polymerase genotypic assay. In vitro cloning (using BD In-Fusion™, Clontech Laboratories Inc.) of the PCR-generated NS5B amplicon and the delta[NS5B] backbone resulted in a replication-competent recombinant HCV replicon that was used in experiments to evaluate HCV NS5B phenotypic drug resistance.

EXAMPLE 1

NS5B Sequence-Based Subtyping Assay

A. RNA-Extraction

From a total 500 μl of plasma, total RNA was extracted using the EasyMAG™ RNA extraction platform (BioMerieux). After elution in 60 μl elution buffer, RNA was stored at −80° C. until use for amplicon generation.

B. One-Step RT-PCR

Five μl RNA were mixed with 2× reaction buffer, 120 ng/ml yeast tRNA (Ambion Inc., Woodward, USA), 0.2 μM primer NS5Bsubtype_A (TGGGGTTCGCGTATGATACCCGCTGCTTTGA) (SEQ ID NO: 1), 0.2 μM primer NS5Bsubtype_B (TGGGGTTTTCTTACGACACCAGGTGCTTTGA) (SEQ ID No: 2), 0.2 μM primer Pr2 (published in Sandres-Saunes et al. 2003) and 0.5 μl of the Superscript™ III RT/Platinum Taq High Fidelity enzyme mix from the SuperScript™ III One-Step RT-PCR System (Invitrogen) in a total volume of 25 μl. The cDNA synthesis is performed for 30 min at 52° C. followed by a denaturation step at 94° C. for 2 min. Thermal cycling consisted of 50 cycles of denaturation at 94° C. for 15 s, annealing at 63° C. for 30 s and elongation at 72° C. for 30 s. Final extension took place at 72° C. for 5 min. An aliquot of the resulting amplification product was used for a nested PCR step.

C. Inner PCR

For the nested PCR, 2.5 μl from the One-Step RT-PCR product were mixed with 10× buffer 2 from the Expand™ High Fidelity kit (Roche), 0.35 mM dNTPs (Promega), 0.4 μM primer NS5Bsubtype_C (CCGTATGATACCCGCTGCTTTGACTCAAC) (SEQ ID NO: 3), 0.3 μM primer NS5Bsubtype_D (TCCTACGACACCAGGTGCTTTGATTCAAC) (SEQ ID NO: 4), 0.4 μM primer NS5Bsubtype_E (AATTCCTGGTCATAGCCTCCGTGAAGACTC) (SEQ ID NO: 5) and 0.075 U/μl of DNA polymerase (Roche, Basel, Switzerland) to give a total volume of 50 μl. Initial denaturation was 94° C. for 2 min and thermal cycling consisted of 30 cycles of denaturation at 94° C. for 15 s, annealing at 56° C. for 30 s and elongation at 72° C. for 30 s. Final extension took place at 72° C. for 5 min. The amplicons were purified using the QIAQuick 96 PCR purification kit (Qiagen,). Final volume of purified amplicons was 100 μl.

D. Raw Sequence Analysis

Sequencing reaction was performed according to standard procedures by using the primers from the nested PCR for sequencing of both directions, forward and reverse. Electropherograms were retrieved from the ABI3730 capillary sequencer and imported into Seqscape v2.5 (Applied Biosystems). Sequence ends were trimmed based on quality values and the 329 bp length of the subtyping reference sequence; the latter spanned the regions between the amplification primers. No insertions, deletions or STOP codons were allowed to occur in the sequences.

E. Phylogenetic Tree Analysis

The sample sequences with a length of 329 bp were merged with subtype reference sequences in BioEdit ((Ibis Therapeutics; public source internet: www.mbio.ncsu.edu/BioEdit/bioedit.html) and subsequently analysed in MEGA v3.1 (public source, internet: http://www.megasoftware.net/) using Neighbour-Joining tree and Jukes-Cantor distance model.

Results:

>Pt 1 NS5B subtyping (SEQ ID NO: 205)

AGTCACCGAGAATGATATCCGTGTTGAGGAGTCAATTTACCAATGCTGTG
ACTTGGCCCCCGAAGCCAAACAGGCCATAAGGTCGCTCACAGAGCGGCTT
TAYATCGGGGGTCCCCTGACTAATTCAAAAGGGCAGAACTGCGGTTATCG
CCGGTGCCGCGCGAGCGGCGTGCTGACGACCAGCTGCGGTAATACCCTC
ACCTGTTACTTGAAGGCCACCGCGGCCTGTCGAGCTGCAAAGCTCCAGG
ACTGCACGATGCTCGTGTGCGGGGACGACCTTGTCGTTATCTGTGAAAGC
GCGGGAACCCAAGAGGACGCGGCGAACCTAC

>Pt 2 NS5B subtyping (SEQ ID NO: 206)

TGTCACYGAGAGTGACATCCGYGTTGAGGAGTCAATCTACCAATGTTGTG
ACTTGGCCCCCGAAGCCAGACAGGCCATAAAGTCGCTCACAGAGCGGCT
TTAYATCGGGGGTCCCCTGACTAAYTCAAAAGGRCAGAACTGCGGYTATC
GCCGGTGCCGCGCGAGCGGCGTGCTGACGACTAGCTGCGGYAACACCC
TCACMTGTTACYTGAAGGCCTCTGCAGCCTGTCGAGCTGCRAAGCTCCAG
GACTGCACGATGCTCGTGTGCGGGGACGACCTTGTCGTTATCTGCGAGA
GTGCTGGGACCCAGGAGGACGYGGCGAGCCTAC

>Pt 3 NS5B subtyping (SEQ ID NO: 207)

GGTCACTGAGAATGACATTCGTGTCGAGGAGTCGATCTACCAATGCTGTG
ACTTGGCCCCCGAAGCCAGACARGCCATAAGGTCGCTCACGGAGCGGCT
TTATATCGGGGGTCCCCTGACTAATTCAAAAGGGCAGAACTGCGGTTATC
GCCGGTGCCGCGCGAGCGGTGTACTGACGACCAGCTGTGGTAATACCCT
CACATGTTACTTGAAGGCCTCTGCGGCCTGTCGAGCTGCCAAGCTCCAGG
ACTGCACGATGCTCGTGAACGGAGACGACCTTGTCGTTATCTGTGAGAGC
GCGGGAACCCAARAGGACGCAGCGAACCTAC

>Pt 4 NS5B subtyping (SEQ ID NO: 208)

RGTCACCGAGAGKGACATCCGTGTTGAGGAGTCRATYTACCAATGTTGTG
ACTTGGCCCCCGAAGCCAGACAGGCCATAAAGTCGCTCACRGAGCGGCT
CTATATCGGGGGCCCCCTGACTAATTCAAAAGGGCAGAACTGCGGTTATC
GCCGGTGCCGCGCCAGCGGCGTRCTGACGACCAGCTGCGGTAATACCCT
CACATGTTACTTGAAGGCCTCTGCGGCCTGTCGAGCTGCAAAGCTCCAGG
ACTGCACGATGCTTGTGTGYGGAGACGACCTYGTCGTTATCTGTGAGAGC
GCGGGGACCCAGGAGGACGCGGCGAGCCTAC

>Pt 5 NS5B subtyping (SEQ ID NO: 209)

GGTCACTGAGAGTGAYATCCGTGTYGAGGAGTCAATATACCAATGTTGTG
ACTTGGCCCCCGAAGCCAGACAGGCCATAAAGTCGCTCACAGAGCGGCT
CTATGTTGGGGGTCCCCTGACTAAYTCAAAAGGGCAGAACTGCGGTTATC
GCCGGTGCCGCGCCAGCGGCGTGCTGACGACCAGCTGCGGTAATACCCT
CACTTGTTACTTGAAAGCCTCTGCRGCCTGTCGAGCTGCGAAGCTCCAGG

-continued

ACTGCACGATGCTCGTGTGTGGAGACGACCTTGTCGTTATCTGCGAAAGC
GCGGGAACCCAGGAGGACGCGGCGAGCCTAC

>Pt 12 NS5B subtyping (SEQ ID NO: 210)

AGTCACTGAGAGTGACATCCGCGTTGAGGAGTCAATCTACCAATGTTGTG
ACTTGGCCCCCGAAGCCAAACAGGCCATAAAGTCGCTCACAGAGCGGCT
TTACATCGGGGGTCCCCTGACTAATTCAAAAGGGCAGAACTGCGGCTATC
GCCGGTGCCGCGCCAGCGGCGTACTGACGACCAGCTGTGGTAATACCCT
CACATGTTACTTGAAAGCCTCTGCGGCCTGTCGAGCTGCAAAGCTCCAGG
ACTGCACGATGCTCGTGTGCGGAGACGACCTTGTCGTTATCTGTGAGAGC
GCGGGAACCCAGGAGGACGCGGCGAGCCTAC

>Pt 13 NS5B subtyping (SEQ ID NO: 211)

GGTCACTGAGAGTGATATCCGTACTGAGGAGTCTATTTACCAATGTTGTG
ACCTGGCCCCCGAAGCTAGACAAGTCATAAGGTCGCTCACAGAGCGGCTT
TAYATYGGGGGCCCCCTGACYAATTCAAAAGGGCAGAACTGCGGTTATCG
CCGGTGCCGYGCGAGCGGCGTGCTGACGACTAGCTGCGGTAATACCCTCA
CATGTTACTTGAAGGCCTCTGCGGCCTGTCGAGCTGCAAAGCTCCGGGA
CTGCACGATGCTCGTGTGCGGAGACGACCTCGTCGTTATCTGTGAAAGCG
CGGGGACCCAGGAGGACGCGGCTAGCCTAC

>Pt 14 NS5B subtyping (SEQ ID NO: 212)

AGTCACCGAGAATGATATCCGTGTTGAGGAGTCAATTTACCAATGCTGTG
ACTTGGCCCCCGAAGCCAAACAGGCCATAAGGTCGCTCACAGAGCGGCTT
TAYATCGGGGGTCCCCTGACTAATTCAAAAGGGCAGAACTGCGGTTATCG
CCGGTGCCGCGCGAGCGGCGTGCTGACGACCAGCTGCGGTAATACCCTC
ACCTGTTACTTGAAGGCCACCGCGGCCTGTCGAGCTGCAAAGCTCCAGG
ACTGCACGATGCTCGTGTGCGGGGACGACCTTGTCGTTATCTGTGAAAGC
GCGGGAACCCAAGAGGACGCGGCGAACCTAC

>Pt 15 NS5B subtyping (SEQ ID NO: 213)

GGTCACYGAGAGYGACATCCGTACTGAGGAGTCAATTTACCAATGTTGTG
ACTTGGCCCCCGAAGCCAGACAGGTTATAAGGTCGCTCACAGAGCGGCT
TTATATCGGGGGTCCTYTGACTAATTCAAAAGGGCAGAACTGCGGCTATC
GCCGGTGTCGCGCAAGCGGCGTGCTGACGACCAGCTGCGGCAATACCCT
CACATGTTACCTGAAGGCCACTGCAGCCTGTCGAGCTGCGAAGCTCCAG
GACTGCACAATGCTTGTGTGTGGGGACGACCTTGTCGTYATCTGTGAGAG
CGCGGGGACCCAAGAGGACGCAGCGAGCCTAC

>Pt 16 NS5B subtyping (SEQ ID NO: 214)

GGTCACTGAGAATGACATYCGTGTTGAGGAGTCAATTTACCAATGTTGTG
ACTTGGCYCCCGAAGCCAGACAGGYCATAAGGTCGCTCACAGAGCGGCTT
TAYATCGGGGGTCCYCTAACCAATTCAAAAGGGCAAAACTGCGGTTATCG
CCGGTGTCGCGCRAGCGGCGTGCTGACGACTAGCTGCGGCAAYACCCTT
ACATGTTACTTGAARGCCTCTGCRGCCTGTCGAGCTGCGAAGCTCCAGGA

-continued

CTGCACGATGCTCGTGTGCGGAGACGACCTCGTCGTTATCTGTGAGAGC

GCGGGGACCCACGAGGATGCGGCGAGCCTAC

These sequences were subtyped using phylogenetic analysis. Table 1 shows the result.

TABLE 1

| Sample ID | NS5B sequence based subtype information after phylogenetic analysis |
|---|---|
| Pt 1 | 1b |
| Pt 2 | 1b |
| Pt 3 | 1b |
| Pt 4 | 1b |
| Pt 5 | 1b |
| Pt 12 | 1b |
| Pt 13 | 1b |
| Pt 14 | 1b |
| Pt 15 | 1b |
| Pt 16 | 1b |

Based on the NS5B sequence-based subtype information, the appropriate subtype-specific primers were selected for the amplification of the NS3 protease domain.

EXAMPLE 2

HCV NS3 Genotyping Assay

A. One-Step RT-PCR

Five μl RNA were mixed with 2× reaction buffer, 120 ng/ml yeast tRNA (Ambion), 0.2 μM forward primer 1b-NS3_out_F (GCGTGTGGGGACATCATCTTAGG) (SEQ ID NO: 6), 0.2 μM primer 1b_NS3_out_R (GCTGCCAGTGGGAGCGTG) (SEQ ID NO: 7) and 0.5 μl of the Superscript™ III RT/Platinum Taq High Fidelity enzyme mix from the SuperScript™ III One-Step RT-PCR System (Invitrogen) in a total volume of 25 μl. The cDNA synthesis is performed for 30 min at 52° C. followed by a denaturation step at 94° C. for 2 min. Thermal cycling consisted of 50 cycles of denaturation at 94° C. for 15 s, annealing at 58° C. for 30 s and elongation at 72° C. for 1 min. Final extension took place at 72° C. for 5 min. An aliquot of the resulting amplification product was used for a nested PCR step.

B. Inner PCR

For the nested PCR, 2.5 μl from the One-Step RT-PCR product was mixed with 10× buffer 2 from the Expand™ High Fidelity kit (Roche), 0.35 mM dNTPs (Promega), 0.4 μM primer 1b_NS3_in_F (TCATCTTAGGCCTGCCCGTCTC) (SEQ ID NO: 8), 0.4 μM primer 1b_NS3_in_R (GGGAGCGTGTAGATGGGCCAC) (SEQ ID NO: 9) and 0.075 U/μl of Expand™ High Fidelity DNA polymerase (Roche) to give a total volume of 50 μl. Initial denaturation was 94° C. for 2 min and thermal cycling consisted of 30 cycles of denaturation at 94° C. for 15 s, annealing at 58° C. for 30 s and elongation at 72° C. for 1 min. Final extension took place at 72° C. for 5 min. The amplicons were purified using the QIAQuick 96 PCR purification kit (Qiagen). Final volume of purified amplicons was 100 μl.

C. Raw Sequence Analysis

Sequencing reaction was performed according to standard procedures by using the primers from the nested PCR for sequencing of both directions, forward and reverse (SEQ ID No's 8-9). Electropherograms were retrieved from the ABI3730 capillary sequencer and imported into Seqscape v2.5 (Applied Biosystems). Sequence ends were trimmed based on quality values and the 543 bp (coding sequence for the N-terminal 181 aa of NS3) length of the subtyping reference sequence; the latter spanned the regions between the amplification primers. No insertions, deletions or STOP codons were allowed to occur in the sequences.

Result:

NS3 Protease Sequences from Five (5) HCV-1b Patient Isolates

>Pt 1 NS3

(SEQ ID NO: 215)

GCGCCTATCACGGCCTACGCCCARCAAACACGGGGCTTGTTTGGCTGTAT

CATCACTAGCCTCACAGGCCGGGACAAGAACCAGGTCGAGGGGGAGGTC

CAAGTGGTTTCCACCGCCACACAATCTTTCCTGGCGACCTGTGTCAACGG

TGTKTGTTGGACTGTCTTCCACGGCGCCGGTTCAAAGACCCTGGCTGGCC

CAAAGGGYCCAATCACCCAAATGTACACCAATGTAGACCAGGACCTCGTC

GGCTGGCCGGCCCCCCCYGGGGCGCGCTCTCTRACACCATGCACCTGTG

GCAGCTCGGACCTTTACTTGGTCACGAGGCATGCTGATGTTATCCCGGTG

CGCCGGCGGGGCGACAGTAGGGGRAGCCTACTCTCCCCCAGGCCTGTG

TCCTACTTAAAAGGCTCTTCGGGTGGWCCRCTGCTCTGCCCCTCGGGGC

ACGCTGTGGGCGTCTTCCGGGCTGCTGTGTGCACCCGGGGGGTCGCGA

AGGCGGTGGACTTTGTACCCGTAGAGTCTATGGAGACTACCATGCGGTCC

>Pt 2 NS3

(SEQ ID NO: 216)

GCGCCCATCACGGCCTACGCCCAACARACGAGGGGCCTACTTGGCTGTA

TCATCACCAGCCTCACAGGCCGGGACAAGAACCAGGTYGAGGGGGAGGT

TCAGGTGGTCTCCACTGCAACACAGTCCTTCCTGGCRACTTGCATCAACG

GCGTGTGTTGGACTGTCTTTCATGGAGCCGGCTCTAAGACCCTAGCCGGC

CCAAAGGGGCCGATCACCCAGATGTACACCAATGTAGACCAGGACCTCGT

CGGCTGGCAAGCGCCCCCYGGGGCGCGTTCCTTGACACCGTGCACCTGC

GGCAGCTCGGACCTTTACTTGGTCACGAGGCATGCCGATGTCATTCCGGT

GCGCCGGCGAGGTGACAGCAGGGGGAGCTTGCTCTCCCCCCGGCCCAT

TTCYTACTTRAAAGGCTCTTCGGGTGGTCCRYTGCTCTGCCCCTCGGGGC

ACGCYGTGGGCATCTTCCGGGCTGCCGTGTGCACYCGGGGGGTTGCCAA

GGCRGTGGATTTTGTACCCGTTGAGTCTATGGAAACTACYATGCGGTCC

>Pt 3 NS3

(SEQ ID NO: 217)

GCGCCTATTACGGCCTACGCCCAACAGACGAGGGGCCTATTAGGCTGCA

TCATCACTAGCCTCACAGGCCGAGACAAGAACCAGGTCGAGGGGGAGGT

TCAGGTGGTTTCTACCGCAACACAATCCTTCCTAGCGACTTGCGTCAACG

GCGTGTGTTGGACTGTCTATCATGGCGCCGGCTCTAAGACCTTAGCCGGC

CCAAAGGGGCCTGTCACCCAAATGTACACCAATGTAGACCAAGACCTCGT

CGGCTGGCCAGCGCCCCCCGGGGCGCGTTCCTTGACACCATGTACTTGC

GGCAGTTCGGACCTTTACTTGGTCACGAGACATGCCGATGTCATTCCGGT

GCGCCGGCGGGGCGACAGCAGGGGGAGCCTGCTCTCCCCCAGGCCTGT

CTCCTATTTGAAGGGCTCTTCGGGTGGTCCACTGCTCTGCCCTTCAGGGC

-continued

ACGCCGTGGGCATCTTCCGGGCTGCCGTGTGCACCCGAGGGGTTGCCAA

GGCGGTGGACTTTGTGCCCGTCGAGTCCATGGAAACTACTATGCGGTCT

>Pt 4 NS3

(SEQ ID NO: 218)

GCGCCTATCACGGCTTACTCCCAACAGACGCGGGGCCTGCTTGGCTGCA

TCATCACYAGCCTCACAGGCAGRGACAAGAACCAGGTCGAGGGGGAAGT

CCAAGTGGTTTCCACCGCAACACAATCTTTTCTAGCGACCTGTGTCAACG

GCGTGTGTTGGACTGTTTTCCATGGCGCCGGCTCAAAAACCTTAGCCGGC

CCAAAGGGCCCGGTCACCCAAATGTACACCAATGTAGACCAGGACCTCGT

CGGCTGGCAGGCGCCTACCGGGGCGCGTTCTTTAACACCATGCACCTGC

GGCAGCTCGGACCTTTATTTGGTCACGAGGCATGCTGATGTCATTCCGGT

GCGCCGGCGGGGCGACAGCCGGGGGAGTCTACTCTCCCCCAGGCCCGT

CTCCTACTTGAAGGGCTCCTCGGGTGGTCCGCTGCTCTGCCCCTCGGGG

CATGCAGTGGGCATCTTCCGGGCTGCCGTGTGCACCCGGGGGGTCGCAA

AGGCAGTGGACTTCATACCCGTTGAGTCTATGGAAACTACTATGCGGTCC

-continued

>Pt 5 NS3

(SEQ ID NO: 219)

GCGCCTATCACAGCCTACTCCCAACAGACGCGGGGCCTGCTTGGCTGCA

TCATCACTAGCCTCACAGGCCGGGACAAGAACCAGGTCGAGGGGGAGGT

TCAAGTGGTTTCCACCGCGACACAATCTTTCCTGGCGACCTGCGTCAACG

GCGTGTGTTGGACTGTCTACCATGGTGCCGGCTCGAAGACCCTAGCCGG

CCCAAAGGGCCCGATCACCCAAATGTACACCAATGTAGACCAGGACCTCG

TCGGCTGGCCGGCGCCCTCCGGAGCGCGCTCCTTGACACCGTGCACCTG

CGGCAGCTCAGACCTYTACTTGGTCACGAGGCATGCTGATGTTGTTCCGG

TGCGCCGGCGGGGCGACAGCAGGGGAAGCCTACTCTCCCCCAGGCCCA

TTTCCTACTTGAAGGGCTCTTCGGGTGGCCCGCTGCTTTGCCCCTCGGGG

CACGCGGTGGGCATCTTCCGGGCTGCTGTATGCACCCGGGGGGTCGCGA

AGGCGGTGGACTTTGTACCCGTTGAGTCTATGGAAACCACCATGCGGTCT

D. Alignment of Sequences with Reference Sequence

The alignment shows the nucleotide sequence of the NS3 protease domain of an HCV-1b isolate from an untreated patient (SEQ ID NO: 219). The sequences were aligned against a reference sequence (SEQ ID NO: 220). Homologies between the two sequences are plotted as dots.

```
                            10        20        30        40
                    ....|....|....|....|....|....|....|....|
con1b reference     gcgcctattacggcctactcccaacagacgcgaggcctac
Pt 5                ........C..A....................G.....G.

                            50        60        70        80
                    ....|....|....|....|....|....|....|....|
con1b reference     ttggctgcatcatcactagcctcacaggccgggacaggaa
Pt 5                ....................................A...

                            90       100       110       120
                    ....|....|....|....|....|....|....|....|
con1b reference     ccaggtcgagggggaggtccaagtggtctccaccgcaaca
Pt 5                ..................T........T........G...

                           130       140       150       160
                    ....|....|....|....|....|....|....|....|
con1b reference     caatctttcctggcgacctgcgtcaatggcgtgtgttgga
Pt 5                ..........................C.............

                           170       180       190       200
                    ....|....|....|....|....|....|....|....|
con1b reference     ctgtctatcatggtgccggctcaaagacccttgccggccc
Pt 5                .......C..............G........A........

                           210       220       230       240
                    ....|....|....|....|....|....|....|....|
con1b reference     aaagggcccaatcacccaaatgtacaccaatgtggaccag
Pt 5                .........G........................A.....

                           250       260       270       280
                    ....|....|....|....|....|....|....|....|
con1b reference     gacctcgtcggctggcaagcgccccccggggcgcgttcct
Pt 5                ................CG......T....A.....C....

                           290       300       310       320
                    ....|....|....|....|....|....|....|....|
con1b reference     tgacaccatgcacctgcggcagctcggacctttacttggt
Pt 5                .......G.................A.....Y........

                           330       340       350       360
                    ....|....|....|....|....|....|....|....|
con1b reference     cacgaggcatgccgatgtcattccggtgcgccggcggggc
Pt 5                ............T.....TG....................

                           370       380       390       400
                    ....|....|....|....|....|....|....|....|
con1b reference     gacagcagggggagcctactctcccccaggcccgtctcct
Pt 5                ...........A.....................A.T....
```

-continued

```
                       410       420       430       440
                   ....|....|....|....|....|....|....|....|
con1b reference    acttgaagggctcttcgggcggtccactgctctgcccctc
Pt 5               ...................T..C..G.....T........
                       450       460       470       480
                   ....|....|....|....|....|....|....|....|
con1b reference    ggggcacgctgtgggcatctttcgggctgccgtgtgcacc
Pt 5               .........G...........C........T..A......
                       490       500       510       520
                   ....|....|....|....|....|....|....|....|
con1b reference    cgaggggttgcgaaggcggtggactttgtacccgtcgagt
Pt 5               ..G.....C..........................T....
                       530       540
                   ....|....|....|....|...
con1b reference    ctatggaaaccactatgcggtcc
Pt 5               .............C........T
```

The following shows the amino acid sequence of the NS3 protease domain of an HCV-1b isolate from an untreated patient (SEQ ID NO: 222). The sequences were aligned against a reference sequence (SEQ ID NO: 221). Homologies between the two sequences are plotted as dots.

0.35 mM dNTPs (Promega), 0.4 μM primer 1b_NS5B_in_F (TGGAAGGACCCGGACTACG) (Sequence ID NO:15), 0.4 μM primer 1b_NS5B_in_R (GAGTGGTTAGCTCCCCGTTCA) (Sequence ID NO:16) and 0.075 U/μl of Expand™ High Fidelity DNA polymerase (Roche,) to give a total volume of 50 μl. Initial denaturation was 94° C. for 2 min and thermal cycling consisted of 30 cycles of denaturation at 94° C. for 15 s, annealing at 59° C. for 30 s and elongation at 68° C. for 2 min 30 s. Final extension took place at 68° C. for 5 min. The amplicons were purified using the QIAQuick 96 PCR purification kit (Qiagen). Final volume of purified amplicons was 100 μl.

```
                        10        20        30        40
                   ....|....|....|....|....|....|....|....|
con1b reference    APITAYSQQTRGLLGCIITSLTGRDRNQVEGEVQVVSTAT
Pt 5               .........................K..............
                        50        60        70        80
                   ....|....|....|....|....|....|....|....|
con1b reference    QSFLATCVNGVCWTVYHGAGSKTLAGPKGPITQMYTNVDQ
Pt 5               ........................................
                        90       100       110       120
                   ....|....|....|....|....|....|....|....|
con1b reference    DLVGWQAPPGARSLTPCTCGSSDLYLVTRHADVIPVRRRG
Pt 5               .....P..S..............X.........V......
                       130       140       150       160
                   ....|....|....|....|....|....|....|....|
con1b reference    DSRGSLLSPRPVSYLKGSSGGPLLCPSGHAVGIFRAAVCT
Pt 5               ...........I............................
                       170       180
                   ....|....|....|....|.
con1b reference    RGVAKAVDFVPVESMETTMRS
Pt 5               .....................
```

NS3 amplicons from these five HCV-1b isolates were further used in the NS3 replicon phenotyping assay.

HCV NS5B Polymerase Genotyping Assay

One-Step RT-PCR:

Five μl RNA were mixed with 2× reaction buffer, 120 ng/ml yeast tRNA (Ambion Inc.), 0.2 μM primer 1b_NS5B_out_F (TAGAGTCCTGGAAGGACCCGG) (Sequence ID NO:13), 0.2 μM primer 1b_NS5B_out_R (GGCCTGGAGTGGTTAGCTCCCC) (Sequence ID NO:14) and 0.5 μl of the Superscript™ III RT/Platinum Taq High Fidelity enzyme mix from the SuperScript™ III One-Step RT-PCR System (Invitrogen) in a total volume of 25 μl. The cDNA synthesis is performed for 30 min at 47° C. followed by a denaturation step at 94° C. for 2 min. Thermal cycling consisted of 50 cycles of denaturation at 94° C. for 15 s, annealing at 59° C. for 30 s and elongation at 68-° C. for 2 min 30 s. Final extension took place at 68° C. for 5 min. An aliquot of the resulting amplification product was used for a nested PCR step.

Inner PCR:

For the nested PCR, 2.5 μl from the One-Step RT-PCR product was mixed with 10× buffer 1 from the Expand™ Long Template High Fidelity kit (Roche, Basel, Switzerland), Raw Sequence Analysis Sequencing reaction was performed according to standard procedures by using 8 sequencing primers (SEQ ID No's 15-16 and 87-92) to cover both directions, forward and reverse. Electropherograms were retrieved from the ABI3730 capillary sequencer and imported into Seqscape v2.5 (Applied Biosystems). Sequence ends were trimmed based on quality values and the 1776 bp (coding sequence of the NS5B polymerase) length of the subtype-specific reference sequence; the latter spanned the regions between the amplification primers. No insertions, deletions or STOP codons were allowed to occur in within the sequences.

Result:

NS5B Polymerase Sequences from Five HCV-1b Clinical Isolates

```
>Pt 12 NS5B
                                        (SEQ ID NO: 223)
TCGATGTCCTACACGTGGACGGGCGCCCTGATCACGCCGTGCGCCGCGG
AGGAAAGCAAGCTGCCTATCAATGCATTGAGCAACTCACTGCTGCGTCAC
CACAATATGGTTTATGCTACAACATCCCGCAGCGCAAGCCAGCGGCAGAA
GAAGGTCACTTTTGACAGACTGCAAGTCCTGGACGACCACTACCGGGACG
TGCTCAAGGAGATGAAGGCGAAGGCGTCCACAGTTAAGGCTAAGCTTCTA
TCTGTAGAGGAAGCCTGTAAACTGACGCCCCCACATTCGGCCAGATCCAA
ATTTGGCTAYGGGGCAAAGGACGTCCGGAACCTATCCAGCAAGGCCGTTA
ACCACATCCGCTCCGTGTGGAAGGACTTGCTGGAAGACACTGAGACACCA
ATTGACACCACCATCATGGCAAAAAACGAGGTYTTCTGCGTCCAACCAGA
GAAAGGAGGCCGCAAGCCAGCTCGCCTTATCGTGTTCCCAGACTTGGGA
GTTCGTGTGTGCGAGAAAATGGCCCTTTACGACGTGGTCTCCACTCTTCC
TCAAGCCGTGATGGGCTCCTCATATGGATTCCAGTACTCTCCTGGACAGC
GGGTTGAATTCCTGGTGAATGCCTGGAAGTCGAAGAAGAACCCTATGGGC
TTCGCATATGACACCCGCTGTTTTGACTCAACAGTCACTGAGAGTGACAT
CCGCGTTGAGGAGTCAATCTACCAATGTTGTGACTTGGCCCCCGAAGCCA
AACAGGCCATAAAGTCGCTCACAGAGCGGCTTTACATCGGGGGTCCCCTG
ACTAATTCAAAAGGGCAGAACTGCGGCTATCGCCGGTGCCGCGCCAGCG
GCGTACTGACGACCAGCTGTGGTAATACCCTCACATGTTACTTGAAAGCC
TCTGCGGCCTGTCGAGCTGCAAAGCTCCAGGACTGCACGATGCTCGTGT
GCGGAGACGACCTTGTCGTTATCTGTGAGAGCGCGGGAACCCAGGAGGA
CGCGGCGAGCCTACGAGTCTTCACGGAGGCTATGACTAGGTACTCCGC
CCCCCCCGGGGACCCGCCCCAGCCAGAGTACGACTTGGAGTTGATAAC
ATCATGCTCCTCCAACGTGTCGGTCGCGCACGATGCATCCGGCAAACGGG
TGTATTACCTCACCCGTGACCCCACCACCCCCCTCGCGAGGGCTGCGTGG
GAAACAGCTAGACACACTCCAGTTAATTCTTGGCTAGGCAACATCATTAT
GTATGCGCCCACCCTGTGGGCAAGGATGATTTTGATGACTCACTTCTTCT
CCATCCTTCTAGCTCAAGAACAACTTGAAAAAGCCCTGGATTGTCAGATC
TACGGGGCCTGCTACTCCATTGAGCCACTTGACCTACCTCAGATCATTCA
RCGACTCCATGGTCTTAGCGCATTTTCACTCCACAGTTACTCTCCAGGTG
AGATCAATAGGGTGGCTTCATGCCTCAGGAAACTTGGGGTACCGCCCTTG
CGAGTCTGGAGACATCGGGCCAGAAGTGTCCGCGCTAAGCTACTGTCCCA
GGGGGGGAGGGCTGCCATTTGTGGCAAGTACCTCTTCAACTGGGCRGTAA
GGACCAAGCTCAAACTCACTCCAATCCCGGCAGCGTCCCAGTTGGACTTG
TCCGACTGGTTCGTTGCCGGCTACAGCGGGGGAGACATATATCACAGCCT
GTCTCGTGCCCGACCCCGCTGGTTCCTGTGGTGCCTACTCCTGCTTTCTG
CGGGGGTAGGCATCTACTTGCTCCCCAACCGATGA
```

-continued

```
>Pt 13 NS5B
                                        (SEQ ID NO: 224)
TCGATGTCCTACACATGGACAGGCGCTTTAATCACACCATGCGCTGCGGA
GGAAAGCAAGCTGCCCATCAACGCGCTGAGCAACTCCCTGCTGCGYCAC
CACAATATGGTGTATGCCACAACATCCCGCAGCGCAAGCCARCGGCAGAA
GAARGTCACTTTTGACAGACTGCAAGTCCTGGACGAYCATTACCGGGACG
TRCTCAAGGAGGTGAAGGCGAAGGCGTCCACAGTTAAGGCYAAACTTCTA
TCCGTAGAAGAGGCCTGCAAACTSACGCCCCCACACTCAGCCAAATCCAA
RTTTGGCTATGGGGCRAAGGACGTCCGGAACCTATCCAGCAAGGCCGTY
AACCACATCCACTCCGTGTGGAAGGACTTGCTGGAGGACACTGAAACACC
AATTGACACTACCATCATGGCAAAAAATGAGGTTTTCTGCGTTCAACCGG
AAAAGGGAGGCCGCAAGCCAGCTCGCCTTATCGTGTTCCCAGACCTGGGG
GTTCGTGTGTGCGAGAAAATGGCCCTCTACGACGTGGTYTCYACCCTTCC
TCAGGCCGTGATGGGCCCCTCATACGGGTTCCAGTACTCTCCTGGACAG
CGGGTCGAGTTCCTGGTGAATGCCTGGAAATCAAAGAAATGCCCTATGGG
CTTCGCATATGACACCCGCTGTTTTGACTCAACGGTCACTGAGAGTGATA
TCCGTACTGAGGAGTCTATTTACCAATGTTGTGACCTGGCCCCCGAAGCT
AGACAAGTCATAAGGTCGCTCACAGAGCGGCTTTAYATYGGGGGCCCCCT
GACYAATTCAAAAGGGCAGAACTGCGGTTATCGCCGGTGCCGYGCGAGC
GGCGTGCTGACGACTAGCTGCGGTAATACCCTCACATGTTACTTGAAGGC
CTCTGCGGCCTGTCGAGCTGCAAAGCTCCGGGACTGCACGATGCTCGTG
TGCGGAGACGACCTCGTCGTTATCTGTGAAAGCGCGGGGACCCAGGAGG
ACGCGGCTAGCCTACGAGTCTTCACGGAGGCTATGACTAGGTACTCAGCC
CCCCCCGGGGACCCGCCCCAACCAGAGTACGACTTGGAGTTGATAACAT
CATGCTCCTCCAACGTGTCGGTCGCGCACGACGCATMTGGCAAGAGGGT
GTACTACCTCACCCGTGACCCCACCACCCCCCTCGCGCGGGCTGCGTGG
GAGACAGCTAGACACACTCCAATTAACTCCTGGCTAGGCAACATCATCAT
GTATGCGCCCACYYTATGGGCAAGGATGATTCTGATGACTCACTTCTTCT
CCATCCTTCTRGCYCAGGAACAACTTGAAAAAGCCCTAGATTGCCARATC
TAYGGGGCCTGTTACTCCATTGAACCACTTGACCTACCTCAGATCATTCA
GCGACTCCATGGTCTYAGCGCATTTTCACTCCATAGTTACTCTCCAGGTG
AGATCAATAGGGTGGCTTCAAGCCTCAGGAAACTTGGGGTGCCRCCCTTG
CGAGTCTGGAGACATCGGGCCAGGAGYGTCCGCGCTAAGCTACTGTCCCA
RGGAGGGAGGGCYGCCACGTGTGGTAAGTACCTCTTCAACTGGGCAGTAA
GGACCAAGCTYAAACTCACTCCAATCCCGGCTGCGTCCCAGCTGGACTTG
TCCAGCTGGTTCGTYGCTGGTTACAGCGGGGGAGACATATATCACAGCCT
GTCTCGTGCCCGRCCCCGCTGGTTCATGTGGTGCCTACTCCTACTCTCTG
TAGGGGTAGGCATCTAYCTGCTCCCCAAYCGATGA

>Pt 14 NS5B
                                        (SEQ ID NO: 225)
TCGATGTCCTACACATGGACAGGCGCCCTGATCACGCCATGCGCTGCGG
AGGAAAGCAAGCTGCCCATCAACCCGTTGAGCAACTCTTTGCTGCGTCAC
```

-continued

CATAAYATGGTATACGCTACAACATCCCGCAGCGCAAGCCTACGGCAGAA

GAAGGTCACTTTTGACAGACTGCAAGTCCTGGACGACCACTACCGGGACG

TGCTTAAGGAGATGAAGGCGAAGGCGTCCACAGTTAAGGCTAAGCTTCTA

TCTGTAGAAGAAGCCTGCAAACTGACACCCCCACACTCGGCCAGATCCAA

ATTTGGCTATGGGGCAAAGGACGTCCGGAGCCTATCCAGCAAGGCCGTC

AACCACATCAACTCCGTGTGGAAGGACTTGCTGGAAGACACTGAGACACC

AATTGACACCACCATCATGGCAAAAAATGAGGTTTTCTGCGTCCAACCAG

AGAAAGGAGGCCGCAAGCCAGCCCGCCTTATCGTGTTCCCAGACTTAGGG

GTTCGCGTGTGCGAGAAGATGGCCCTTTATGACGTGGTCTCCACCCTTCC

TCAGGCCGTGATGGGCTCCTCGTACGGATTCCAATACTCTCCTGGACAGC

GGGTCGAGTTCCTGGTGAATGCCTGGAAATCAAAGAAATGCCCTATGGGC

TTCTCATATGACACCCGCTGTTTTGACTCAACAGTCACCGAGAATGATAT

CCGTGTTGAGGAGTCAATTTACCAATGCTGTGACTTGGCCCCCGAAGCCA

AACAGGCCATAAGGTCGCTCACAGAGCGGCTTTAYATCGGGGGTCCCCTG

ACTAATTCAAAAGGGCAGAACTGCGGTTATCGCCGGTGCCGCGCGAGCG

GCGTGCTGACGACCAGCTGCGGTAATACCCTCACCTGTTACTTGAAGGCC

ACCGCGGCCTGTCGAGCTGCAAAGCTCCAGGACTGCACGATGCTCGTGT

GCGGGGACGACCTTGTCGTTATCTGTGAAAGCGCGGGAACCCAAGAGGA

CGCGGCGAACCTACGAGTCTTCACGGAGGCTATGACTAGGTATTCTGCCC

CCCCCGGGGACCCGCCCCAACCAGAATACGACTTGGARTTGATAACATCA

TGCTCCTCCAACGTGTCGGTCGCGCACGATGCATCTGGCAAGCGGGTGTR

AAYTACCTCACCCGCGACCCCACCACCCCCCTYGCACGGGCTGCGTGGGA

CAGCTAGACACACTCCAGTTAACTCCTGGCTAGGCAACATTATCATGTAT

GCGCCCACCTTATGGGCAAGGATGATCCTGATGACTCACTTCTTCTCCAT

CCTTCTAGCTCAGGAACAACTTGAAAAAGCCCTGGATTGYCAAATCTACG

GGGCCTGTTACTCCATTGAGCCACTTGACCTACCTCAGATCATTCAGCGA

CTCCATGGCCTTAGCGCATTTTCACTCCACAGTTACTCTCCAGGTGAGAT

CAATAGGGTGGCTTCATGCCTCAGGAAACTTGGGGTACCACCCTTGCGAG

TCTGGAGACATCGGGCCAGAAGTGTCCGCGCTAAGCTACTGTCCCAGGGA

GGGAGGGCCGCCACTTGTGGCAGGTACCTCTTCAATTGGGCAGTAAGGA

CCAAGCTTAAACTCACTCCAATCCCGGCTGCGTCCCAGTTGGACTTGTCC

GGCTGGTTCGTTGCTGGGTACAGCGGGGGAGACATATATCACAGCCTGT

CTCGTGCCCGACCCCGCTGGTTCCTGTGGTGCCTACTCCTACTTTCTGTA

GGGGTAGGCATCTACCTGCTCCCCAACCGATGA

>Pt 15 NS5B (SEQ IS NO: 226)

TCGATGTCCTAYACATGGACAGGCGCCCTGATCACGCCATGCGCCGCGG

ARGAAAGCAAGCTGCCCATCAATGCGTTGAGCAACTCTTTGCTGCGTCAC

CATAAYATGGTCTACGCCACAACATCCCGCAGCGCAAGCCAGCGGCAGA

AGAAGGTCACCTTTGACAGACTGCAGGTCCTGGACGACCACTACCGGGA

CGTGCTTAAGGAGATGAAGGCGAAGGCGTCCACAGTTAAGGCTAGACTTC

TATCYGTAGAAGAAGCCTGCAAGCTGACGCCCCCACACTCAGCCAGATCC

-continued

AAATTTGGCTATGGGGCGAAGGACGTCCGGAACCTATCTAGCAAGGCCGT

TAACCACATCCGCTCCGTGTGGAAGGACTTGCTGGAAGACACTGAAACAC

CAATCGACGCTACCATCATGGCAAAAAATGAGGTTTTCTGCGTCCAACCA

GAGAAAGGAGGTCGCAAGCCRGCTCGCCTTATCGTGTTCCCAGATTTGG

GAGTCCGTGTGTGCGAGAAAATGGCCCTTTACGACGTGGTCTCCACCCTT

CCTCAGGCCGTGATGGGCCCCTCATACGGATTCCAATACTCTCCTGGACA

GCGGGTCGAGTTCCTGGTGAATGCCTGGAAATCAAAGAAAAACCCTATGG

GCTTCTCATATGACACCCGCTGYTTTGACTCTACGGTCACYGAGAGYGAC

ATCCGTACTGAGGAGTCAATTTACCAATGTTGTGACTTGGCCCCCGAAGC

CAGACAGGTTATAAGGTCGCTCACAGAGCGGCTTTATATCGGGGGTCCTY

TGACTAATTCAAAAGGGCAGAACTGCGGCTATCGCCGGTGTCGCGCAAG

CGGCGTGCTGACGACCAGCTGCGGCAATACCCTCACATGTTACCTGAAG

GCCACTGCAGCCTGTCGAGCTGCGAAGCTCCAGGACTGCACAATGCTTG

TGTGTGGGGACGACCTTGTCGTYATCTGTGAGAGCGCGGGGACCCAAGA

GGACGCAGCGAGCCTACGAGTCTTCACGGAGGCTATGACTAGGTACTCT

GCTCCCCCCGGGGACCCGCCCCGGCCGGAATACGACTTGGARTTAATAA

CATCATGCTCCTCCAACGTGTCGGTCGCGCACGACGCACAYGGCAAAAG

GGTGTACTACCTCACCCGTGACCCCACCACCCCCCTTGCGCGGGCYGCAT

GGGAGACAGCTAGACACACTCCAGTCAACTCCTGGCTAGGCAACATCATC

ATGTATGCGCCCACCTTGTGGGCAAGGATGATYCTGATGACYCATTTCTT

CTCCATCCTTCTAGCCCAGGAGCAACTTGAAAAAGCCCTAGATTGTCAGA

TCTACGGGGCCTGTTACTCCATTGAGCCACTTGACCTACCTCAGATCATT

CAGCGACTCCATGGTCTTAGCGCATTTTCACTCCACAGTTACTCTCCAGG

TGAGATCAATAGGGTGGCTTCATGCCTCAGGAAACTTGGGGTACCACCCC

TGCGAGTCTGGAGACATCGGGCCAGAAGTGTCCGCGCTAAGCTGCTGTCC

CGGGGGGGGAGGGCTGCCACTTGTGGCAAGTACCTCTTCAACTGGGCRGT

AAGGACCAAGCTCAAACTCACTCCAATCCCGGCTGCGTTCAAGCTGGACT

TGTCCGGCTGGTTCGTTGCTGGTTACAGCGGGGGAGACATATATCACAGC

CTGTCTCGTGCCCGACCCCGCTGGTTYRTGTGGTGCCTACTCCTACTTTC

TGTAGGGGTAGGCATCTACCTGCTCCCCAACCGATGA

>Pt 16 NS5B (SEQ ID NO: 227)

TCGATGTCCTACACATGGACAGGCGCCTTGATCACACCGTGCGCTGCGG

ARGAGAGCAAGCTGCCCATCAAYGCGCTGAGCAACTCTTTGYTGCGYCAC

CATAACATGGRTCTATGCCACAACATCCCGCAGCGCYAGCCAAMGGCAGAR

GAAGGTCACTTTTGAYAGACTGCARGTCCTGGACGACCACTACCGGGACG

TGCTYAAGGAGATGAAGGCGAAGGCGTCCACAGTCAAGGCTAAACTTCTA

TCCGTAGARGAAGCCTGYAAGCTGACRCCCCCACACTCGGCCAGATCYAA

ATTTGGCTATGGGGCAAAGGACGTCCGGAACCTATCCAGCAAGGCCGTTA

ACCACATCCACTCCGTGTGGAAGGACTTGCTGGAAGACACTGACACACCA

ATTGACACCACCATCATGGCAAAAAATGAGGTTTTCTGYATCCAACCAGA

-continued

GAAAGGAGGCCGCAAGCCAGCTCGCCTTATCGTRTACCCAGACCTGGGGG

TCCGRGTGTGCGAGAAGATGGCTCTTTAYGATGTGGTCTCCACYCTTCCT

CAGGCCGTGATGGGCCCCTCRTACGGATTTCAGTACTCTCCTGGACAGC

GGGTTGAGTTCCTGGTGAAWGCCTGGAARTCAAAGAAATGCCCTATGGG

CTTCGCRTATGACACCCGCTGCTTYGACTCRACGGTCACTGAGAATGACA

TYCGTGTTGAGGAGTCAATTTACCAATGTTGTGACTTGGCYCCCGAAGCC

AGACAGGYCATAAGGTCGCTCACAGAGCGGCTTTAYATCGGGGGTCCYCT

AACCAATTCAAAAGGGCAAAACTGCGGTTATCGCCGGTGTCGCGCRAGC

GGCGTGCTGACGACTAGCTGCGGCAAYACCCTTACATGTTACTTGAARGC

CTCTGCRGCCTGTCGAGCTGCGAAGCTCCAGGACTGCACGATGCTCGTG

TGCGGAGACGACCTCGTCGTTATCTGTGAGAGCGCGGGGACCCACGAGG

ATGCGGCGAGCCTACGAGTCTTYACGGAGGCTATGACTAGGTACTCCGC

CCCCCCYGGGGACCCGCCTCAGCCAGAATACGACTTAGAGCTGATAACAT

CATGCTCTTCCAAYGTGTCRGTCGCGCACGATGCATCYGGCAAAAGGGTR

TACTACCTCACCCGTGACCCCACCACCCCCCTTGCRCGGGCTGCGTGGG

-continued

ARACAGCTAGACACACTCCAGTYAACTCCTGGCTAGGCAACATCATCATG

TAYGCGCCCACCYTATGGGCAAGGATGATCCTGATGACTCATTTCTTCTC

CATCCTTCTAGCTCAGGAGCAACTTGAAAAAGCCCTAGATTGTCAGATCT

AYGGGGCCTGTTACTCCATTGAACCACTTGACCTACCTCAAATCATTCAR

CGACTCCATGGTATTAGCGCGTTTTCACTCCAYAGTTACTCTCCAGGWGA

GATCAATAGGGTGGCTTCATGCCTCAGGAAACTTGGGGTACCRCCCTTGC

GAGTCTGGAGACATCGGGCCAGGAGTGTCCGCGCTAAGYTACTGTCCCAG

GGGGGGAGGGCTGCCACTTGTGGCAARTACCTCTTCAACTGGGCAGTAAR

AACCAAGCTTAATCTCACTCCAATTCCGGCTGCGTCCAAGCTGGATTTAT

CCRGCTGGTTCGTTGCCGGYTACAGCGGGGGAGACATATATCACAGCGTG

TCTCMTGCCCGACCCCGCTGGTTCATGTGGTGCCTRCTCCTACTKTCTGT

AGGRGTAGGCATCTACCTGCTYCCCAACCGATGA

D. Alignment of Sequences with Reference Sequence

The alignment shows the nucleotide sequence of the NS5B polymerase domain of an HCV-1b isolate from an untreated patient (SEQ ID NO: 223). The sequence was aligned against a reference sequence (SEQ ID NO: 228). Homologies between the two sequences are plotted as dots.

```
                            10        20        30        40
                    ....|....|....|....|....|....|....|....|
con1b reference tcgatgtcctacacatggacaggcgccctgatcacgccat
Pt 12 NS5B      ..............G.....G.................G.

                            50        60        70        80
                    ....|....|....|....|....|....|....|....|
con1b reference gcgctgcggaggaaaccaagctgcccatcaatgcactgag
Pt 12 NS5B      ....C..........G.........T.........T....

                            90       100       110       120
                    ....|....|....|....|....|....|....|....|
con1b reference caactctttgctccgtcaccacaacttggtctatgctaca
Pt 12 NS5B      ......AC....G...........TA....T.........

                           130       140       150       160
                    ....|....|....|....|....|....|....|....|
con1b reference acatctcgcagcgcaagcctgcggcagaagaaggtcacct
Pt 12 NS5B      .....C.............A..................T.

                           170       180       190       200
                    ....|....|....|....|....|....|....|....|
con1b reference ttgacagactgcaggtcctggacgaccactaccgggacgt
Pt 12 NS5B      .............A..........................

                           210       220       230       240
                    ....|....|....|....|....|....|....|....|
con1b reference gctcaaggagatgaaggcgaaggcgtccacagttaaggct
Pt 12 NS5B      ........................................

                           250       260       270       280
                    ....|....|....|....|....|....|....|....|
con1b reference aaacttctatccgtggaggaagcctgtaagctgacgcccc
Pt 12 NS5B      ..G........T..A..............A..........

                           290       300       310       320
                    ....|....|....|....|....|....|....|....|
con1b reference cacattcggccagatctaaatttggctatggggcaaagga
Pt 12 NS5B      ................C...........Y...........

                           330       340       350       360
                    ....|....|....|....|....|....|....|....|
con1b reference cgtccggaacctatccagcaaggccgttaaccacatccgc
Pt 12 NS5B      ........................................

                           370       380       390       400
                    ....|....|....|....|....|....|....|....|
con1b reference tccgtgtggaaggacttgctggaagacactgagacaccaa
Pt 12 NS5B      ........................................

                           410       420       430       440
                    ....|....|....|....|....|....|....|....|
con1b reference ttgacaccaccatcatggcaaaaatgaggttttctgcgt
Pt 12 NS5B      .........................C.....Y........
```

-continued

```
                        450       460       470       480
                ....|....|....|....|....|....|....|....|
con1b reference ccaaccagagaaggggggccgcaagccagctcgccttatc
Pt 12 NS5B      ............A..A........................
                        490       500       510       520
                ....|....|....|....|....|....|....|....|
con1b reference gtattcccagatttgggggttcgtgtgtgcgagaaaatgg
Pt 12 NS5B      ..G........C.....A......................
                        530       540       550       560
                ....|....|....|....|....|....|....|....|
con1b reference ccctttacgatgtggtctccaccctccctcaggccgtgat
Pt 12 NS5B      ..........C...........T..T.....A........
                        570       580       590       600
                ....|....|....|....|....|....|....|....|
con1b reference gggctcttcatacggattccaatactctcctggacagcgg
Pt 12 NS5B      ......C.....T........G..................
                        610       620       630       640
                ....|....|....|....|....|....|....|....|
con1b reference gtcgagttcctggtgaatgcctggaaagcgaagaaatgcc
Pt 12 NS5B      ..T..A....................GT.......GAA..
                        650       660       670       680
                ....|....|....|....|....|....|....|....|
con1b reference ctatgggcttcgcatatgacacccgctgttttgactcaac
Pt 12 NS5B      ........................................
                        690       700       710       720
                ....|....|....|....|....|....|....|....|
con1b reference ggtcactgagaatgacatccgtgttgaggagtcaatctac
Pt 12 NS5B      A..........G.........C..................
                        730       740       750       760
                ....|....|....|....|....|....|....|....|
con1b reference caatgttgtgacttggcccccgaagccagacaggccataa
Pt 12 NS5B      ............................A...........
                        770       780       790       800
                ....|....|....|....|....|....|....|....|
con1b reference ggtcgctcacagagcggctttacatcgggggcccccctgac
Pt 12 NS5B      A..............................T........
                        810       820       830       840
                ....|....|....|....|....|....|....|....|
con1b reference taattctaaagggcagaactgcggctatcgccggtgccgc
Pt 12 NS5B      ......A.................................
                        850       860       870       880
                ....|....|....|....|....|....|....|....|
con1b reference gcgagcggtgtactgacgaccagctgcggtaataccctca
Pt 12 NS5B      ..C.....C.................T.............
                        890       900       910       920
                ....|....|....|....|....|....|....|....|
con1b reference catgttacttgaaggccgctgcggcctgtcgagctgcgaa
Pt 12 NS5B      .............A...T...................A..
                        930       940       950       960
                ....|....|....|....|....|....|....|....|
con1b reference gctccaggactgcacgatgctcgtatgcggagacgacctt
Pt 12 NS5B      ........................G...............
                        970       980       990      1000
                ....|....|....|....|....|....|....|....|
con1b reference gtcgttatctgtgaaagcgcggggacccaagaggacgagg
Pt 12 NS5B      ..............G........A.....G.......C..
                        1010      1020      1030      1040
                ....|....|....|....|....|....|....|....|
con1b reference cgagcctacgggccttcacggaggctatgactagatactc
Pt 12 NS5B      ..........A.T.....................G.....
                        1050      1060      1070      1080
                ....|....|....|....|....|....|....|....|
con1b reference tgcccccccctggggacccgcccaaaccagaatacgacttg
Pt 12 NS5B      C........C............C.G.....G.........
                        1090      1100      1110      1120
                ....|....|....|....|....|....|....|....|
con1b reference gagttgataacatcatgctcctccaatgtgtcagtcgcgc
Pt 12 NS5B      ..........................C.....G.......
                        1130      1140      1150      1160
                ....|....|....|....|....|....|....|....|
con1b reference acgatgcatctggcaaaagggtgtactatctcacccgtga
Pt 12 NS5B      ..........C......C.......T..C...........
                        1170      1180      1190      1200
                ....|....|....|....|....|....|....|....|
con1b reference ccccaccaccccccttgcgcgggctgcgtgggagacagct
Pt 12 NS5B      ...............C...A.............A......
```

-continued

```
                           1210      1220      1230      1240
                   ....|....|....|....|....|....|....|....|
con1b reference    agacacactccagtcaattcctggctaggcaacatcatca
Pt 12 NS5B         ..............T.....T.................T.

                           1250      1260      1270      1280
                   ....|....|....|....|....|....|....|....|
con1b reference    tgtatgcgcccaccttgtgggcaaggatgatcctgatgac
Pt 12 NS5B         ..............C................TT.......

                           1290      1300      1310      1320
                   ....|....|....|....|....|....|....|....|
con1b reference    tcatttcttctccatccttctagctcaggaacaacttgaa
Pt 12 NS5B         ...C.......................A............

                           1330      1340      1350      1360
                   ....|....|....|....|....|....|....|....|
con1b reference    aaagccctagattgtcagatctacggggcctgttactcca
Pt 12 NS5B         ........G.......................C.......

                           1370      1380      1390      1400
                   ....|....|....|....|....|....|....|....|
con1b reference    ttgagccacttgacctacctcagatcattcaacgactcca
Pt 12 NS5B         ...............................R........

                           1410      1420      1430      1440
                   ....|....|....|....|....|....|....|....|
con1b reference    tggccttagcgcattttcactccatagttactctccaggt
Pt 12 NS5B         ...T....................C...............

                           1450      1460      1470      1480
                   ....|....|....|....|....|....|....|....|
con1b reference    gagatcaatagggtggcttcatgcctcaggaaacttgggg
Pt 12 NS5B         ........................................

                           1490      1500      1510      1520
                   ....|....|....|....|....|....|....|....|
con1b reference    taccgcccttgcgagtctggagacatcgggccagaagtgt
Pt 12 NS5B         ........................................

                           1530      1540      1550      1560
                   ....|....|....|....|....|....|....|....|
con1b reference    ccgcgctaggctactgtcccagggggggagggctgccact
Pt 12 NS5B         ........A.............................T.

                           1570      1580      1590      1600
                   ....|....|....|....|....|....|....|....|
con1b reference    tgtggcaagtacctcttcaactgggcagtaaggaccaagc
Pt 12 NS5B         ..........................R.............

                           1610      1620      1630      1640
                   ....|....|....|....|....|....|....|....|
con1b reference    tcaaactcactccaatcccggctgcgtcccagttggattt
Pt 12 NS5B         ......................A..............C..

                           1650      1660      1670      1680
                   ....|....|....|....|....|....|....|....|
con1b reference    atccagctggttcgttgctggttacagcgggggagacata
Pt 12 NS5B         G...GA............C..C..................

                           1690      1700      1710      1720
                   ....|....|....|....|....|....|....|....|
con1b reference    tatcacagcctgtctcgtgcccgaccccgctggttcatgt
Pt 12 NS5B         ....................................C...

                           1730      1740      1750      1760
                   ....|....|....|....|....|....|....|....|
con1b reference    ggtgcctactcctactttctgtaggggtaggcatctatct
Pt 12 NS5B         .............G.......CG..............CT.

                           1770
                   ....|....|....|.
con1b reference    actccccaaccgatga
Pt 12 NS5B         G...............
```

EXAMPLE 3

NS3 Phenotyping Assay

Construction of Delta [NS3] Shuttle Vector

The plasmid 11pFK I341 PI luc NS3-3'_ET is based on the construct described in Krieger et al. 2001 and was kindly provided by Prof. Bartenschlager (Heidelberg, Germany). In order to generate a shuttle vector for NS3 phenotyping, it was modified by site-directed mutagenesis to introduce two new SacII restriction sites at position 3338 and 3899. In a next step, the modified plasmid was digested with SacII and subsequently religated to give the delta[NS3] shuttle vector pFK I341 PI luc ΔNS3 7-192_ET (SEQ ID No 10).

For InFusion cloning, the delta[NS3] backbone pFK I341 PI luc ΔNS3 7-192_ET (SEQ ID NO: 10) was linearized by SacII digestion.

EXAMPLE 4

Cloning of the NS3 PCR Amplicons from Infected Patients into the Delta[NS3] Shuttle Vector A. NS3 Amplicon Generation from Isolates of HCV-Infected Patients For the PCR, 1 μl from the One-Step RT-PCR product of the NS3 genotyping assay was mixed with 0.2 μM primer 1b_InFu_NS3_F (SEQ ID NO: 11), 0.2 μM primer 1b_InFu_NS3_R (SEQ ID NO: 12) and 2× Herculase™ Hotstart master mix (Stratagene) to give a total volume of 50 μl. Initial denaturation was 95° C. for 2 min and thermal cycling consisted of 10 cycles followed by another 20 cycles consisting of denaturation at 95° C. for 30 s, annealing at 60° C. for 30 s and elongation at 72° C. for 1 min (plus 10 s per cycle). Final extension took place at 72° C. for 10 min. The amplicons were purified using the QIAQuick gel purification kit (Qiagen).

B. Delta [NS3] Shuttle Vector Preparation

The NS3 subgenomic shuttle backbone was digested with an excess of the restriction endonuclease SacII (NEB) and 1× restriction enzyme buffer 4 (NEB) at 37° C. overnight. In a next step, calf intestine phosphatase was added and the mixture incubated for 40 min at 37° C. in order to dephosphorylate the linearized shuttle backbone. The dephosphorylated vector was purified via agarose gel electrophoresis (crystal violet) followed by gel extraction using the kit from QIAGEN. The linearized vector was stored at −20° C. until further use.

C. Cloning of the NS3 Derived from Patient Isolates into the Linearized Delta [NS3] Shuttle Vector The PCR products and the linearized vector were thawed and the PCR product was stored on ice until cloning. Immediately before the In-Fusion™ cloning, the linearized vector was denatured for 5 min at 60° C. and subsequently put on ice. For the cloning reaction, 1 μl of the PCR product and 1 μl of the vector preparation were added to 8 μl Dnase/Rnase-free water. The complete mix (10 μl) was added into one tube containing the Dry-Down In-Fusion™ reaction mix (Clontech) and carefully pipetted up and down. The pipetting steps were performed on ice. The PCR tubes containing the In-Fusion™ cloning mix were subsequently transferred to a thermocycler and incubated for 30 min at 42° C. After incubation the tubes were immediately transferred to ice.

D. Transformation of Recombinant Replicon DNA

The transformation of *Escherichia coli* cell was performed immediately after the In-Fusion™ cloning step. The XL10-Gold® Ultracompetent Cells (Stratagene) were used for the transformation. 50 μl of the cells were transformed with 5 μl of the In-Fusion™ cloning mix according to the protocol from Stratagene. The complete transformation mix was plated onto ampicillin-containing LB Petri dishes and incubated overnight at 37° C. Colonies were pooled by applying 1 ml of ampicillin-containing LB medium onto the Petri dishes and removing the colonies by scraping. The bacterial suspension was transferred into a 15 ml-Falcon tube. The Petri dishes were washed for a second time with 1 ml of the ampicillin-containing LB medium and the solution was again transferred into the Falcon tube. 2 ml of ampicillin-containing LB medium were added and cells were grown at 37° C. until they reached the logarithmic phase (approximately 4-5 hours). 1.5 ml of the cell culture was used for inoculation of 200 ml ampicillin-containing LB medium. Cells were grown overnight at 37° C. for the DNA preparation. The DNA was prepared using the Maxiprep DNA purification kit from QIAGEN.

EXAMPLE 5

Replicon NS3 Phenotypic Assay

A. Recombinant Replicon Plasmid DNA Linearization

The replicon plasmid DNA (10 μg per sample) was linearized using 1.5 μl of AseI (NEB) and 3 μl ScaI (NEB) together with 4 μl NEB buffer 3 to give a total volume of 40 μl. The reaction mix was incubated for 4 hours at 37° C. The linearized vector was separated from the resulting fragments via agarose gel electrophoresis and purified using the gel extraction kit from QIAGEN. DNA concentration was measured using the Nanodrop® spectrophotometer (ratio OD260 nm/OD280 nm). The purified DNA was stored at −20° C. until further use.

B. Preparation of In Vitro Transcribed Replicon RNA

The in vitro transcription was performed using the MEGAscript High Yield Transcription kit (Ambion) according to protocol HCV_SP__038.vs2 in the Laboratory Operation Unit at Tibotec. Briefly, 1 μg of the linearized and purified replicon DNA was used per reaction for in vitro transcription and were added to a mix containing 44 μl nuclease-free water, 4 μl ATP solution, 4 μl CTP solution, 4 μl GTP solution, 4 μl UTP solution and 10× reaction buffer. Four μl of the enzyme mix were subsequently added. The pipetting was performed at room temperature. The reaction mix was incubated for 4 hours at 37° C. Two μl of TURBO DNase (Ambion) were subsequently added and the mixture was incubated for 15 min at 37° C. in order two destroy the DNA template. The RNA was purified using the MEGAclear™ kit (Ambion). RNA was quantified using the Nanodrop® spectrophotometer (ratio OD260 nm/OD280 nm). The purified RNA was stored in 10 μg aliquots at −80° C. until further use.

C. Hepatoma Cell Line

Cured hepatoma cell line Huh7 were cultured at 37° C. in a humidified atmosphere with 5% $CO_2$ in Dulbecco's Modified Eagle medium (DMEM, Biowhittaker, Cat n° BE12-917F) supplemented with L-Glutamine and 10% FCS.

D. Determination of Transient Replicon Replication $4\times10^6$ cells were transfected with 10 μg of in vitro transcribed replicon RNA via electroporation. For $EC_{50}$ determination 4,000 cells/well were seeded in a volume of 30 μl medium in white 384-well compound plates. Compound plates contained 10 μl/well of the respective compound dilution in medium (containing 2% DMSO), leading to a total volume of 40 μl per well with a final concentration of 0.5% DMSO. Compound dilutions were prepared in quadruplates. Cell culture plates were incubated for 48 h at 37° C. and 5% $CO_2$. Experiments were performed in triplicates. The firefly luciferase chemiluminescence read-out was performed using the Steady-Lite reagent (PerkinElmer). The $EC_{50}$ values were assessed as the inhibitor concentration at which a 50% reduction in the level of firefly luciferase reporter was observed as compared to the level of firefly luciferase signal without the addition of compounds. Results of studies testing the inhibitory effect of an example protease inhibitor, SCH 503034, on replication of WT replicon and replicons with patient-derived NS3 sequences are shown in Table 2.

Table 2 shows that the NS3-restored shuttle vector is replicating. GND serves as a non-replicating replicon control.

Table 3 shows $EC_{50}$ values of an HCV protease inhibitor tested in the NS3 replicon shuttle system with 5 patient isolates.

Results:

TABLE 2

| Replication level of replicons (96-well format*) | | | |
|---|---|---|---|
| Plasmid | Vector backbone | RLU level[1] | Replication level[2] |
| rep PI-luc/ET (WT) | rep PI-luc/ET (WT) | 1637 ± 348 | |
| rep PI-luc/ET NS3 7-192 InFu restored | Rep PI-luc/ET delta [NS37-192] SacII | 1047 ± 151 | WT level |
| GND | | 17 ± 2 | No replication |

15000 cells were seeded per well in 96-well plates.
[1]RLU represents level of firefly luciferase signal observed after 48 hours post-transfection.
[2]Replication level is compared to wild type (WT) vector.

TABLE 3

| EC$_{50}$ values (384-well format) | |
|---|---|
| NS3 sequence | SCH 503034 EC$_{50}$ [μM]* |
| rep PI-luc/ET (WT) | 0.140 ± 0.069 |
| Clinical isolate Pt 1 | 0.341 ± 0.130 |
| Clinical isolate Pt 2 | 0.090 ± 0.046 |
| Clinical isolate Pt 3 | 0.124 ± 0.023 |
| Clinical isolate Pt 4 | 0.126 ± 0.018 |
| Clinical isolate Pt 5 | 0.120 ± 0.068 |

*Inhibition by SCH 503034 of transient HCV replicon RNA replication containing the NS3 from genotype 1b clinical isolates inserted into the shuttle vector pFK PI-luc delta[NS3 7-192]_ET; mean EC$_{50}$ value from at least n = 3 experiments.

EXAMPLE 6

NS5B Phenotyping Assay

Construction of Delta [NS5B] Backbone

The plasmid 11 pFK I341 PI luc NS3-3'_ET is based on the construct described in Krieger et al. 2001 and was kindly provided by Prof. Bartenschlager (Heidelberg, Germany). In order to generate a shuttle vector, it was modified by site-directed mutagenesis to introduce two AfIII restriction sites at position 7481 and 9287. First, an AfIII restriction site was introduced by site directed mutagenesis into the 3' NCR directly after the stop codon of NS5B at Medigenomix (Munich, Germany) resulting in plasmid pFKi341Luc_NS3-3'-ET-AfIII (Sequence ID NO:17). Next, a second AfIII restriction site 8aa upstream of the NS5A/NS5B cleavage site was introduced using the Quick Change Site-Directed Mutagenesis Kit (Stratagene, La Jolla, Calif., USA) according to the manufacturers recommendations with SDM primer pair AfIII-5A-fwd (5'-accgtaagcgaggag cttaaggctagtgaggacgtc-3') (Sequence ID NO:18) and AfIII-5A-rev (5'-gacgtcctcactagccttaagctcctcgcttacggt-3') (Sequence ID NO:19) resulting in plasmid pFKi341Luc_NS3-3'-ET-2×AfIII (Sequence ID NO:20). In a next step, the modified plasmid was digested with AfIII and subsequently re-ligated resulting in the delta[NS5B] backbone pFK_I341_PI_NS3-3_ET_dNS5a/b__5a440-5b591-ScaI (Sequence ID NO:21).

In parallel, a NS5B phenotyping construct with an XbaI restriction site at the 3' end was generated using plasmid pFKi341Luc_NS3-3'-ET-2×AfIII (Sequence ID NO:20) as template. First, an XbaI site in the gene of the firefly luciferase was mutated by a site directed mutagenesis approach, resulting in a silent mutation, using primer pair XbaI-mut-fwd (5'-ggcgccattctatccactagaggatggaacc-3') (Sequence ID NO:22) and XbaI-mut-rev (5'-ggttccatcctctag tggatagaatggcgcc-3') (Sequence ID NO:23). In a second SDM reaction, an XbaI restriction site was introduced at the 3' end of the HCV 3' NCR instead of the ScaI site using primer pair XbaI-add-fwd (5'-gagtgctgatactggcctctctgcagatcaag tctagaaagtccctttagtgagggttaattc-3') (Sequence ID NO:24) and XbaI-add-rev (5'-gaattaaccctcactaaaggactt tctagacttgatctgcagagaggccagtatcagcactc-3') (Sequence ID NO:25) resulting in plasmid pFKi341Luc_NS3-3'-ET-2× AfIII-XbaI (Sequence ID NO:26). In a next step, the modified plasmid was digested with AfIII and subsequently re-ligated resulting in the delta[NS5B] backbone pFK_I341_PI_NS3-3_ET_dNS5a/b__5a440-5b591-XbaI (Sequence ID NO:27). Linearization with XbaI results in an authentic HCV 3' end and offered the possibility to shuttle amplicons of clinical isolates which harbor a ScaI site in the NS5B coding sequence.

For InFusion cloning, the delta[NS5B] backbone pFK_I341_PI_NS3-3_ET_dNS5a/b__5a440-5b591-ScaI (SEQ ID NO:21) or pFK_I341_PI_NS3-3_ET_dNS5a/b__5a440-5b591-XbaI (SEQ ID NO:27) was linearized by AfIII digestion.

EXAMPLE 7

Cloning of the NS5B PCR Amplicons from HCV-Infected Patients into the Delta [NS5B] Shuttle Vector A. NS5B Amplicon Generation from Isolates of HCV-Infected Patients For the InFusion™ PCR, 1 μl from the One-Step RT-PCR product of the NS5B genotyping assay was mixed with 0.2 μM primer 1b_NS5B_F_AfIII-Infusion (5'-AAGCGAG-GAGCTTAAGGCYRGTGAGGACGT-3') (SEQ ID NO:28), 0.2 μM primer 1b_NS5B_R_AfIII-Infusion (5'-AGCTC-CCCGTCTTAAGTCAYCGGT TGGGG-3') (SEQ ID NO:29) and 2× Herculase™ Hotstart master mix (Stratagene, La Jolla, Calif., U.S.) to give a total volume of 50 μl. Initial denaturation was 95° C. for 2 min and thermal cycling consisted of 10 cycles followed by another 20 cycles consisting of denaturation at 95° C. for 30 s, annealing at 60° C. for 30 s and elongation at 72° C. for 1 min 30 s (plus 10 s per cycle). Final extension took place at 72° C. for 10 min. The amplicons were purified using the QIAQuick gel purification kit (Qiagen, Hilden, Germany). Final volume of purified amplicons was 30 μl.

B. Delta [NS5B] Shuttle Vector Preparation

The NS5B subgenomic shuttle backbone was digested with an excess of the restriction endonuclease AfIII (NEB) and 1× restriction enzyme buffer 4 (NEB) at 37° C. overnight. In a next step, calf intestine phosphatase was added and the mixture incubated for 1 h at 37° C. in order to dephosphorylate the linearized shuttle backbone. The dephosphorylated vector was purified via agarose gel electrophoresis (crystal violet) followed by gel extraction using the kit from QIAGEN. The linearized vector was stored at −20° C. until further use.

C. Cloning of the NS5B Derived from Patient Isolates into the Linearized Delta [NS5B] Shuttle Vector The PCR products and the linearized vector were thawed and the PCR product was stored on ice until cloning. Immediately before the In-Fusion™ cloning, the linearized vector was denatured for 5 min at 60° C. and subsequently put on ice. For the cloning reaction, 2 μl of the PCR product and 1-3 μl of the vector preparation were added to 5-8 μl Dnase/Rnase-free water. The complete mix (10 μl) was added into one tube containing the Dry-Down In-Fusion™ reaction mix (Clontech) and carefully pipetted up and down. The pipetting steps were performed on ice. The PCR tubes containing the In-Fusion™ cloning mix were subsequently transferred to a thermocycler and incubated for 30 min at 42° C. After incubation the tubes were immediately transferred to ice D. Transformation of Recombinant Replicon DNA The transformation of *Escherichia coli* cell was performed immediately after the In-Fusion™ cloning step. The XL10-Gold® Ultracompetent Cells (Stratagene) were used for the transformation. 50 μl of the cells were transformed with 5 μl of the In-Fusion™ cloning mix according to the protocol from Stratagene. The complete transformation mix was plated onto ampicillin-containing LB Petri dishes and incubated overnight at 37° C. Colonies were pooled by applying 1 ml of ampicillin-containing LB medium onto the Petri dishes and removing the colonies by scraping. The bacterial suspension was transferred into a 15 ml-Falcon tube. The Petri dishes were washed for a second time with 1 ml of the ampicillin-containing LB medium and the solution was again transferred into the Falcon tube. 2 ml of ampicillin-containing LB medium were added and cells were grown at 37° C. until they reached the logarithmic phase (approximately 4-5 hours). 1.5 ml of the cell culture was used for inoculation of 200 ml ampicillin-containing LB medium. Cells were grown overnight at 37° C. for the DNA preparation. The DNA was prepared using the Maxiprep DNA purification kit from QIAGEN.

EXAMPLE 8

Replicon NS5B Phenotypic Assay

A. Recombinant Replicon Plasmid DNA Linearization

The replicon plasmid DNA (10 μg per sample) was linearized using 3 μl of XbaI (NEB) together with 10 μl NEB buffer 4 and 1 μl of a 100× concentrated BSA stock solution (NEB) to give a total volume of 100 μl. The reaction mix was incubated for 4 hours at 37° C. The linearized vector was separated from the resulting fragments via agarose gel electrophoresis and purified using the gel extraction kit from QIAGEN. DNA concentration was measured using the Nanodrop® spectrophotometer (ratio OD260 nm/OD280 nm). The purified DNA was stored at −20° C. until further use.

B. Preparation of In Vitro Transcribed Replicon RNA

The in vitro transcription was performed using the MEGAscript High Yield Transcription kit (Ambion) according to protocol HCV_SP__038.vs2 in the Laboratory Operation Unit at Tibotec. Briefly, 1 μg of the linearized and purified replicon DNA was used per reaction for in vitro transcription and were added to a mix containing 44 μl nuclease-free water, 4 μl ATP solution, 4 μl CTP solution, 4 μl GTP solution, 4 μl UTP solution and 10× reaction buffer. Four μl of the enzyme mix were subsequently added. The pipetting was performed at room temperature. The reaction mix was incubated for 4 hours at 37° C. Two μl of TURBO DNase (Ambion) were subsequently added and the mixture was incubated for 15 min at 37° C. in order two destroy the DNA template. The RNA was purified using the MEGAclear™ kit (Ambion). RNA was quantified using the Nanodrop® spectrophotometer (ratio OD260 nm/OD280 nm). The purified RNA was stored in 10 μg aliquots at −80° C. until further use.

C. Hepatoma Cell Line

Cured hepatoma cell line Huh7 were cultured at 37° C. in a humidified atmosphere with 5% $CO_2$ in Dulbecco's Modified Eagle medium (DMEM, Biowhittaker, Cat n° BE12-917F) supplemented with L-Glutamine and 10% FCS.

D. Determination of Transient Replicon Replication $4\times10^6$ cells were transfected with 10 μg of in vitro transcribed replicon RNA via electroporation. For $EC_{50}$ determination 4,000 cells/well were seeded in a volume of 30 μl medium in white 384-well compound plates. Compound plates contained 10 μl/well of the respective compound dilution in medium (containing 2% DMSO), leading to a total volume of 40 μl per well with a final concentration of 0.5% DMSO. Compound dilutions were prepared in quadruplates. Cell culture plates were incubated for 48 h at 37° C. and 5% $CO_2$. Experiments were performed in at least duplicates. The firefly luciferase chemiluminescence read-out was performed using the Steady-Lite reagent (PerkinElmer). The $EC_{50}$ values were assessed as the inhibitor concentration at which a 50% reduction in the level of firefly luciferase reporter was observed as compared to the level of firefly luciferase signal without the addition of compounds. Results of studies testing the inhibitory effect of an example polymerase inhibitor, Thiophene-2-carboxylic acid, on replication of WT replicon and replicons with patient-derived NS5B sequences are shown in Table 4.

Table 4 shows $EC_{50}$ values of an HCV polymerase inhibitor tested in the NS5B replicon shuttle system with 5 patient isolates.

Results:

TABLE 4

| $EC_{50}$ values (384-well format) | |
|---|---|
| NS5B sequence | Thiophene-2-carboxylic acid $EC_{50}$ [μM]* |
| Rep PI-luc/ET (WT) | 0.58 |
| Clinical isolate Pt_12 | 0.28 |
| Clinical isolate Pt_13 | 0.59 |
| Clinical isolate Pt_14 | 1.0** |
| Clinical isolate Pt_15 | 0.63 |
| Clinical isolate Pt_16 | 3.96 |

*Inhibition by Thiophene-2-carboxylic acid of transient HCV replicon RNA replication containing the NS5B from genotype 1b clinical isolates inserted into the shuttle vector pFK PI-luc delta[NS5B]_ET; mean $EC_{50}$ value from at least n = 2 experiments.
**measured once

TABLE 5

| SEQ ID NO | Primer name | Sequence (5' to 3') | Remark | Amplification/ Sequencing |
|---|---|---|---|---|
| 1 | NS5Bsubtype_A | TGGGGTTCGCGTA TGATACCCGCTGC TTTGA | NS5B sequence-based subtyping assay | Amplification |
| 2 | NS5Bsubtype_B | TGGGGTTTTCTTA CGACACCAGGTG CTTTGA | NS5B sequence-based subtyping assay | Amplification |

TABLE 5-continued

| SEQ ID NO | Primer name | Sequence (5' to 3') | Remark | Amplification/ Sequencing |
|---|---|---|---|---|
| 3 | NS5Bsubtype_C | CCGTATGATACCC GCTGCTTTGACTC AAC | NS5B sequence-based subtyping assay | Amplification and sequencing |
| 4 | NS5Bsubtype_D | TCCTACGACACCA GGTGCTTTGATTC AAC | NS5B sequence-based subtyping assay | Amplification and sequencing |
| 5 | NS5Bsubtype_E | AATTCCTGGTCAT AGCCTCCGTGAA GACTC | NS5B sequence-based subtyping assay | Amplification and sequencing |
| 6 | 1b_NS3_out_F | GCGTGTGGGGAC ATCATCTTAGG | N-terminal 181aa of NS3 genotyping assay | Amplification |
| 7 | 1b_NS3_out_R | GCTGCCAGTGGG AGCGTG | N-terminal 181aa of NS3 genotyping assay | Amplification |
| 8 | 1b_NS3_in_F | TCATCTTAGGCCT GCCCGTCTC | N-terminal 181aa of NS3 genotyping assay | Amplification and sequencing |
| 9 | 1b_NS3_in_R | GGGAGCGTGTAG ATGGGCCAC | N-terminal 181aa of NS3 genotyping assay | Amplification and sequencing |
| 10 | pFK I341 PI luc deltaNS3 7-192_ET | Plasmid sequence of delta[NS3] backbone | Phenotyping shuttle backbone | NA |
| 11 | 1b_InFu_NS3_F | ATGGCGCCTATTA CCGCCTACTCCCA ACAGACG | Phenotyping amplification primer | Amplification |
| 12 | 1b_InFu_NS3_R | AATGTCTGCGGTA CCGCCGGGGGGG ATGAGTTGTC | Phenotyping amplification primer | Amplification |
| 13 | 1b_NS5B_out_F | TAGAGTCCTGGA AGGACCCGG | Polymerase (NS5B) genotyping assay | Amplification |
| 14 | 1b_NS5B_out_R | GGCCTGGAGTGG TTAGCTCCCC | Polymerase (NS5B) genotyping assay | Amplification |
| 15 | 1b_NS5B_in_F | TGGAAGGACCCG GACTACG | Polymerase (NS5B) genotyping assay | Amplification and sequencing |
| 16 | 1b_NS5B_in_R | GAGTGGTTAGCTC CCCGTTCA | Polymerase (NS5B) genotyping assay | Amplification and sequencing |
| 17 | pFKi341Luc_NS3-3'-ET-AflII | plasmid with 1st AflII site (intermediate plasmid) | Phenotyping shuttle backbone | NA |
| 18 | AflII-5A-fwd | (5'-accgtaagcgaggag cttaaggctagtgaggacgtc-3') SDM primer | Phenotyping for cloning | |
| 19 | AflII-5A-rev | (5'-gacgtcctcactagcctt aagctcctcgcttacggt-3' SDM primer | Phenotyping for cloning | |
| 20 | pFKi341Luc_NS3-3'-ET-2xAflII | plasmid with 2nd AFLii SITE (intermediate plasmid) | Phenotyping shuttle backbone | NA |
| 21 | pFK_I341_PI_NS3-3_ET_dNS5A/ | Plasmid sequence of delta[NS5B] ScaI | Phenotyping shuttle backbone | NA |

TABLE 5-continued

| SEQ ID NO | Primer name | Sequence (5' to 3') | Remark | Amplification/ Sequencing |
|---|---|---|---|---|
| | b_5a440-5b591-ScaI | backbone | | |
| 22 | XbaI-mut-fwd | (5'-ggcgccattctatccac tagaggatggaacc-3') SDM primer | Phenotyping for cloning | |
| 23 | XbaI-mut-rev | (5'-ggttccatcctctagtg gatagaatggcgcc-3') SDM primer | Phenotyping for cloning | |
| 24 | XbaI-add-fwd | (5'-gagtgctgatactggcc tctctgcagatcaagtctaga aagtccctttagtgagggtta attc-3') | Phenotyping for cloning | |
| 25 | XbaI-add-rev | (5'-gaattaaccctcactaaa gggactttctagacttgatctg cagagaggccagtatcagc actc-3') | Phenotyping for cloning | |
| 26 | pFKi341Luc_NS3-3'-ET-2xAfl II-XbaI | Intermediate plasmid | Phenotyping shuttle backbone | NA |
| 27 | pFK_I341_PI_NS3-3_ET_dNS5A/ b_5a440-5b591-XbaI | Plasmid sequence of delta[NS5B] XbaI backbone | Phenotyping shuttle backbone | NA |
| 28 | 1b_NS5B_F_AflII-Infusion | AAGCGAGGAGCT TAAGGCYRGTGA GGACGT | Phenotyping amplification primer | Amplification |
| 29 | 1b_NS5B_R_AflII-Infusion | AGCTCCCCGTCTT AAGTCAYCGGTT GGGG | Phenotyping amplification primer | Amplification |
| 30 | 1a_NS3/4A_out_R | GGGACCTCACCG CTCATGAT | Protease (NS3/4A) genotyping assay | Amplification |
| 31 | 1a_NS3/4A_in_R | CTCACCGCTCATG ATCTTGAATGC | Protease (NS3/4A) genotyping assay | Amplification |
| 32 | 1a_NS3/4A_out_F | CGGAGGTCATTA CGTGCAAATG | Protease (NS3/4A) genotyping assay | Amplification |
| 33 | 1a_NS3/4A_in_F | CGTGCAAATGGC CATCATCAAG | Protease (NS3/4A) genotyping assay | Amplification |
| 34 | 1a_NS2_F1sb | GCGCTTACTGGCA CCTATG | Protease (NS3/4A) genotyping assay | Sequencing |
| 35 | 1a_NS3_F1s | AGGCACGCCGAT GTCAT | Protease (NS3/4A) genotyping assay | Sequencing |
| 36 | 1a_NS3_R2s | CGGGACCTTGGT GCTCTT | Protease (NS3/4A) genotyping assay | Sequencing |
| 37 | 1a_NS3_F2s | CGGCACTGTCCTT GACCA | Protease (NS3/4A) genotyping assay | Sequencing |
| 38 | 1a_NS3_R3s | GAGTCGAAGTCG CCGGTA | Protease (NS3/4A) genotyping assay | Sequencing |
| 39 | 1a_NS3_F3s | CCGAGACTACAG TTAGGCTACG | Protease (NS3/4A) genotyping assay | Sequencing |
| 40 | 1a_NS3_R4s | GCATGTCATGATG TATTTGGTG | Protease (NS3/4A) genotyping assay | Sequencing |
| 41 | 1a_NS4B_R1s | ACGAGGACCTTC CCCAGT | Protease (NS3/4A) and NS4B/5A genotyping assay | Sequencing |

TABLE 5-continued

| SEQ ID NO | Primer name | Sequence (5' to 3') | Remark | Amplification/ Sequencing |
|---|---|---|---|---|
| 42 | 1a_NS3_out_R | GCTGCCGGTGGG AGCATG | N-terminal 181aa of NS3 genotyping assay | Amplification |
| 43 | 1a_NS3_in_R | GAGCATGCAGGT GGGCCAC | N-terminal 181aa of NS3 genotyping assay | Amplification and sequencing |
| 44 | 1a_NS3_out_F | GCGGCGACATCA TCAACGG | N-terminal 181aa of NS3 genotyping assay | Amplification |
| 45 | 1a_NS3_in_F | CATCAACGGCTTG CCCGTCTC | N-terminal 181aa of NS3 genotyping assay | Amplification and sequencing |
| 46 | 1a_NS3_Fs_BU | GACCTTTACCTGG TCACGAG | N-terminal 181aa of NS3 genotyping assay | Sequencing |
| 47 | 1a_NS4B/5A_out_R | GCTGTCCAGAACT TGCAGTCTGTC | NS4B/5A genotyping assay | Amplification |
| 48 | 1a_NS4B/5A_in_R | CCTTTGGCAAGCA CTGCGTG | NS4B/5A genotyping assay | Amplification |
| 49 | 1a_NS4B/5A_out_F | CTGCGTGGTCATA GTGGGCAG | NS4B/5A genotyping assay | Amplification |
| 50 | 1a_NS4B/5A_in_F | TGTCTTGTCCGGG AAGCCGG | NS4B/5A genotyping assay | Amplification |
| 51 | 1a_NS4B_F2s | CGTCACTGCCATA CTCAGCA | NS4B/5A genotyping assay | Sequencing |
| 52 | 1a_NS5A_R1s | CGTCCCGTTTTTG ACATG | NS4B/5A genotyping assay | Sequencing |
| 53 | 1a_NS5A_R2s | TGACTCAACCCTG GTGATGTT | NS4B/5A genotyping assay | Sequencing |
| 54 | 1a_NS5A_F2s | CGGTGGTCCTCAC CGAA | NS4B/5A and Polymerase (NS5B) genotyping assay | Sequencing |
| 55 | 1a_NS4A_F1s | TTGTCCGGGAAG CCG | NS4B/5A genotyping assay | Sequencing |
| 56 | 1a_NS5B_R1s | TGGCAAGCACTG CGTG | NS4B/5A genotyping assay | Sequencing |
| 57 | 1a_NS5A_F1s | TTGACGTCCATGC TCACTG | NS4B/5A genotyping assay | Sequencing |
| 58 | 1a_NS5B_out_R | AGGCCGGAGTGT TTACCCCAAC | Polymerase (NS5B) genotyping assay | Amplification |
| 59 | 1a_NS5B_in_R | GGAGTGTTTACCC CAACCTTCA | Polymerase (NS5B) genotyping assay | Amplification and sequencing |
| 60 | 1a_NS5B_out_F | TGACTATGAACC ACCTGTGGTCC | Polymerase (NS5B) genotyping assay | Amplification |
| 61 | 1a_NS5B_in_F | CACCTGTGGTCCA TGGCTG | Polymerase (NS5B) genotyping assay | Amplification and sequencing |
| 62 | 1a_NS5B_F1s | CATCAACTCCGTG TGGAAAG | Polymerase (NS5B) genotyping assay | Sequencing |

TABLE 5-continued

| SEQ ID NO | Primer name | Sequence (5' to 3') | Remark | Amplification/ Sequencing |
|---|---|---|---|---|
| 63 | 1a_NS5B_R1s | CAGCGGGTATCA TACGAGAA | Polymerase (NS5B) genotyping assay | Sequencing |
| 64 | 1a_NS5B_F2s | GCACCATGCTCGT GTGTG | Polymerase (NS5B) genotyping assay | Sequencing |
| 65 | 1a_NS5B_R2s | GTCATCAGTATCA TCCTCGCC | Polymerase (NS5B) genotyping assay | Sequencing |
| 66 | 1a_NS5B_F3s | CGACTCCATGGTC TTAGCG | Polymerase (NS5B) genotyping assay | Sequencing |
| 67 | 1b_NS3/4A_out_R | GAGCGCCTTCTGT TTGAATTG | Protease (NS3/4A) genotyping assay | Amplification |
| 68 | 1b_NS3/4A_in_R | CTGTTTGAATTGC TCGGCGAG | Protease (NS3/4A) genotyping assay | Amplification and sequencing |
| 69 | 1b_NS3/4A_out_F | ATGCATGCTGGTG CGGAA | Protease (NS3/4A) genotyping assay | Amplification |
| 70 | 1b_NS3/4A_in_F | TGGTGCGGAAAG TCGCTGG | Protease (NS3/4A) genotyping assay | Amplification |
| 71 | 1b_NS2_F1s | GGTCATTATGTCC AAATGGC | Protease (NS3/4A) genotyping assay | Sequencing |
| 72 | 1b_NS3_F1s | CGGCAGCTCGGA CCTTTA | Protease (NS3/4A) genotyping assay | Sequencing |
| 73 | 1b_NS3_R2s | CACTTGGAATGTC TGCGGTAC | Protease (NS3/4A) genotyping assay | Sequencing |
| 74 | 1b_NS3_F2s | GATGAGTGCCAC TCAACTGACT | Protease (NS3/4A) genotyping assay | Sequencing |
| 75 | 1b_NS3_R3s | CGTCTGTTGCCAC GACAA | Protease (NS3/4A) genotyping assay | Sequencing |
| 76 | 1b_NS3_F3s | CTATGACGCGGG CTGTG | Protease (NS3/4A) genotyping assay | Sequencing |
| 77 | 1b_NS3_R4s | AGCCGTATGAGA CACTTCCAC | Protease (NS3/4A) genotyping assay | Sequencing |
| 78 | 1b_NS4B/5A_out_R | GCATAGACCATG TTGTGGTGACG | NS4B/5A genotyping assay | Amplification |
| 79 | 1b_NS4B/5A_in_R | GTGACGCAGCAA AGAGTTGCTCA | NS4B/5A genotyping assay | Amplification and sequencing |
| 80 | 1b_NS4B/5A_out_F | AGCGTGGTCATTG TGGGCAG | NS4B/5A genotyping assay | Amplification |
| 81 | 1b_NS4B/5A_in_F | GGGCAGGATCAT CTTGTCCGG | NS4B/5A genotyping assay | Amplification and sequencing |
| 82 | 1b_NS4B_R1s | TTCCCAAGGCCTA TGCTG | NS4B/5A genotyping assay | Sequencing |
| 83 | 1b_NS4B_F2s | GGATGAACCGGC TGATAGC | NS4B/5A genotyping assay | Sequencing |
| 84 | 1b_NS5A_R1s | ATGGAACCGTTTT TGACATGT | NS4B/5A genotyping assay | Sequencing |
| 85 | 1b_NS5A_F1s | GGGCATGACCAC TGACAAC | NS4B/5A genotyping assay | Sequencing |

TABLE 5-continued

| SEQ ID NO | Primer name | Sequence (5' to 3') | Remark | Amplification/ Sequencing |
|---|---|---|---|---|
| 86 | 1b_NS5A_R2s | CCACAGGAGGTT GGCCT | NS4B/5A genotyping assay | Sequencing |
| 87 | 1b_NS5A_F2s | CACGGGTGCCCA TTGC | NS4B/5A and Polymerase (NS5B) genotyping assay | Sequencing |
| 88 | 1b_NS5B_F1s | AAGGAGATGAAG GCGAAGG | Polymerase (NS5B) genotyping assay | Sequencing |
| 89 | 1b_NS5B_R1s | CATCACGGCCTG AGGAAG | Polymerase (NS5B) genotyping assay | Sequencing |
| 90 | 1b_NS5B_F2s | TCGCTCACAGAG CGGCT | Polymerase (NS5B) genotyping assay | Sequencing |
| 91 | 1b_NS5B_R2s | TGGAGGAGCATG ATGTTATCA | Polymerase (NS5B) genotyping assay | Sequencing |
| 92 | 1b_NS5B_F3s | CGACTCCATGGTC TTAGCG | Polymerase (NS5B) genotyping assay | Sequencing |
| 93 | 2a_NS3/4A in_F | GTAGGTGGACTG GCACTTACATCTA TGA | Protease (NS3/4A) genotyping assay | Amplification |
| 94 | 2a_NS3/4A out_F | CGCTATTAGCCCT TGGTAGGTGG | Protease (NS3/4A) genotyping assay | Amplification |
| 95 | 2a_NS3/4A in_R | AAATGCCCGCAC CATACCC | Protease (NS3/4A) genotyping assay | Amplification and sequencing |
| 96 | 2a_NS3/4A out_R | GGCTTCTCGCCAG ACATGATCTT | Protease (NS3/4A) genotyping assay | Amplification |
| 97 | 2a_NS2_F2sb | CACGGACTTCCCG TGTC | Protease (NS3/4A) genotyping assay | Sequencing |
| 98 | 2a_NS3_R1sb | TGCCAGTTGGGG CATG | Protease (NS3/4A) genotyping assay | Sequencing |
| 99 | 2a_NS3_F1s | TCCGGGCAGCTGT GTG | Protease (NS3/4A) genotyping assay | Sequencing |
| 100 | 2a_NS3_R2s | CGTCTTGAGGGA CAGTCTGTG | Protease (NS3/4A) genotyping assay | Sequencing |
| 101 | 2a_NS3_F2s | GGAGGGTGAGAT CCCCTTCTA | Protease (NS3/4A) genotyping assay | Sequencing |
| 102 | 2a_NS4B_R1s | GAAGTTCCACAT GTGTTTGGC | Protease (NS3/4A) genotyping assay | Sequencing |
| 103 | 2a_NS3_F3s | GTAGTGCTCTGTG AGTGCTACG | Protease (NS3/4A) genotyping assay | Sequencing |
| 104 | 2a_NS3_in_F | ATCTTACACGGAC TCCCCGTGTC | N-terminal 181aa of NS3 genotyping assay | Amplification and sequencing |
| 105 | 2a_NS3_out_F | ATGCGGGGACAT CTTACACGG | N-terminal 181aa of NS3 genotyping assay | Amplification |
| 106 | 2a_NS3_in_R | TGGGGCATGCAA GTACCCGAC | N-terminal 181aa of NS3 genotyping assay | Amplification and sequencing |

TABLE 5-continued

| SEQ ID NO | Primer name | Sequence (5' to 3') | Remark | Amplification/ Sequencing |
|---|---|---|---|---|
| 107 | 2a_NS3_out_R | CACTGCCAGTTGG GGCATG | N-terminal 181aa of NS3 genotyping assay | Amplification |
| 108 | 2b_NS3/4A_in_F | TACGGATACCAT ACTTTGTGAGGGC | Protease (NS3/4A) genotyping assay | Amplification |
| 109 | 2b_NS3/4A_out_F | TCTCTGCTACGGA TACCATACTTTG | Protease (NS3/4A) genotyping assay | Amplification |
| 110 | 2b_NS3/4A_in_R | TCCACCAGTATCT TACCCAGGCCTA | Protease (NS3/4A) genotyping assay | Amplification |
| 111 | 2b_NS3/4A_out_R | ACGTCCACCAGT ATCTTACCCA | Protease (NS3/4A) genotyping assay | Amplification |
| 112 | 2b_NS2_F1s | ACGAGTGTGTAC CCTGGTGA | Protease (NS3/4A) genotyping assay | Sequencing |
| 113 | 2b_NS3_F1s | GACCCCTGTACCT GCGG | Protease (NS3/4A) genotyping assay | Sequencing |
| 114 | 2b_NS3_R2s | GCAAGTAGCCCA CCTGGTAAG | Protease (NS3/4A) genotyping assay | Sequencing |
| 115 | 2b_NS3_F2s | GCCATTCAGTGG ACGCCAC | Protease (NS3/4A) genotyping assay | Sequencing |
| 116 | 2b_NS3_R3s | CCTTGAGTTGGTA TAACGGAGAC | Protease (NS3/4A) genotyping assay | Sequencing |
| 117 | 2b_NS3_F3s | GCTCTGTGAGTGC TATGATGC | Protease (NS3/4A) genotyping assay | Sequencing |
| 118 | 2b_NS3_R4s | GGTAGGACCAGT CAGTGTAGGTTT | Protease (NS3/4A) genotyping assay | Sequencing |
| 119 | 2b_NS4B_R1s | CAACGAAGCCAG TGGCTC | Protease (NS3/4A) genotyping assay | Sequencing |
| 120 | 2b_NS3_in_F | TGCATGGCCTCCC GGTTTC | N-terminal 181aa of NS3 genotyping assay | Amplification and sequencing |
| 121 | 2b_NS3_out_F | CATGTGGAGACA TCCTGCATGG | N-terminal 181aa of NS3 genotyping assay | Amplification |
| 122 | 2b_NS3_in_R | TTGGTGCATGCAA GTAGCCCAC | N-terminal 181aa of NS3 genotyping assay | Amplification and sequencing |
| 123 | 2b_NS3_out_R | CGCTGCCTGTTGG TGCATG | N-terminal 181aa of NS3 genotyping assay | Amplification |
| 124 | 2b_NS5B_in_F | CTTCTGTACCATC AGAGTACCTGAT CA | Polymerase (NS5B) genotyping assay | Amplification and sequencing |
| 125 | 2b_NS5B_out_F | GTGAGCCTTCTGT ACCATCAGAGTAC | Polymerase (NS5B) genotyping assay | Amplification |
| 126 | 2b_NS5B_out_R | ATGGAGTGTAGC TAGGGTTTGCC | Polymerase (NS5B) genotyping assay | Amplification |
| 127 | 2b_NS5B_R_in | TGTAGCTAGGGTT TGCCGCTCTA | Polymerase (NS5B) genotyping assay | Amplification and sequencing |
| 128 | 2b_NS5A_F2s | GAACCACCCACT GTCCTAGG | Polymerase (NS5B) genotyping assay | Sequencing |

TABLE 5-continued

| SEQ ID NO | Primer name | Sequence (5' to 3') | Remark | Amplification/ Sequencing |
|---|---|---|---|---|
| 129 | 2b_NS5B_F1s | GCACACTATGACT CAGTCTTGCA | Polymerase (NS5B) genotyping assay | Sequencing |
| 130 | 2b_NS5B_R1s | CATCTTTTCGCAC ACCCTG | Polymerase (NS5B) genotyping assay | Sequencing |
| 131 | 2b_NS5B_F2s | TACGTAGGAGGG CCCATG | Polymerase (NS5B) genotyping assay | Sequencing |
| 132 | 2b_NS5B_R2s | AGCGCTACCGAT ACGTTTG | Polymerase (NS5B) genotyping assay | Sequencing |
| 133 | 2b_NS5B_F3s | CCGGCCATAATTG AAAGG | Polymerase (NS5B) genotyping assay | Sequencing |
| 134 | 3a_NS3/4A_in_F | ATGCTCGTGCGCT CCGTGAT | Protease (NS3/4A) genotyping assay | Amplification |
| 135 | 3a_NS3/4A_out_F | CTTTGCATGCTCG TGCGCTC | Protease (NS3/4A) genotyping assay | Amplification |
| 136 | 3a_NS3/4A_in_R | TACTATGGGCTCA ATGACAGCTTGTTG | Protease (NS3/4A) genotyping assay | Amplification and sequencing |
| 137 | 3a_NS3/4A_out_R | GGTAGCTACTATG GGCTCAATGACA GC | Protease (NS3/4A) genotyping assay | Amplification |
| 138 | 3a_NS2_F1s | TACTTCCAGATGA TCATACTGAGC | Protease (NS3/4A) genotyping assay | Sequencing |
| 139 | 3a_NS3_F1s | ACTTATACTTGGT TACCCGCG | Protease (NS3/4A) genotyping assay | Sequencing |
| 140 | 3a_NS3_R2s | TCTTACCGCTGCC GGTC | Protease (NS3/4A) genotyping assay | Sequencing |
| 141 | 3a_NS3_F2s | TCTTAGATCAGGC TGAGACGG | Protease (NS3/4A) genotyping assay | Sequencing |
| 142 | 3a_NS3_R3s | CTGTTGTTGGTAT GACGGACA | Protease (NS3/4A) genotyping assay | Sequencing |
| 143 | 3a_NS3_F3s | AGCCCGCTGAGA CCACA | Protease (NS3/4A) genotyping assay | Sequencing |
| 144 | 3a_NS3_R4s | ATGTAGTGTTGGC TTAAGCCG | Protease (NS3/4A) genotyping assay | Sequencing |
| 145 | 3a_NS3_out_R | CTGCCGGTCGGG GCATG | N-terminal 181aa of NS3 genotyping assay | Amplification |
| 146 | 3a_NS3_in_R | GGTCGGGGCATG AAGGTATCCTAC | N-terminal 181aa of NS3 genotyping assay | Amplification and sequencing |
| 147 | 3a_NS3_out_F | CTTGCGGAGATAT TCTTTGCGG | N-terminal 181aa of NS3 genotyping assay | Amplification |
| 148 | 3a_NS3_in_F | TTGCGGGCTGCCC GTCTC | N-terminal 181aa of NS3 genotyping assay | Amplification and sequencing |
| 149 | 3a_NS4B/5A_out_R | CGACGTTGAATA GACTAGGTTATG ATGTCT | NS4B/5A genotyping assay | Amplification |
| 150 | 3a_NS4B/5A_out_F | CCCTAGCGGCCTA CTGCTTG | NS4B/5A genotyping assay | Amplification |

TABLE 5-continued

| SEQ ID NO | Primer name | Sequence (5' to 3') | Remark | Amplification/ Sequencing |
|---|---|---|---|---|
| 151 | 3a_NS4B/5A_in_F | GGCCTACTGCTTG TCAGTCGG | NS4B/5A genotyping assay | Amplification |
| 152 | 3a_NS4A_F1s | GCCTACTGCTTGT CAGTCGG | NS4B/5A genotyping assay | Sequencing |
| 153 | 3a_NS4B_R1s | ATACCCCCTATGG CAGCG | NS4B/5A genotyping assay | Sequencing |
| 154 | 3a_NS4B_F2s | ACAGTGGATGAA CAGGCTCAT | NS4B/5A genotyping assay | Sequencing |
| 155 | 3a_NS5A_R1s | TGACAGGAAATG AAGGGCAG | NS4B/5A genotyping assay | Sequencing |
| 156 | 3a_NS5A_F1s | TGAAGTGGATGG GGTGAGA | NS4B/5A genotyping assay | Sequencing |
| 157 | 3a_NS5A_R2s | TGAGGCCTATGC GTCTGG | NS4B/5A genotyping assay | Sequencing |
| 158 | 3a_NS5A_F2s | CACCAACTGTCG ATGGATG | NS4B/5A and Polymerase (NS5B) genotyping assay | Sequencing |
| 159 | 3a_NS4B/5A_in_R | TTATGATGTCTCA ACAAGGAGTTGC TGA | NS4B/5A genotyping assay | Amplification and sequencing |
| 160 | 3a_NS5B_out_R | AGTGTTATCTTAC CAGCTCACCGAGC | Polymerase (NS5B) genotyping assay | Amplification |
| 161 | 3a_NS5B_in_R | ATCTTACCAGCTC ACCGAGCTGGC | Polymerase (NS5B) genotyping assay | Amplification and sequencing |
| 162 | 3a_NS5B_out_F | GTATCCTCCAGCC CTTCCTATCTG | Polymerase (NS5B) genotyping assay | Amplification |
| 163 | 3a_NS5B_in_F | CAGCCCTTCCTAT CTGGGCTAG | Polymerase (NS5B) genotyping assay | Amplification and sequencing |
| 164 | 3a_NS5B_F1s | TCGGGTATAGTGC GAAGGA | Polymerase (NS5B) genotyping assay | Sequencing |
| 165 | 3a_NS5B_R1s | CTTCAGCAGACGT TCGACC | Polymerase (NS5B) genotyping assay | Sequencing |
| 166 | 3a_NS5B_F2s | TACATCAAGGCC ACAGCG | Polymerase (NS5B) genotyping assay | Sequencing |
| 167 | 3a_NS5B_R2s | CTGGAGTGTGAC GAGCTGTT | Polymerase (NS5B) genotyping assay | Sequencing |
| 168 | 3a_NS5B_F3s | CTTGGAGACATC GGGCAC | Polymerase (NS5B) genotyping assay | Sequencing |
| 169 | 4a/d_NS3/4A_in_F | GCGCGTCCCTTAC TTCGTGAG | Protease (NS3/4A) genotyping assay | Amplification |
| 170 | 4a/d_NS3/4A_out_F | GCTCCTGCGCGTC CCTTAC | Protease (NS3/4A) genotyping assay | Amplification |
| 171 | 4a/d_NS3/4A_in_R | GTAGCCAGCGAG GATGTCCACTAG | Protease (NS3/4A) genotyping assay | Amplification and sequencing |

TABLE 5-continued

| SEQ ID NO | Primer name | Sequence (5' to 3') | Remark | Amplification/ Sequencing |
|---|---|---|---|---|
| 172 | 4a/d_NS3/4A_out_R | CATCTCGCCGCTC ATGATCTT | Protease (NS3/4A) genotyping assay | Amplification |
| 173 | 4a/d_NS2_F1s | GCGTCCCTTACTT CGTGAG | Protease (NS3/4A) genotyping assay | Sequencing |
| 174 | 4a/d_NS3_F1s | CCGTGCGCAGGA GAGG | Protease (NS3/4A) genotyping assay | Sequencing |
| 175 | 4a/d_NS3_F2s | CACGGTCTTGGAC CAAGC | Protease (NS3/4A) genotyping assay | Sequencing |
| 176 | 4a/d_NS3_F3s | GCCTGGTACGAA CTGACACC | Protease (NS3/4A) genotyping assay | Sequencing |
| 177 | 4a/d_NS3_R2s | GCCACTTCCTGTT GGTGC | Protease (NS3/4A) genotyping assay | Sequencing |
| 178 | 4a/d_NS3_R3s | CTGAGTCAAAGT CGCCGGT | Protease (NS3/4A) genotyping assay | Sequencing |
| 179 | 4a/d_NS3_R4s | GACATGCAGGCC ATGATGTA | Protease (NS3/4A) genotyping assay | Sequencing |
| 180 | 4a/d_NS3_in_F | TAAGGGGATTAC CTGTCTCGGC | N-terminal 181aa of NS3 genotyping assay | Amplification and sequencing |
| 181 | 4a/d_NS3_out_F | AGTTGTGTTCACG CCCATGGAG | N-terminal 181aa of NS3 genotyping assay | Amplification |
| 182 | 4a/d_NS3_in_R | GGGACTTTGGTGC TCTTGCC | N-terminal 181aa of NS3 genotyping assay | Amplification and sequencing |
| 183 | 4a/d_NS3_out_R | TCGATGCCATATG CCTTGGAC | N-terminal 181aa of NS3 genotyping assay | Amplification |
| 184 | 4a/d_NS4B/5A_out_F | TTTCAGTGGGCAG CGTGGT | NS4B/5A genotyping assay | Amplification |
| 185 | 4a/d_NS4B/5A_in_F | AGCGTGGTGATC GTCGGGAG | NS4B/5A genotyping assay | Amplification and sequencing |
| 186 | 4a/d_NS4B/5A_out_R | CCTGCAGGCGGT CGAAGG | NS4B/5A genotyping assay | Amplification |
| 187 | 4a/d_NS4B/5A_in_R | CGAAGGTCACCTT CTTCTGCCG | NS4B/5A genotyping assay | Amplification and sequencing |
| 188 | 4a/d_NS4B_R1s | AGACATGAGGGA AGCAATGG | NS4B/5A genotyping assay | Sequencing |
| 189 | 4a/d_NS4B_F1sb | TGTGCAGTGGAT GAACCG | NS4B/5A genotyping assay | Sequencing |
| 190 | 4a/d_NS5A_R1s | ACTCTGCGAACCT CCACG | NS4B/5A genotyping assay | Sequencing |
| 191 | 4a/d_NS5A_F1s | GTTGACAGACCC ATCACACAT | NS4B/5A genotyping assay | Sequencing |
| 192 | 4a/d_NS5A_R2s | TCGTCTGTCTCAA CCCTGGT | NS4B/5A genotyping assay | Sequencing |
| 193 | 4a/d_NS5A_F2sb | TCTTACTCGTCAA TGCCTCC | NS4B/5A genotyping assay | Sequencing |
| 194 | 4a/d_NS5B_out_F | CGGGGTAACACA AGATAACATCAAG | Polymerase (NS5B) genotyping assay | Amplification |

TABLE 5-continued

| SEQ ID NO | Primer name | Sequence (5' to 3') | Remark | Amplification/ Sequencing |
|---|---|---|---|---|
| 195 | 4a/d_NS5B_out_R | ACCCTAAGGTCG GAGTGTTAAGCT | Polymerase (NS5B) genotyping assay | Amplification |
| 196 | 4a/d_NS5B_in_F | ACAAGATAACAT CAAGTGCCCCTG | Polymerase (NS5B) genotyping assay | Amplification |
| 197 | 4a/d_NS5B_in_R | AAGGTCGGAGTG TTAAGCTGCCTA | Polymerase (NS5B) genotyping assay | Amplification and sequencing |
| 198 | 4a/d_NS5A_F2sc | CTTATTCGTCAAT GCCTCCAC | Polymerase (NS5B) genotyping assay | Sequencing |
| 199 | 4a/d_NS5B_F1s | ATCATGGCCAAA AATGAGGT | Polymerase (NS5B) genotyping assay | Sequencing |
| 200 | 4a/d_NS5B_F2s | GCCTTCACGGAG GCTATGAC | Polymerase (NS5B) genotyping assay | Sequencing |
| 201 | 4a/d_NS5B_F3bs | TGTGGCATATACC TCTTTAACTGG | Polymerase (NS5B) genotyping assay | Sequencing |
| 202 | 4a/d_NS5B_R2s | GGAGTCAAAGCA GCGGG | Polymerase (NS5B) genotyping assay | Sequencing |
| 203 | 4a/d_NS5B_R3s | CAGGAATTGACT GGAGTGTGTC | Polymerase (NS5B) genotyping assay | Sequencing |
| 204 | 4a/d_NS5B_R4s | GCACAGGAGTAA ATAGCGGG | Polymerase (NS5B) genotyping assay | Sequencing |

The invention claimed is:

1. Method for determining drug resistance mutations in any of the non-structural protein regions NS3 to NS5B of Hepatitis C Virus (HCV) for genotypes 1 to 6, more in particular for subtype specific genotypes 1a, 1b, 2a, 2b, 3a, 4a and 4d, present in a sample comprising:

a) obtaining said sample from a patient, b) extracting viral genetic material from said sample, c) amplification of the NS5B region of HCV to generate a DNA amplicon of 388 base pairs by using primers having the sequences selected from the group consisting of SEQ ID NO's 1-5, d) sequencing of the amplicon to obtain a sequence of 329 base pairs by using the sequences selected from the group consisting of SEQ ID NO's 3-5, e) performing phylogenetic tree analysis using the 329 base pair sequence information of NS5B to obtain HCV-subtype information in said patient sample, f 1) using subtype-specific primers having the sequences selected from either the group consisting of SEQ ID NO's 6-9, 42-45, 104-107, 120-123, 145-148 or 180-183 for the generation of a DNA amplicon comprising the non-structural protein NS3 (N-terminal 181 amino acids), g 1) sequencing the NS3 amplicon to obtain a sequence of 543 base pairs by using the sequences selected from the group consisting of SEQ ID NO's 8 and 9; 43 and 45-46; 104 and 106; 120 and 122; 146 and 148 or 180 and 182 h) aligning the sequence obtained in step (g 1), (g 2), (g 3) or (g 4) with a reference or wild-type HCV sequence, i) determining drug resistance mutation(s) in the viral genetic material present in patient sample, j) generating a NS3 amplicon starting from the DNA amplicon comprising the NS3 (N-terminal 181 amino acids) as obtained in step (f 1) using primers having the sequence of SEQ ID NO 11 and 12, k) inserting, by InFusion™ cloning or in vitro recombination, said amplicon obtained in step (i) into a NS3 deleted replication incompetent marker containing shuttle vector having the sequence of SEQ ID NO 10 to obtain a NS3 replication competent recombinant HCV replicon, l) generating RNA, by in vitro transcription, from said HCV replicon obtained in step (k)

m) transfecting said RNA into suitable cells, n) determining, based on the expression of the marker gene, the $EC_{50}$ value and/or fold change as a measure for the presence of drug resistance mutations in a sample.

* * * * *